US008420091B2

(12) United States Patent
Rohlff et al.

(10) Patent No.: US 8,420,091 B2
(45) Date of Patent: Apr. 16, 2013

(54) MATRIPTASE PROTEIN AND USES THEREOF

(75) Inventors: Christian Rohlff, Abingdon (GB); Jonathan Alexander Terrett, San Jose, CA (US)

(73) Assignees: Oxford BioTherapeutics Ltd., Abingdon (GB); Medarex, Inc., Princeton, NJ (US)

( * ) Notice: Subject to any disclaimer, the term of this patent is extended or adjusted under 35 U.S.C. 154(b) by 0 days.

(21) Appl. No.: 12/701,566

(22) Filed: Feb. 7, 2010

(65) Prior Publication Data

US 2010/0285017 A1 Nov. 11, 2010

Related U.S. Application Data

(63) Continuation of application No. PCT/US2008/009512, filed on Aug. 7, 2008.

(60) Provisional application No. 60/693,837, filed on Aug. 7, 2007.

(51) Int. Cl.
*A61K 39/395* (2006.01)

(52) U.S. Cl.
USPC ..................................................... 424/141.1

(58) Field of Classification Search ........................ None
See application file for complete search history.

(56) References Cited

U.S. PATENT DOCUMENTS

| 5,972,616 | A | 10/1999 | O'Brien et al. | |
|---|---|---|---|---|
| 6,451,500 | B1 | 9/2002 | Leon | |
| 6,649,741 | B1 * | 11/2003 | O'Brien et al. | 530/387.1 |
| 6,903,201 | B2 | 6/2005 | Padigaru | |
| 7,022,821 | B1 | 4/2006 | O'Brien et al. | |
| 7,030,231 | B1 | 4/2006 | Craik et al. | |
| 7,105,333 | B2 | 9/2006 | Madison et al. | |
| 7,112,430 | B2 | 9/2006 | Madison et al. | |
| 7,125,703 | B2 | 10/2006 | Madison et al. | |
| 7,172,892 | B2 | 2/2007 | Madison et al. | |
| 7,227,009 | B2 | 6/2007 | Craik et al. | |
| 7,291,462 | B2 | 11/2007 | O'Brien et al. | |
| 7,355,015 | B1 | 4/2008 | Dickson et al. | |
| 7,488,813 | B2 | 2/2009 | Pollock et al. | |
| 2006/0171884 | A1 | 8/2006 | Foltz et al. | |

FOREIGN PATENT DOCUMENTS

| WO | 0123524 | | 4/2001 |
|---|---|---|---|
| WO | 0129056 | | 4/2001 |
| WO | 01/57194 | A | 8/2001 |
| WO | 2004/058688 | A | 7/2004 |
| WO | 2006/0068975 | A | 6/2006 |
| WO | 2007047796 | | 4/2007 |

OTHER PUBLICATIONS

Cho, E.G., et al., "N-terminal Processing is Essential for Release of Epithin, a Mouse Type II Membrane Serine Protease*," The Journal of Biological Chemistry, Nov. 30, 2001, vol. 276, No. 48, pp. 44581-44589, XP008100687, ISSN: 0021-9258, p. 44582, par. 5.

Tsuzuki, Satoshi, et al., "Evidence for the occurrence of membrane-type serine protease1/matriptase on the basolateral sides of enterocytes," Bioichemical Journal, vol. 388, No. Part 2, Jun. 2005, pp. 679-687, XP008103674, ISSN: 0264-6021, the whole document.

Everts Maaike, "Targeted therapies directed to tumor-associated antigens," Drugs of the Future, vol. 30, No. 10, Oct. 2005, pp. 1067-1076, XP008103658, ISSN: 0377-8282, the whole document.

Pedley, R. Barbara, "Pharmacokinetics of Monoclonal Antibodies. Implications for Their Use in Cancer Therapy," Clinical Immunotherapeutics, Adis International, Auckland, NZ, vol. 6, No. 1, Jan. 1, 1996, pp. 54-67, XP009100791, ISSN: 1172-7039, the whole document.

Oberst, Michael D., et al., "The Activation of Matriptase Requires Its Noncatalytic Domains, Serine Protease Domains and Its Cognate Inhibitor," Journal of Biological Chemistry, vol. 278, No. 29, Jul. 18, 2003, pp. 26773-26779, XP008100685, ISSN: 0021-9258, the whole document.

Takeuchi, T., et al., "Cellular Localization of Membrane-type Serine Protease 1 and Identification of Protease-activated Receptor-2 and Single-chain Urokinase-type Plasminogen Activator as Substrates*," Journal of Biological Chemistry, American Society of Biolochemical Biologists, Birmingham; US, vol. 275, No. 34, Aug. 25, 2000, pp. 26333-26342, XP001000977, ISNN: 0021-9258, Abstract.

Lin CY, et al., "Purification and characterization of a complex containing matriptase and a Kunitz-type serine protease inhibitor from human milk.", J. Biol. Chem., 1999, pp. 18237-18242, vol. 274, No. 26.

List K et al., "Deregulated matriptase causes ras-independent multistage carcinogenesis and promotes ras-mediated malignant transformation.", Genes Dev., 2005, pp. 1934-1950, vol. 19, No. 16.

List K, et al., "Delineation of matriptase protein expression by enzymatic gene trapping suggests diverging roles in barrier function, hair formation, and squamous cell carcinogenesis.", Am. J. Pathol., 2006, pp. 1513-1525, vol. 168, No. 5.

List K, et al., "Loss of proteolytically processed filaggrin caused by epidermal deletion of Matriptase/MT-SP1.", J. Cell Biol., 2003, pp. 901-910, vol. 163, No. 4.

List K, et al., "Matriptase/MT-SP1 is required for postnatal survival, epidermal barrier function, hair follicle development, and thymic homeostasis.", Oncogene, 2002, pp. 3765-3779, vol. 21, No. 23.

List K, et al., "Matriptase: potent proteolysis on the cell surface.", Mol. Med., 2006, pp. 1-7, vol. 12, Nos. 1-3.

Mildner M, et al., "Gene silencing in a human organotypic skin model.", Biochem. Biophys. Res. Commun., 2006, pp. 76-82, vol. 348, No. 1.

Mori M, et al., "The cytotrophoblast layer of human chorionic villi becomes thinner but maintains its structural integrity during gestation.", Biology of Reproduction, 2007, pp. 164-172, vol. 76.

Netzel-Arnett S, et al., "Evidence for a matriptase-prostasin proteolytic cascade regulating terminal epidermal differentiation.", J. Biol. Chem., 2006, pp. 32941-32945, vol. 281, No. 44.

(Continued)

*Primary Examiner* — Sean Aeder
(74) *Attorney, Agent, or Firm* — Klauber & Jackson LLC

(57) ABSTRACT

The present invention provides methods and compositions for treatment, screening, diagnosis, prognosis and therapy of breast cancer, colorectal cancer, esophageal cancer, gastric cancer, prostate cancer and uterine cancer, for monitoring the effectiveness of breast cancer, colorectal cancer, esophageal cancer, gastric cancer, prostate cancer and uterine cancer treatment, and for drug development.

30 Claims, 10 Drawing Sheets

OTHER PUBLICATIONS

Oberst M, et al., "Matriptase and HAI-1 are expressed by normal and malignant epithelial cells in vitro and in vivo.", Am. J. Pathol., 2001, pp. 1301-1311, vol. 158, No. 4.

Oberst MD, et al., "Characterization of matriptase expression in normal human issues.", J. Histoctiern. Cytochem., 2003, pp. 1017-1025, vol. 51, No. 8.

Oberst MD, et al., "Expression of the serine protease matriptase and its inhibitor HAI-1 in epithelial ovarian cancer: correlation with clinical outcome and tumor clinicopathological parameters.", Clin. Cancer Res., 2002, pp. 1101-1107, vol. 8, No. 4.

Oberst MD, et al., "HAI-1 regulates activation and expression of matriptase, a membrane-bound serine proteas.", Am. J. Physiol. Cell Physiol., 2005, pp. C462-C470, vol. 289, No. 2.

Planes C, et al. "Regulation of the epithelial Na+ channel by peptidases.", Curr. Top. Dev. Biol., 2007, pp. 23-46, vol. 78.

Qiu D, et al., "Roles and regulation of membrane-associated serine proteases.", Biochem. Soc. Trans., 2007, pp. 583-587, vol. 35, No. 3.

Riddick AC, et al., "Identification of degradome components associated with prostate cancer progression by expression analysis of human prostatic tissues.", Br. J. Cancer, 2005, pp. 2171-2180, vol. 92, No. 12.

Saleem M, et al., "A novel biomarker for staging human prostate adenocarcinoma: overexpression of matriptase with concomitant loss of its inhibitor, hepatocyte growth factor activator inhibitor-1.", Cancer Epiderniol. Biomarkers Prev., 2006, pp. 217-227, vol. 15, No, 2.

Sanders AJ, et al., "Genetic reduction of matriptase-1 expression is associated with a reduction in the aggressive phenotype of prostate cancer cells in vitro and in vivo.", J. Exp. Ther. Oncol., 2006, pp. 39-48, vol. 6, No. 1.

Santini AD, et al., "Gene expression profiles in primary ovarian serous papillary tumors and normal ovarian epithelium: identification of candidate molecular markers for ovarian cancer diagnosis and therapy.", Int. J. Cancer, 2004, pp. 14-25, vol. 112, No. 1.

Santin AD, et al., "The novel serine protease tumor-associated differentially expressed gene-15 (matriptase/MT- SP1) is highly overexpressed in cervical carcinoma.", Cancer, 2003, pp. 1898-1904, vol. 98, No. 9.

Sato N, et al., "Discovery of novel targets for aberrant methylation in pancreatic carcinoma using high-throughput microarrays.", Cancer Res., 2003, pp. 3735-3742, vol. 63, No. 13.

Satomi S, et al., "A role for membrane-type serine protease (MT-SP1) in intestinal epithelial turnover.", Biochem. Biophys. Res. Commun., 2001, pp. 995-1002, vol. 287, No. 4.

Seitzi, et al., "Membrane-type serine protease-1/matriptase induces interleukin-6 and -8 in endothelial cells by activation of protease-activated receptor-2: potential implications in atherosclerosis.", Arterioscler. Thromb. Vasc. Biol., 2007, pp. 769-775, vol. 27, No. 4.

Shi Y, et al., "Study on post-translational processing and active forms of the novel metastasis-associated protein SNC19.", Zhejiang Da Xue Xue Bao Yi Xue Ban., 2005, pp. 38-42, vol. 34, No. 1.

Siddiqui SF, et al., "Coexpression of beta1,6-N-acetylglucosaminyitransferase V glycoprotein substrates defines aggressive breast cancers with poor outcome.", Cancer Epidemiol. Biomarker Prev., 2005, pp. 2517-2523, vol. 14, No. 11 pt1.

Steinmetzer T, et al., "Secondary amides of sulfonylated 3-amidinophenylalanine. New potent and selective inhibitors of matriptase.", J. Med. Chem., 2006, pp. 4116-4126, vol. 49, No. 14.

Stoop AA, et al, "Engineering of a macromolecuar scaffold to develop specific protease inhibitors.", Nature Biotechnology, 2003, pp. 1063-1068, vol. 21.

Sun J, et al., "Potent and selective inhibition of membrane-type serine protease 1 by human single-chain antibodies.", Biochemistry, 2003, pp. 802-900, vol. 42, No. 4.

Sun LF, et al., "SNC19/ST14 gene transfection and expression influence the biological behavior of colorectal cancer cells.", Zhonghua Yi Xue Za Zhi., 2004, pp. 843-848, vol. 84, No. 10.

Suzuki M, et al., "Bikunin target genes in ovarian cancer cells identified by microarray analysis.", J. Biol. Chem., 2003, pp. 14640-14646, vol. 278, No. 17.

Suzuki M, et al., "inhibition of tumor invasion by genomic down-regulation of matriptase through suppression of activation of receptor-bound pro-urokinase.", J. Biol. Chem., 2004; pp. 14899-14908, vol. 279, No. 15.

Szabo R, et al.., "Matriptase inhibition by hepatocyte growth factor activator inhibitor-1 is essential for placental development.", Oncogene, 2007, pp. 1546-1556, vol. 26.

Takeuchi T, et al., "Reverse biochemistry use of macromolecular protease inhibitors to dissect complex biological processes and identify a membrane-type serine protease in epithelial cancer and normal tissue.", Proc. Natl. Acad. Sci. USA, 1999, pp. 11054-11061, vol. 96, No. 20.

Tanimoto H, et al,, "Ovarian tumor cells express a transmembrane serine protease: a potential candidate for early, diagnosis and therapeutic intervention.", Tumour Biol., 2001, pp. 104-114, vol. 22, No. 2.

Tanimoto H, et al., "Transmembrane serine protease TADG-15 (ST14/Matriptase/MT-SP1): expression and prognostic value in ovarian cancer.", Br. J. Cancer., 2005, pp. 278-283, vol. 92, No. 2.

Tsai WC, et al, "Increasing EMMPRIN and matriptase expression in hepatocellular carcinoma: tissue microarray analysis of immunohistochemical scores with clinicopathological parameters.", Histopathology, 2006, pp. 388-395, vol. 49, No. 4.

Uhland K, "Matriptase and its putative role in cancer.", Cell. Mol. Life Sci., 2006, pp. 2968-2378, vol. 63, No. 24.

Vettel U, et al., "Charge-dependent binding of granzyme A (MTSP-1) to basement membranes,", Eur. J. Immunol., 1993, pp. 279-282. vol. 23, No. 1.

Vogel LK, et al., "The ratio of Matriptase/HAI-1 mRNA is higher in colorectal cancer adenomas and carcinomas than corresponding tissue from control individuals.", BMC Cancer, 2006, p. 176, vol. 6.

Welm AL, et al., "The macrophage-stimulating protein pathway promotes metastasis in a mouse model for breast cancer and predicts poor prognosis in humans.", Proc. Natl. Acad. Sci. USA, 2007, pp. 7570-7575, vol. 104, No. 18.

Yamasaki Y, et al., "Inhibition of membrane-type serine protease 1/matriptase by natural and synthetic protease inhibitors.", J. Nutr. Sci. Vitaminol., 2003, pp. 27-32, vol. 49, No. 1.

Zeeuwen PL., "Epidermal differentiation: the role of proteases and their inhibitors.", Eur. J. Cell Biol., 2004, pp. 761-773, vol. 83, Nos. 11-12.

Zeng L, et al., "Expression of serine protease SNC19/matriptase and its inhibitor hepatocyte growth factor activator inhibitor type 1 in normal and malignant tissues of gastrointestinal tract.", World J. Gastroenterol., 2005, pp. 6202-6207, vol. 11, No. 39.

Zhang Y, et al., "Assignment1 of human putative tumor suppressor genes ST13 (alias SNC6) and ST14 (alias SNC19) to human chromosome bands 22q13 and 11q24→q25 by in situ hybridization,", Cytogenet. Cell Genet., 1998, pp. 56-57, vol. 83, Nos. 1-2.

Chen M. et al, "The epidermal growth factor (EGFR) is proteolytically modified by the Matriptase-Prostasin serine protease cascade in cultured epithelial cells.", Biochim. Biophys. Acta. 2008, pp. 896-903, vol. 1783.

Lee M.S."Matrix-degradina type II transmembrane serine protease matriptase: Its role in cancer development and malignancy.", J. Cancer Mol., 2006, pp. 183-190, vol. 2, No. 5.

Ahmed S, et al., "Identification of membrane-bound serine proteinase matriptase as processing enzyme of insulin-like growth factor binding protein-related protein-1 (IGFBP-rP1/angiomodulin/mac25).", FEBS Journal., 2006, pp. 815-627, vol. 273, No. 3.

Aimes RT, et al., "Endothelial cell serine proteases expressed during vascular morphogenesis and angiogenesis.", Thromb Haemost., 2003, pp. 561-572, vol. 89, No. 3.

Alef T, et al., "Ichthyosis, follicular atrophoderma, and hypotrichosis caused by mutations in ST14 is associated with impaired profilaggrin processing.", J. Invest. Dermatol., 2009, pp. 862-869, vol. 129, No. 4.

Andre M, et al., "Proteornic analysis of the tetraspanin web using LC-ESI-MS/MS and MALDI-FTICR-MS." Proteomics, 2006, pp. 1437-1449, vol. 6, No. 5.

Basel-Vanagaite L. et al., "Autosomal recessive ichthyosis with hypotrichosis caused by a mutation in ST14, encoding type II transmembrane serine protease matriptase.", Am. J. Hum. Genet., 2007; pp. 467-477, vol. 80, No. 3.

Benaud C, et al., "Regulation of the activity of matriptase on epithelial cell surfaces by a blood-derived factor.", Eur. J. Biochem., 2001, pp. 1439-1447, vol. 268, No. 5.

Benaud C, et al., "Sphingosine 1-phosphate, present in serum-derived lipoproteins, activates matriptase.", J. Biol. Chem., 2002. pp. 10539-10546, vol. 277, No. 12.

Benaud CM, et al., "Deregulated activation of matriptase in breast cancer cells.", Clin, Exp. Metastasis, 2002, pp. 639-649; vol. 19, No. 7.

Betsunoh H, et al., "Clinical relevance of hepsin and hepatocyte growth factor activator inhibitor type 2 expression in renal cell carcinoma.", Cancer Sci., 2007, pp. 491-498, vol. 98, No. 4.

Bhatt AS, et al, "Adhesion signaling by a novel mitotic substrate of src kinases.", Oncogene., 2005, pp. 5333-5343, vol. 24.

Bhatt AS, et al, "Coordinate expression and functional profiling identify an extracellular proteolytic signaling pathway.", Proc. Natl. Acad. Sci. USA, 2007, pp. 5771-5776, vol. 104, No. 14.

Bhatt AS, et al,, "Quantitation of membrane type serine protease 1 (MT-SP1) in transformed and normal cells.", Biol. Chem., 2003, pp. 257-266, vol. 384, No. 2.

Bugge TH, et al. "Matriptase", UCSD Nature Molecule Pages, 2007 (http://www.signaling-gateway.org/molecule/query?afcsid=A003972).

Cao J, et al., "A novel serine protease SNC19 associated with human colorectal cancer.", Chin. Med. J. (Engl), 2001, pp. 726-730, vol. 114, No. 7.

Chen M, et al., "Prostasin induces protease-dependent and independent molecular changes in the human prostate carcinoma cell line PC-3.", Biochim. Biophys. Acta., 2007, pp. 1133-1140, vol. 1773, No. 7.

Cheng MF, et al., "Expression of EMMPRIN and matriptase in esophageal squamous cell carcinoma: correlation with clinicopathologicai parameters.", Dis Esophagus, 2006, pp. 482-486, vol. 19, No. 6.

Cleator S, et al., "Gene expression patterns for doxorubicin (Adriamycin) and cyclophosphamide (cytoxan) (AC) response and resistance.", Breast Cancer Res. Treat , 2006, pp. 229-233, vol. 95, No. 3.

Desilets A, et al., "Inhibition of human matriptase by eglin c variants:", FEBS Lett., 2006, pp. 2227-2232, vol. 580, No. 9.

Ding KF, et al., "Effect of SNC19/ST14 gene overexpression on invasion of colorectal cancer cells.", World J. Gastroenterol,, 2005, pp. 5651-5654, vol. 11, No. 36.

Enyedy IJ, et al., "Structure-based approach for the discovery of bis-benzamidines as novel inhibitors of matriptase.", J. Med. Chem., 2001, pp. 1349-1355, vol. 44, No. 9.

Farady CJ, et al., "The mechanism of inhibition of antibody-based inhibitors of membrane-type serine protease 1 (MT-SP1)", J. Mol. Biol., 2007, pp. 1041-1051, vol. 369, No. 4.

Forbs D, et al., "In vitro inhibition of matriptase prevents invasive growth of cell lines of prostate and colon carcinoma.", Int. J. Oncol., 2005, pp. 1061-1070, vol. 27, No. 4.

Friedrich R, et al., "Catalytic domain structures of MT-SP1/matriptase, a matrix-degrading transmembrane serine proteinase.", J. Biol. Chem., 2002, pp. 2160-2168, vol. 277, No. 3.

Galkin AV, et al., "CVS-3983, a selective rnatriptase inhibitor, suppresses the growth of androgen independent prostate tumor xenografts.", Prostate, 2004, pp. 228-235, vol. 61, No. 3.

Ge W, et al., "Protein interaction analysis of ST14 domains and their point and deletion mutants.", J. Biol. Chem., 2006. pp. 7406-7412, vol. 281, No. 11.

Habbe N, et al., "Identification of methylation-associated gene expression in neuroendocrine pancreatic tumor cells.", Pancreatology, 2007, pp. 352-359, vol. 7.

Hoang CD, et al., "Gene expression profiling identifies matriptase overexpression in malignant mesothelioma.", Chest, 2004, pp. 1843-1852, vol. 125, No. 5.

Hooper JD, et al., "Type II transmembrane serine proteases. Insights into an emerging class of cell surface proteolytic enzymes.", J. Biol. Chem., 2001, pp. 857-860, vol. 276, No. 2.

Hung RJ, et al., "Assembly of adherens junctions is required for sphingosine 1-phosphate-induced matriptase accumulation and activation at mammary epithelial cell-cell contacts.", Am. J. Physiol. Cell Physiol., 2004, pp. C1159-C1169, vol. 286, No. 5.

Ihara S, et al., "Addition of beta1-6 GlcNAc branching to the oligosaccharide attached to Asn 772 in the serine protease domain of matriptase plays a pivotal role in its stability and resistance against trypsin.", Glycobiology, 2004, pp. 139-146, vol. 14, No. 2.

Ihara S, et al., "Prometastatic effect of N-acetylglucosaminyltransferase V is due to modification and stabilization of active matriptase by adding beta 1-6 GlcNAc branching.", J. Biol. Chem., 2002, pp. 16960-16967, vol. 277, No. 19.

Ito Y, et al., "Co-expression of matriptase and N-acetylglucosaminyltransferase V in thyroid cancer tissues—its possible role in prolonged stability in vivo by aberrant glycosylation.", Glycobiology, 2006, pp. 368-374, vol. 16, No. 5.

Jarzab B. et al., "Gene expression profile of papillary thyroid cancer: sources of variability and diagnostic implications.", Cancer Res., 2005, pp. 1587-1597, vol. 65, No. 4.

Jin JS, et al., "Expression of serine protease matriptase in renal cell carcinoma: correlation of tissue microarray immunohistochemical expression analysis results with clinicopathological parameters.", Int, J. Surg. Pathol., 2006, pp. 65-72, vol. 14, No. 1.

Jin JS, et al., "Expression of the serine protease, matriptase, in breast ductal carcinoma of Chinese women: correlation with clinicopathological parameters.", Histol. Histopathol., 2007, pp. 305-309, vol. 22, No. 3.

Jin JS, et al., "Increasing expression of serine protease matriptase in ovarian tumors: tissue microarray analysis of immunostaining score with clinicopathological parameters.", Mod. Pathol., 2006, pp. 447-452, vol. 19, No. 3.

Jin X, et al., "Matriptase activates stromelysi (MMP-3) and promotes Tumor growth and angiogenesis.", Cancer Sci., 2006, pp. 1327-1334, vol. 97, No. 12.

Jin X, et al,, "Production of soluble rnatriptase by human cancer cell lines and cell surface activation of its zymogen by trypsin.", J. Cell Biochem., 2005, pp. 632-647, vol .95, No. 3.

Johnson MD, et al., "Possible role of matriptase in the diagnosis of ovarian cancer.", Expert Rev. Mol. Diagn., 2003, pp. 331-338, vol. 3, No. 3.

Kang JY, et al., "Tissue microarray analysis of hepatocyte growth factor/Met pathway components reveals a role for Met, matriptase, and hepatocyte growth factor activator inhibitor 1 in the progression of node-negative breast cancer.", Cancer Res., 2003, pp. 1101-1105, vol. 63.

Kilpatrick LM, et al., "Initiation of plasminogen activation on the surface of monocytes expressing the type II transmembrane serine protease matriptase.", Blood, 2006, pp. 2616-2623, vol. 108, No. 8.

Kiyomiya K, et al., "Matriptase activation and shedding with HAI-1 is induced by steroid sex hormones in human prostate cancer cells, but not in breast cancer cells.", Am. J. Physiol. Cell Physiol., 2006, pp. C40-C49, vol. 291, No. 1.

Lee JW, et al., "Expression of TAGD-15 in Squamous Cell Carcinoma of the Uterine Cervix.",Korean J. Obstet. Gynecol., 2004, pp. 2465-2471, vol. 47, No. 12.

Lee JW, et al., "Increased expression of matriptase is associated with histopathologic grades of cervical neoplasia,", Hum. Pathol., 2005, pp. 626-633, vol. 36. No. 6.

Lee MS, et al., "Autoactivation of matriptase in vitro: requirement for biomembrane and LDL receptor domain." Am. J. Physiol Cell Physiol., 2007, pp. C95-C105, vol. 293, No. 1.

Lee MS, et al., "Simultaneous activation and hepatocyte growth factor activator inhibitor 1-mediated inhibition of matriptase induced at activation foci in human mammary epithelial cells.", Am. J. Physiol. Cell Physiol., 2005. pp. C932-C941, vol. 288, No. 4.

Lee SL, et al., "Activation of hepatocyte growth factor and urokinase/plasminogen activator by matriptase, an epithelial membrane serine protease.", J. Biol. Chem., 2000, pp. 36720-36725, vol. 275, No. 47.

Lenaour F., et al., "Profiling of the tetraspanin web of human colon cancer cells." Mol. Cell. Proteomics, 2006, pp. 845-857, vol. 5, France.

Li P, et al., "Design and synthesis of novel and potent inhibitors of the type II transmembrane serine protease, matriptase, based upon the sunflower trypsin inhibitor-1.", J. Med. Chem., 2007, pp. 5976-5983, vol. 50, No. 24.

Lin CY, et al., "Molecular cloning of cDNA for matriptase, a matrix-degrading senne protease with trypsin-like activity.", J. Biol. Chem., 1999, pp. 18231-18236, vol. 274, No. 26.

Anonymous, "Anti-ST14 antibody-stem region (ab28267)", 2012, retrieved from the Abcam Internet website.

Anonymous, "Anti-ST14 antibody-stem region (ab28267)", 2012, Scientific support/Abcam, retrieved from the Abcam Internet website.

* cited by examiner

Figure 1

Matriptase (SEQ ID No: 1)

Peptide Source: 1D-GE, Breast cancer

MGSDRARKGGGGPKDFGAGLKYNSRHEKVNGLEEGVEFLPVNNVKKVEKHGPGRWVVLAAVLIGLLLVLLGIG
FLVWHLQYRDVRVQKVFNGYMRITNENFVDAYENSNSTEFVSLASKVKDALKLLYSGVPFLGPYHKESAVTAF
SEGSVIAYYWSEFSIPQHLVEEAERVMAEERVVMLPPRARSLKSFVVTSVVAFPTDSKTVQRTQDNSCSFGLH
ARGVELMRFTTPGFPDSPYPAHARCQWALRGDADSVLSLTFRSFDLASCDERGSDLVTVYNTLSPMEPHALVQ
LCGTYPPSYNLTFHSSQNVLLITLITNTERRHPGFEATFFQLPRMSSCGGRLRKAQGTFNSPYYPGHYPPNID
CTWNIEVPNNQHVKVRFKFFYLLEPGVPAGTCPKDYVEINGEKYCGERS<u>QFVVTSNSNK</u>ITVRFHSDQSYTDT
GFLAEYLSYDSSDPCPGQFTCRTGRCIRKELRCDGWADCTDHSDELNCSCDAGHQFTCKNKFCKPLFWVCDSV
NDCGDNSDEQGCSCPAQTFRCSNGKCLSKSQQCNGKDDCGDGSDEASCPKVNVVTCTKHTYRCLNGLCLSKGN
PECDGKEDCSDGSDEKDCDCGLRSFTRQARVVGGTDADEGEWPWQVSLHALGQGHICGASLISPNWLVSAAHC
YIDDRGFRYSDPTQWTAFLGLHDQSQRSAPGVQERRLKRIISHPFFNDFTFDYDIALLELEKPAEYSSMVRPI
CLPDASHVFPAGKAIWVTGWGHTQYGGTGALILQKGEIRVINQTTCENLLPQQITPRMMCVGFLSGGVDSCQG
DSGGPLSSVEADGRIFQAGVVSWGDGCAQRNKPGVYTRLPLFRDWIKENTGV

Mass Match Peptides (bold):
    FTTPGFPDSPYPAHAR [2]
    GDADSVLSLTFR [3]
    HPGFEATFFQLPR [4]
    SAPGVQERR [6]

Tandem Peptides (underline):
    FTTPGFPDSPYPAHAR [2]
    GDADSVLSLTFR [3]
    SQFVVTSNSNK [8]

Peptide Source: 1D-GE, Colorectal cancer

MGSDRARKGGGGPKDFGAGLKYNSRHEKVNGLEEGVEFLPVNNVKKVEKHGPGRWVVLAAVLIGLLLVLLGIG
FLVWHLQYRDVRVQKVFNGYMRITNENFVDAYENSNSTEFVSLASKVKDALKLLYSGVPFLGPYHKESAVTAF
SEGSVIAYYWSEFSIPQHLVEEAERVMAEERVVMLPPRARSLKSFVVTSVVAFPTDSKTVQRTQDNSCSFGLH
ARGVELMRFTTPGFPDSPYPAHARCQWALRGDADSVLSLTFRSFDLASCDERGSDLVTVYNTLSPMEPHALVQ
LCGTYPPSYNLTFHSSQNVLLITLITNTERRHPGFEATFFQLPRMSSCGGRLRKAQGTFNSPYYPGHYPPNID
CTWNIEVPNNQHVKVRFKFFYLLEPGVPAGTCPKDYVEINGEKYCGERSQFVVTSNSNKITVRFHSDQSYTDT
GFLAEYLSYDSSDPCPGQFTCRTGRCIRKELRCDGWADCTDHSDELNCSCDAGHQFTCKNKFCKPLFWVCDSV
NDCGDNSDEQGCSCPAQTFRCSNGKCLSKSQQCNGKDDCGDGSDEASCPKVNVVTCTKHTYRCLNGLCLSKGN
PECDGKEDCSDGSDEKDCDCGLRSFTRQARVVGGTDADEGEWPWQVSLHALGQGHICGASLISPNWLVSAAHC
YIDDRGFRYSDPTQWTAFLGLHDQSQRSAPGVQERRLKRIISHPFFNDFTFDYDIALLELEKPAEYSSMVRPI
CLPDASHVFPAGKAIWVTGWGHTQYGGTGALILQKGEIRVINQTTCENLLPQQITPRMMCVGFLSGGVDSCQG
DSGGPLSSVEADGRIFQAGVVSWGDGCAQRNKPGVYTRLPLFRDWIKENTGV

Mass Match Peptides (bold):
    FTTPGFPDSPYPAHAR [2]
    HPGFEATFFQLPR [4]
    IFQAGVVSWGDGCAQR [5]
    SFVVTSVVAFPTDSK [7]

Tandem Peptides (underline):
    FTTPGFPDSPYPAHAR [2]
    GDADSVLSLTFR [3]
    SFVVTSVVAFPTDSK [7]

Figure 1 (cont.)

Peptide Source: ICAT, Prostate cancer

MGSDRARKGGGGPKDFGAGLKYNSRHEKVNGLEEGVEFLPVNNVKKVEKHGPGRWVVLAAVLIGLLLVLLGIG
FLVWHLQYRDVRVQKVFNGYMRITNENFVDAYENSNSTEFVSLASKVKDALKLLYSGVPFLGPYHKESAVTAF
SEGSVIAYYWSEFSIPQHLVEEAERVMAEERVVMLPPRARSLKSFVVTSVVAFPTDSKTVQR<u>TQDNSCSFGLH</u>
<u>AR</u>GVELMRFTTPGFPDSPYPAHARCQWALRGDADSVLSLTFRSFDLASCDERGSDLVTVYNTLSPMEPHALVQ
LCGTYPPSYNLTFHSSQNVLLITLITNTERRHPGFEATFFQLPRMSSCGGRLRKAQGTFNSPYYPGHYPPNID
CTWNIEVPNNQHVKVRFKFFYLLEPGVPAGTCPKDYVEINGEKYCGERSQFVVTSNSNKITVRFHSDQSYTDT
GFLAEYLSYDSSDPCPGQFTCRTGRCIRKELRCDGWADCTDHSDELNCSCDAGHQFTCKNKFCKPLFWVCDSV
NDCGDNSDEQGCSCPAQTFRCSNGKCLSKSQQCNGKDDCGDGSDEASCPKVNVVTCTKHTYRCLNGLCLSKGN
PECDGKEDCSDGSDEKDCDCGLRSFTRQARVVGGTDADEGEWPWQVSLHALGQGHICGASLISPNWLVSAAHC
YIDDRGFRYSDPTQWTAFLGLHDQSQRSAPGVQERRLKRIISHPFFNDFTFDYDIALLELEKPAEYSSMVRPI
CLPDASHVFPAGKAIWVTGWGHTQYGGTGALILQKGEIRVINQTTCENLLPQQITPRMMCVGFLSGGVDSCQG
DSGGPLSSVEADGRIFQAGVVSWGDGCAQRNKPGVYTRLPLFRDWIKENTGV

Mass Match Peptides (bold):

Tandem Peptides (underline):
  TQDNSCSFGLHAR [9]

Matriptase Stem Sequence A

MGSDRARKGGGGPKDFGAGLKYNSRHEKVNGLEEGVEFLPVNNVKKVEKHGPGRWVVLAAVLIGLLLVLLGIG
FLVWHLQYRDVR**VQKVFNGYMRITNENFVDAYENSNSTEFVSLASKVKDALKLLYSGVPFLGPYHKESAVTAF
SEGSVIAYYWSEFSIPQHLVEEAERVMAEERVVMLPPRARSLKSFVVTSVVAFPT**DSKTVQRTQDNSCSFGLH
ARGVELMRFTTPGFPDSPYPAHARCQWALRGDADSVLSLTFRSFDLASCDERGSDLVTVYNTLSPMEPHALVQ
LCGTYPPSYNLTFHSSQNVLLITLITNTERRHPGFEATFFQLPRMSSCGGRLRKAQGTFNSPYYPGHYPPNID
CTWNIEVPNNQHVKVRFKFFYLLEPGVPAGTCPKDYVEINGEKYCGERSQFVVTSNSNKITVRFHSDQSYTDT
GFLAEYLSYDSSDPCPGQFTCRTGRCIRKELRCDGWADCTDHSDELNCSCDAGHQFTCKNKFCKPLFWVCDSV
NDCGDNSDEQGCSCPAQTFRCSNGKCLSKSQQCNGKDDCGDGSDEASCPKVNVVTCTKHTYRCLNGLCLSKGN
PECDGKEDCSDGSDEKDCDCGLRSFTRQARVVGGTDADEGEWPWQVSLHALGQGHICGASLISPNWLVSAAHC
YIDDRGFRYSDPTQWTAFLGLHDQSQRSAPGVQERRLKRIISHPFFNDFTFDYDIALLELEKPAEYSSMVRPI
CLPDASHVFPAGKAIWVTGWGHTQYGGTGALILQKGEIRVINQTTCENLLPQQITPRMMCVGFLSGGVDSCQG
DSGGPLSSVEADGRIFQAGVVSWGDGCAQRNKPGVYTRLPLFRDWIKENTGV

| Stem Sequence (bold) | Amino Acids | Seq ID |
|---|---|---|
| VQKVFNGYMRITNENFVDAYENSNSTEFVSLASKVKDALKLLYSGVPFLGP YHKESAVTAFSEGSVIAYYWSEFSIPQHLVEEAERVMAEERVVMLPPRARS LKSFVVTSVVAFPT | 86-201 | 10 |

Figure 2(b)

Matriptase Stem Sequence B

MGSDRARKGGGGPKDFGAGLKYNSRHEKVNGLEEGVEFLPVNNVKKVEKHGPGRWVVLAAVLIGLLLVLLGIG
FLVWHLQYRDVR**VQKVFNGYMRITNENFVDAYENSNSTEFVSLASKVKDALKLLYSGVPFLGPYHKESAVTAF
SEG**SVIAYYWSEFSIPQHLVEEAERVMAEERVVMLPPRARSLKSFVVTSVVAFPTDSKTVQRTQDNSCSFGLH
ARGVELMRFTTPGFPDSPYPAHARCQWALRGDADSVLSLTFRSFDLASCDERGSDLVTVYNTLSPMEPHALVQ
LCGTYPPSYNLTFHSSQNVLLITLITNTERRHPGFEATFFQLPRMSSCGGRLRKAQGTFNSPYYPGHYPPNID
CTWNIEVPNNQHVKVRFKFFYLLEPGVPAGTCPKDYVEINGEKYCGERSQFVVTSNSNKITVRFHSDQSYTDT
GFLAEYLSYDSSDPCPGQFTCRTGRCIRKELRCDGWADCTDHSDELNCSCDAGHQFTCKNKFCKPLFWVCDSV
NDCGDNSDEQGCSCPAQTFRCSNGKCLSKSQQCNGKDDCGDGSDEASCPKVNVVTCTKHTYRCLNGLCLSKGN
PECDGKEDCSDGSDEKDCDCGLRSFTRQARVVGGTDADEGEWPWQVSLHALGQGHICGASLISPNWLVSAAHC
YIDDRGFRYSDPTQWTAFLGLHDQSQRSAPGVQERRLKRIISHPFFNDFTFDYDIALLELEKPAEYSSMVRPI
CLPDASHVFPAGKAIWVTGWGHTQYGGTGALILQKGEIRVINQTTCENLLPQQITPRMMCVGFLSGGVDSCQG
DSGGPLSSVEADGRIFQAGVVSWGDGCAQRNKPGVYTRLPLFRDWIKENTGV

| Stem Sequence (bold) | Amino Acids | Seq ID | Cleavage Site (underline) |
|---|---|---|---|
| VQKVFNGYMRITNENFVDAYENSNSTEFVSLASKVKDALKLL YSGVPFLGPYHKESAVTAFSEG | 86-149 | 11 | G149 |

Figure 2(c)

Matriptase Stem Sequence C

MGSDRARKGGGGPKDFGAGLKYNSRHEKVNGLEEGVEFLPVNNVKKVEKHGPGRWVVLAAVLIGLLLVLLGIG
FLVWHLQYRDVR**VQKVFNGYMRITNENFVDAYENSNSTEFVSLASKVKDALKLLYSGVPFLGPYHKESAVTAF
SEGSVIAYYWSEFSIPQHLVEEAERVMAEERVVMLPPRARSLK**SFVVTSVVAFPTDSKTVQRTQDNSCSFGLH
ARGVELMRFTTPGFPDSPYPAHARCQWALRGDADSVLSLTFRSFDLASCDERGSDLVTVYNTLSPMEPHALVQ
LCGTYPPSYNLTFHSSQNVLLITLITNTERRHPGFEATFFQLPRMSSCGGRLRKAQGTFNSPYYPGHYPPNID
CTWNIEVPNNQHVKVRFKFFYLLEPGVPAGTCPKDYVEINGEKYCGERSQFVVTSNSNKITVRFHSDQSYTDT
GFLAEYLSYDSSDPCPGQFTCRTGRCIRKELRCDGWADCTDHSDELNCSCDAGHQFTCKNKFCKPLFWVCDSV
NDCGDNSDEQGCSCPAQTFRCSNGKCLSKSQQCNGKDDCGDGSDEASCPKVNVVTCTKHTYRCLNGLCLSKGN
PECDGKEDCSDGSDEKDCDCGLRSFTRQARVVGGTDADEGEWPWQVSLHALGQGHICGASLISPNWLVSAAHC
YIDDRGFRYSDPTQWTAFLGLHDQSQRSAPGVQERRLKRIISHPFFNDFTFDYDIALLELEKPAEYSSMVRPI
CLPDASHVFPAGKAIWVTGWGHTQYGGTGALILQKGEIRVINQTTCENLLPQQITPRMMCVGFLSGGVDSCQG
DSGGPLSSVEADGRIFQAGVVSWGDGCAQRNKPGVYTRLPLFRDWIKENTGV

| Stem Sequence (bold) | Amino Acids | Seq ID | Cleavage Site (underline) |
|---|---|---|---|
| VQKVFNGYMRITNENFVDAYENSNSTEFVSLASKVKDALKLL YSGVPFLGPYHKESAVTAFSEGSVIAYYWSEFSIPQHLVEEA ERVMAEERVVMLPPRARSLK | 86-189 | 12 | K189 |

Figure 2(d)

Matriptase Stem Sequence D

MGSDRARKGGGGPKDFGAGLKYNSRHEKVNGLEEGVEFLPVNNVKKVEKHGPGRWVVLAAVLIGLLLVLLGIG
FLVWHLQYRDVR**VQKVFNGYMRITNENFVDAYENSNSTEFVSLASKVKDALKLLYSGVPFLGPYHKESAVTAF
SEGSVIAYYWSEFSIPQHLVEEAERVMAEERVVMLPPRARSLKSFVVTSVVAFPTDSK**TVQRTQDNSCSFGLH
ARGVELMRFTTPGFPDSPYPAHARCQWALRGDADSVLSLTFRSFDLASCDERGSDLVTVYNTLSPMEPHALVQ
LCGTYPPSYNLTFHSSQNVLLITLITNTERRHPGFEATFFQLPRMSSCGGRLRKAQGTFNSPYYPGHYPPNID
CTWNIEVPNNQHVKVRFKFFYLLEPGVPAGTCPKDYVEINGEKYCGERSQFVVTSNSNKITVRFHSDQSYTDT
GFLAEYLSYDSSDPCPGQFTCRTGRCIRKELRCDGWADCTDHSDELNCSCDAGHQFTCKNKFCKPLFWVCDSV
NDCGDNSDEQGCSCPAQTFRCSNGKCLSKSQQCNGKDDCGDGSDEASCPKVNVVTCTKHTYRCLNGLCLSKGN
PECDGKEDCSDGSDEKDCDCGLRSFTRQARVVGGTDADEGEWPWQVSLHALGQGHICGASLISPNWLVSAAHC
YIDDRGFRYSDPTQWTAFLGLHDQSQRSAPGVQERRLKRIISHPFFNDFTFDYDIALLELEKPAEYSSMVRPI
CLPDASHVFPAGKAIWVTGWGHTQYGGTGALILQKGEIRVINQTTCENLLPQQITPRMMCVGFLSGGVDSCQG
DSGGPLSSVEADGRIFQAGVVSWGDGCAQRNKPGVYTRLPLFRDWIKENTGV

| Stem Sequence (bold) | Amino Acids | Seq ID | Cleavage Site (underline) |
|---|---|---|---|
| VQKVFNGYMRITNENFVDAYENSNSTEFVSLASKVKDALKLL YSGVPFLGPYHKESAVTAFSEGSVIAYYWSEFSIPQHLVEEA ERVMAEERVVMLPPRARSLKSFVVTSVVAFPTDSK | 86-204 | 13 | K204 |

Figure 3

Catalytic domain of Matriptase

MGSDRARKGGGGPKDFGAGLKYNSRHEKVNGLEEGVEFLPVNNVKKVEKHGPGRWVVLAAVLIGLLLVLLGIG
FLVWHLQYRDVRVQKVFNGYMRITNENFVDAYENSNSTEFVSLASKVKDALKLLYSGVPFLGPYHKESAVTAF
SEGSVIAYYWSEFSIPQHLVEEAERVMAEERVVMLPPRARSLKSFVVTSVVAFPTDSKTVQRTQDNSCSFGLH
ARGVELMRFTTPGFPDSPYPAHARCQWALRGDADSVLSLTFRSFDLASCDERGSDLVTVYNTLSPMEPHALVQ
LCGTYPPSYNLTFHSSQNVLLITLITNTERRHPGFEATFFQLPRMSSCGGRLRKAQGTFNSPYYPGHYPPNID
CTWNIEVPNNQHVKVRFKFFYLLEPGVPAGTCPKDYVEINGEKYCGERSQFVVTSNSNKITVRFHSDQSYTDT
GFLAEYLSYDSSDPCPGQFTCRTGRCIRKELRCDGWADCTDHSDELNCSCDAGHQFTCKNKFCKPLFWVCDSV
NDCGDNSDEQGCSCPAQTFRCSNGKCLSKSQQCNGKDDCGDGSDEASCPKVNVVTCTKHTYRCLNGLCLSKGN
PECDGKEDCSDGSDEKDCDCGLRSFTRQAR**VVGGTDADEGEWPWQVSLHALGQGHICGASLISPNWLVSAAHC
YIDDRGFRYSDPTQWTAFLGLHDQSQRSAPGVQERRLKRIISHPFFNDFTFDYDIALLELEKPAEYSSMVRPI
CLPDASHVFPAGKAIWVTGWGHTQYGGTGALILQKGEIRVINQTTCENLLPQQITPRMMCVGFLSGGVDSCQG
DSGGPLSSVEADGRIFQAGVVSWGDGCAQRNKPGVYTRLPLFRDWIKENTGV**

| Catalytic Domain Sequence (bold) | Amino Acids | Seq ID | Cleavage Site (underline) |
|---|---|---|---|
| VVGGTDADEGEWPWQVSLHALGQGHICGASLISPNWLVSAAH CYIDDRGFRYSDPTQWTAFLGLHDQSQRSAPGVQERRLKRII SHPFFNDFTFDYDIALLELEKPAEYSSMVRPICLPDASHVFP AGKAIWVTGWGHTQYGGTGALILQKGEIRVINQTTCENLLPQ QITPRMMCVGFLSGGVDSCQGDSGGPLSSVEADGRIFQAGVV SWGDGCAQRNKPGVYTRLPLFRDWIKENTGV | 615-855 | 14 | R614 |

Figure 4

Matriptase stem – hFcG1 fusion protein (SEQ ID No: 15)

**vqkvfngymritnenfvdayensnstefvslaskvkdalkllysgvpflgpyhkesavtafsegsviayywsefsip
qhlveeaervmaeervvmlpprarslksfvvtsvvafpt**asgsgiegrglepkssdkthtcppcpapellggpsvflfppk
pkdtlmisrtpevtcvvvdvshedpevkfnwyvdgvevhnaktkpreeqynstyrvvsvltvlhqdwlngkeykckvsnkal
papiektiskakgqprepqvytlppsrdeltknqvsltclvkgfypsdiavewesngqpennykttppvldsdgsfflyskltvdk
srwqqgnvfscsvmhealhnhytqksislspgk

Quantiles

| Level | Minimum | 10% | 25% | Median | 75% | 90% | Maximum |
|---|---|---|---|---|---|---|---|
| Normal | 0.440286 | 0.440286 | 0.769704 | 0.936737 | 1.169809 | 1.383672 | 1.383672 |
| Prostate | 0.312288 | 0.312288 | 0.651666 | 0.270108 | 12.38386 | 19.98669 | 19.98669 |

Means for Oneway ANOVA

| Level | Number | Mean | Std Error | Lower 95% | Upper 95% |
|---|---|---|---|---|---|
| Normal | 8 | 0.94882 | 1.3446 | -1.806 | 3.7032 |
| Prostate | 8 | 5.93560 | 1.3446 | 3.181 | 8.6900 |

Means Comparisons

Comparisons for each pair using Student's t

| Level | - Level | Difference | Lower CL | Upper CL | p-Value |
|---|---|---|---|---|---|
| Prostate | Normal | 4.986780 | 1.08150 | 8.882056 | 0.0140* |

| Curve | Area | SE | p | 95% CI of Area | Breast vs Normals = breast cancer |
|---|---|---|---|---|---|
| Matriptase,ng/ml | 0.625 | 0.0558 | 0.0123 | 0.516 to 0.735 | have higher values | ns
MATRIPTASE PROTEIN AND USES THEREOF

RELATED APPLICATIONS

The present application is a Continuation of co-pending PCT Application No. PCT/US2008/009512 filed Aug. 7, 2008, which in turn, claims priority from U.S. Provisional Application Ser. No. 60/963,837 filed Aug. 7, 2007. Applicants claim the benefits of 35 U.S.C. §120 as to the PCT application and priority under 35 U.S.C. §119(e) as to the said U.S. Provisional application, and the entire disclosures of both applications are incorporated herein by reference in their entireties.

INTRODUCTION

The present invention relates to the identification of the stem of the matriptase membrane protein associated with breast cancer, colorectal cancer, esophageal cancer, gastric cancer, prostate cancer and uterine cancer which has utility as a marker for breast cancer, colorectal cancer, esophageal cancer, gastric cancer, prostate cancer and uterine cancer and breast cancer, colorectal cancer, esophageal cancer, gastric cancer, prostate cancer and uterine cancer metastases and which also forms a biological target against which therapeutic antibodies (or other affinity reagents) or other pharmaceutical agents can be made, formulations/compositions comprising protein/polypeptide, use of protein/polypeptide or a composition comprising the same in therapy, antibodies for use in therapy, compositions comprising a therapeutic antibody against a relevant polypeptide or a combination of antibodies and use of the same in therapy. The invention also extends to use of the relevant protein, fragments thereof or antibodies directed against the same for diagnosis of one or more of breast cancer, colorectal cancer, esophageal cancer, gastric cancer, prostate cancer and uterine cancer and kits comprising said protein, fragments or antibodies and use of said kits in methods of diagnosis.

BACKGROUND OF THE INVENTION

Breast Cancer

Globally, breast cancer is both the most common cancer (10% of all cancer cases) and the leading cause of cancer death (6% of cancer deaths) in women. Global incidence of breast cancer is over 1 million cases per year, with about 400,000 deaths. Women in North America have the highest rate of breast cancer in the world (over 200,000 new cases per year, with about 40,000 deaths). The chance of developing invasive breast cancer at some time in a woman's life is about 1 in 8. Breast cancer incidence increases with age, rising sharply after age 40. In the USA, about 77% of invasive breast cancers occur in women over age 50. It has been estimated that approximately US$8.1 billion is spent in the USA each year on treating breast cancer.

Breast Cancer Diagnosis

Early diagnosis improves the likelihood that treatment will be successful. Screening methods such as mammograms, clinical breast examinations and breast self-examinations are useful in detecting breast cancer. Current diagnostic methods include breast ultrasound, ductogram, full-field digital mammography (FFDM), scintimammography and MRI. A biopsy (fine needle aspiration biopsy, core biopsy or surgical biopsy) is then performed to confirm the presence of breast cancer. Imaging tests such as a chest x-ray, bone scan, CT, MRI and PET are used to detect if the breast cancer has spread.

Breast Cancer Staging

Breast cancer is staged using the American Joint Committee on Cancer (AJCC) TNM system—Stage 0-Stage IV. Ductal carcinoma in situ (DCIS), a non-invasive cancer which accounts for 20% of new breast cancer cases is Stage 0. Nearly all women diagnosed at this early stage of breast cancer can be cured. Infiltrating (invasive) ductal carcinoma (IDC), which accounts for 80% of invasive breast cancer and infiltrating (invasive) lobular carcinoma (ILC), which accounts for 5% of invasive breast cancers are more severe Stage I-IV cancers and can metastasise.

Breast Cancer Treatment

Breast-conserving surgery (lumpectomy) or mastectomy are the usual treatments for breast cancer. For stage I or II breast cancer, breast-conserving surgery is as effective as mastectomy. Patients can then undergo reconstructive surgery. Axillary lymph node sampling and removal or sentinel lymph node biopsy (SLNB) is performed to see if the cancer has spread to the lymph nodes.

Neoadjuvant chemotherapy can be given before surgery to shrink large cancers. Adjuvant chemotherapy after surgery reduces the risk of breast cancer recurrence. Chemotherapy can also be used as the main treatment for women whose cancer has spread outside the breast and underarm area. Chemotherapeutic agents used include anthracyclines (e.g. methotrexate, fluorouracil, doxorubicin, and epirubicin), taxanes (e.g. paclitaxel, docetaxel, vinorelbine) and alkylating agents (e.g. cyclophosphamide).

Radiation therapy (usually external beam radiation but sometimes brachytherapy) is given once chemotherapy is complete.

Hormone therapy with selective oestrogen receptor modulators (e.g. tamoxifen) can be given to women with oestrogen receptor positive breast cancers. Taking tamoxifen after surgery for 5 years can reduce recurrence by about 50% in women with early breast cancer. Aromatase inhibitors such as exemestane, letrozole or anastrozole can also be used.

Women with HER2 positive cancers (about ⅓ of breast cancers) can be given biological response modifiers such as trastuzumab (Herceptin). Clinical trials have shown that adding trastuzumab to chemotherapy lowers the recurrence rate and death rate over chemotherapy alone after surgery in women with HER2 positive early breast cancers.

Breast Cancer Survival by Stage

This table shows survival by stage based on patients diagnosed between 1995 and 1998. The survival rates now should be slightly higher.

| Stage | 5-year Relative Survival Rate |
|---|---|
| 0 | 100% |
| I | 100% |
| IIA | 92% |
| IIB | 81% |
| IIIA | 67% |
| IIIB | 54% |
| IV | 20% |

Colorectal Cancer

Colorectal cancer (CRC) is one of the leading causes of cancer-related morbidity and mortality, responsible for an estimated half a million deaths per year, mostly in Western, well developed countries. In these territories, CRC is the third most common malignancy (estimated number of new cases per annum in USA and EU is approximately 350,000 per year). Estimated healthcare costs related to treatment for colorectal cancer in the United States are more than $8 billion.

Colorectal Cancer Diagnosis

Today, the fecal occult blood test and colonoscopy, a highly invasive procedure, are the most frequently used screening and diagnostic methods for colorectal cancer. Other diagnostic tools include Flexible Sigmoidoscopy (allowing the observation of only about half of the colon) and Double Contrast Barium Enema (DCBE, to obtain X-ray images).

Colorectal Cancer Staging

CRC has four distinct stages: patients with stage I disease have a five-year survival rate of >90%, while those with metastatic stage IV disease have a <5% survival rate according to the US National Institutes of Health (NIH).

Colorectal Cancer Treatment

Once CRC has been diagnosed, the correct treatment needs to be selected. Surgery is usually the main treatment for rectal cancer, although radiation and chemotherapy will often be given before surgery. Possible side effects of surgery include bleeding from the surgery, deep veinous thrombosis, and damage to nearby organs during the operation.

Currently, 60 percent of colorectal cancer patients receive chemotherapy to treat their disease; however, this form of treatment only benefits a few percent of the population, while carrying with it high risks of toxicity, thus demonstrating a need to better define the patient selection criteria.

Colorectal cancer has a 30 to 40 percent recurrence rate within an average of 18 months after primary diagnosis. As with all cancers, the earlier it is detected the more likely it can be cured, especially as pathologists have recognised that the majority of CRC tumours develop in a series of well-defined stages from benign adenomas.

| Colon Cancer Survival by Stage | |
| --- | --- |
| Stage | Survival Rate |
| I | 93% |
| IIA | 85% |
| IIB | 72% |
| IIIA | 83% |
| IIIB | 64% |
| IIIC | 44% |
| IV | 8% |

Esophageal Cancer

There are approximately 16,000 new cases of esophageal cancer in the US every year, with around 14,000 deaths. Esophageal cancer is 3 to 4 times more common among men than among women. Esophageal cancer is most common in countries such as Iran, China, India and countries of southern Africa. In these countries, the main type of esophageal cancer is squamous cell carcinoma. Adenocarcinoma of the esophagus is the main type among whites and in Western countries, the rate in white men has been increasing at about 2% a year.

Esophageal Cancer Diagnosis

There are no early detection tests to screen the general population for esophageal cancer. Unfortunately, most esophageal cancers do not cause symptoms until they have reached an advanced stage. A barium swallow test is often the first diagnostic test. An upper endoscopy and biopsy are also important tests for diagnosing esophageal cancer. A CT scan, MRI scan, endoscopic ultrasound, bronchoscopy or positron emission tomography can also be used.

Esophageal Cancer Staging

Esophageal cancer is staged using the TNM system of the American Joint Committee on Cancer (AJCC)—stage 0-stage IV. Because esophageal cancer is usually diagnosed at a late stage, most people eventually die of this disease. However, survival rates have been improving. Now, around 15% of patients survive at least 5 years after diagnosis.

Esophageal Cancer Treatment

The options for early treatment of esophageal cancer include surgery (esophagectomy), chemotherapy and radiation therapy. Unfortunately, most esophageal cancers are not found early enough for curative surgery to be a treatment option. Radiation therapy is used as the primary treatment in some patients and can be combined with chemotherapy. A recent study has shown that patients who received chemoradiotherapy followed by surgery had a 5 year survival rate of 39% versus 16% for people who only had surgery. Chemotherapeutic agents used include 5-fluorouracil, cisplatin, carboplatin, bleomycin, mitomycin, doxorubicin, methotrexate, paclitaxel, vinorelbine, topotecan and irinotecan. Other treatments such as mechanical stents and photodynamic therapy are used as palliative treatment when all the cancer cannot be removed.

| Esophageal Cancer Survival by Stage | | |
| --- | --- | --- |
| Stage | Percent of patients | 5-year relative survival rate |
| 0 | 1% | 52% |
| I | 10% | 41% |
| II | 21% | 26% |
| III | 18% | 13% |
| IV | 26% | 3% |
| Unknown | 25% | — |

Gastric Cancer

Gastric cancer is the second-leading cause of cancer-related deaths in the world, with about 700,000 deaths per year, mostly in less developed countries. In the USA, about 22,000 people are diagnosed with gastric cancer each year, with about 11,000 deaths. This figure is approximately ten times higher in Japan. Two thirds of people diagnosed with gastric cancer are older than 65.

Gastric Cancer Diagnosis

Early stage gastric cancer rarely causes symptoms so only about 10-20% of gastric cancers in the USA are found in the early stages, before they have spread to other areas of the body. Studies in the USA have not found mass screening for gastric cancer to be useful because the disease is not that common. Endoscopy followed by a biopsy is the main procedure used to diagnose gastric cancer. Other diagnostic methods include barium upper gastrointestinal radiographs, endoscopic ultrasound, CT scan, PET scan, MRI scan, chest x-ray, laparoscopy, complete blood count (CBC) test and fecal occult blood test.

Gastric Cancer Staging

Gastric cancer is staged using the American Joint Commission on Cancer (AJCC) TNM system—Stage 0-Stage IV. Patients with stage 0 disease have a 5-year survival rate of >90%, while there is usually no cure for patients with stage IV disease where the 5-year survival rate is only 7%. The overall 5-year relative survival rate of people with gastric cancer in the USA is about 23%. The 5-year survival rate for cancers of the proximal stomach is lower than for cancers in the distal stomach.

Gastric Cancer Treatment

Surgery is the only way to cure gastric cancer. There are three types of surgery used—endoscopic mucosal resection (only for early stage gastric cancer), subtotal gastrectomy or total gastrectomy. Gastric cancer often spreads to lymph nodes so these must also be removed. If the cancer has extended to the spleen, the spleen is also removed. Surgery for gastric cancer is difficult and complications can occur.

Chemotherapy may be given as the primary treatment for gastric cancer that has spread to distant organs. Chemotherapy together with external beam radiation therapy may delay cancer recurrence and extend the life span of people with less advanced gastric cancer, especially when the cancer could not be removed completely by surgery. Chemotherapeutic agents used include fluorouracil, doxorubicin, methotrexate, etoposide and cisplatin. More recently, imatinib mesylate (Gleevec) has been trialled in gastrointestinal stromal tumours (GIST), improving progression free survival.

Gastric Cancer Survival by Stage

| Stage | Survival Rate |
|---|---|
| 0 | >90% |
| IA | 80% |
| IB | 60% |
| II | 34% |
| IIIA | 17% |
| IIIB | 12% |
| IV | 7% |

Prostate Cancer

Prostate cancer is the third most common cancer in the world amongst men and it accounts for 5.4% of all cancer cases globally and 3.3% of cancer-related deaths. Global incidence of prostate cancer is around 680,000 cases, with about 221,000 deaths. In the USA, prostate cancer is the most common cancer, other than skin cancers, in American men. About 234,460 new cases of prostate cancer are diagnosed in the USA each year. About 1 man in 6 will be diagnosed with prostate cancer during his lifetime, but only 1 in 34 will die of it. A little over 1.8 million men in the USA are survivors of prostate cancer. The risk of developing prostate cancer rises significantly with age and 60% of cases occur in men over the age of 70. Prostate cancer is the second leading cause of cancer death in American men. Around 27,350 men in the USA die of prostate cancer each year. Prostate cancer accounts for about 10% of cancer-related deaths in men. Modern methods of detection and treatment mean that prostate cancers are now found earlier and treated more effectively. This has led to a yearly drop in death rates of about 3.5% in recent years. Prostate cancer is most common in North America and northwestern Europe. It is less common in Asia, Africa, Central America, and South America. It has been estimated that approximately US$8.0 billion is spent in the USA each year on treating prostate cancer.

Prostate Cancer Diagnosis

Prostate cancer can often be found early by testing the amount of prostate-specific antigen (PSA) in the blood. A digital rectal exam (DRE) can also be performed. However, there are potential problems with the current screening methods. Neither the PSA test nor the DRE is 100% accurate. A core needle biopsy is the main method used to diagnose prostate cancer. A transrectal ultrasound (TRUS) may be used during a prostate biopsy.

Prostate Cancer Staging

Prostate cancers are graded according to the Gleason system, graded from 1-5, which results in the Gleason score, from 1-10. Prostate cancer is staged using the American Joint Committee on Cancer (AJCC) TNM system and combined with the Gleason score to give stages from I-IV.

Ninety one percent of all prostate cancers are found in the local and regional stages; the 5-year relative survival rate for these men is nearly 100%. The 5-year relative survival rate for men whose prostate cancers have already spread to distant parts of the body at the time of diagnosis is about 34%.

Prostate Cancer Treatment

Because prostate cancer often grows very slowly, some men never have treatment and expectant management is recommended. If treatment is required and the cancer is not thought to have spread outside of the gland, a radical prostatectomy can be performed. Transurethral resection of the prostate (TURP) can be performed to relieve symptoms but not to cure prostate cancer.

External beam radiation therapy (three-dimensional conformal radiation therapy (3DCRT), intensity modulated radiation therapy (IMRT) or conformal proton beam radiation therapy) or brachytherapy can also be used as treatment.

Cryosurgery is sometimes used to treat localized prostate cancer but as not much is known about the long-term effectiveness of cryosurgery, it is not routinely used as a first treatment for prostate cancer. It can be used for recurrent cancer after other treatments.

Androgen deprivation therapy (ADT) (orchiectomy or luteinizing hormone-releasing hormone (LHRH) analogs or antagonists) can be used to shrink prostate cancers or make them grow more slowly.

Chemotherapy is sometimes used if prostate cancer has spread outside of the prostate gland and is hormone therapy resistant. Chemotherapeutic agents include docetaxel, prednisone, doxorubicin, etoposide, vinblastine, paclitaxel, carboplatin, estramustine, vinorelbine. Like hormone therapy, chemotherapy is unlikely to result in a cure.

Uterine Cancer

More than 95% of cancers of the uterus are carcinomas—either cervical carcinomas or endometrial carcinomas.

Cervical Cancer

Cervical cancer is second only to breast cancer as the most common malignancy in both incidence and mortality and remains a significant public health problem throughout the world. In the USA alone, invasive cervical cancer accounts for approximately 19% of all gynecological cancers. In the USA, about 9,710 cases of invasive cervical cancer are diagnosed each year, with 3,700 deaths. Non-invasive cervical cancer (carcinoma in situ) is about 4 times more common than invasive cervical cancer. Between 1955 and 1992, the number of cervical cancer deaths in the United States dropped by 74%. The main reason for this change is the increased use of the Pap test screening procedure. The death rate from cervical cancer in the USA continues to decline by nearly 4% a year. Half of women diagnosed with this cancer are between the ages of 35 and 55. Cervical cancer occurs most often in Hispanic women; the rate is over twice that in non-Hispanic white women. African-American women develop this cancer about 50% more often than non-Hispanic white women. In many developing countries, where mass screening programs are not widely available, the clinical problem is more serious. Worldwide, the number of new cases is estimated to be 471,000 with a four-year survival rate of only 40% (Munoz et al., 1989, Epidemiology of Cervical Cancer in: "Human Papillomavirus", New York, Oxford Press, pp 9-39; National Institutes of Health, Consensus Development Conference Statement on Cervical Cancer, Apr. 1-3, 1996). These cases are usually diagnosed at an invasive late stage, rather than as precancers or early cancers.

Cervical Cancer Diagnosis

Early detection greatly improves the chances of successful treatment and prevents any early cervical cell changes from becoming cancerous. Although the Pap test is the most cost-effective cancer screening test developed to date (Greenberg, M. D., et al., 1995, Clin Obstet Gynecol 38(3): 600-9), it is not perfect. One of its limitations is that Pap tests are examined by humans, so an accurate analysis of the hundreds of thousands of cells in each sample is not always possible. It was reported that the mean sensitivity of primary Pap tests is approximately 58% and the accuracy of a repeat test is only about 66% (Fahey M. T., et al., 1995, Am. J. Epidemiol. 141: 680-689). The low sensitivity and poor reproducibility have complicated the management of ASCUS (atypical squamous cells of undetermined significance) and LSIL (low-grade squamous intraepithelial lesion) patients. If an "accelerated repeat Pap test" is recommended for the follow-up of women with primary diagnosis of ASCUS or LSIL, patients will risk delay in diagnosis of potential high-grade lesions. However, if these patients are universally referred to colposcopy, the vast majority of women will be over treated. Only 5-10% of women with ASCUS have high-grade disease upon colposcopy, and more than 80% of LSIL will regress to normal or stay in their current state (Cox, J. T., 2000, Clinics in Laboratory Medicine. 20 (2): 303-343, Ostor A. G., 1993, Int. J. Gynecol. Pathol. 12 (2): 186-192). New tests can identify HPVs by finding their DNA in the cells. Many doctors are now testing for HPV if the Pap test result is mildly abnormal. However, since the vast majority of HPV infections and the resulting squamous intraepithelial lesions regress spontaneously, especially in young women, HPV testing cannot specifically identify patients whose lesions will persist or progress to invasive carcinoma (Sasieni, P. D., 2000, J. Am. Med. Womens Assoc. 55 (4): 216-219, Sasieni, P. D., 2000, Br. J. Cancer, 83 (5): 561-565). A vaccine (Gardisil) has been approved for use by FDA and it protects against HPV types 16, 18, 6, and 11. The vaccine does not protect against all cancer-causing types of HPV, so Pap tests are still necessary. Other tests are required to diagnose cervical cancer following the Pap test including a colposcopy and biopsy, and sometimes an endocervical scraping. The biopsy can be either a colposcopic biopsy, an endocervical curettage or a cone biopsy—LEEP (LLETZ) or cold knife cone biopsy. Imaging tests such as a chest x-ray, computed tomography (CT), magnetic resonance imaging (MRI) and positron emission topography (PET) can also be used.

Cervical Cancer Staging

Cervical cancer is staged with the FIGO (International Federation of Gynecology and Obstetrics) System of Staging—0-IV. The overall (all stages combined) 5-year survival rate for cervical cancer is about 73%.

Cervical Cancer Treatment

For pre-invasive cancer, cryosurgery, laser surgery or conisation can be used as treatment. For Stage I-IIA cervical cancer, a hysterectomy is the usual treatment. A trachelectomy may be possible in some cases. For recurrent cervical cancer, a pelvic exenteration is usually performed. Radiation therapy (either external beam radiation therapy or brachytherapy) is an option for Stage IB-Stage IV patients. Combining radiation therapy with chemotherapy has been found to be more effective than radiation therapy alone. Chemotherapeutic agents used include cisplatin, paclitaxel, topotecan, ifosfamide, and fluorouracil. Stage IVB cervical cancer is usually not considered curable but a combination of radiation therapy and chemotherapy can help relieve symptoms.

Cervical Cancer Survival by Stage

These figures come from women treated more than 10 years ago.

| Stage | 5-year survival |
| --- | --- |
| IA | Above 95% |
| IB1 | Around 90% |
| IB2 | Around 80%-85% |
| IIA/B | Around 75%-78% |
| IIIA/B | Around 47%-50% |
| IV | Around 20%-30% |

Endometrial Cancer

In the US, cancer of the endometrium is the most common cancer of the female reproductive system. There are around 39,000 new cases each year, with around 7,500 deaths. About 70% of all cases are found in women between the ages of 45 and 74.

Endometrial Cancer Diagnosis

There is no useful screening test and routine pelvic exams rarely find endometrial cancer. Most women are diagnosed when they show symptoms of the disease. An endometrial biopsy is the most commonly performed test for endometrial cancer. A hysteroscopy or dilation and curettage can also be performed. Other tests include transvaginal ultrasound or sonography and a CA 125 blood test.

Endometrial Cancer Staging

Endometrial cancer is staged using the FIGO (International Federation of Gynecology and Obstetrics) system—stages I-IV. Nearly ¾ of patients are FIGO Stage I. Overall, the 5 year survival rate for endometrial cancer is 84%. For cancer found at an early stage, the survival rate is much higher.

Endometrial Cancer Treatment

Surgery, radiation therapy, hormonal therapy and chemotherapy are used to treat endometrial cancer. Surgery by hysterectomy is the main treatment but in certain situations, a combination of treatments may be used. Chemotherapeutic agents used include doxorubicin, cisplatin and paclitaxel. The main hormone treatment for endometrial cancer uses progestins such as medroxyprogesterone acetate and megestrol acetate.

| Endometrial Cancer Survival by Stage | |
| --- | --- |
| Stage IA | 91% |
| Stage IB | 90% |
| Stage IC | 81% |
| Stage IIA | 79% |
| Stage IIB | 71% |
| Stage IIIA | 60% |
| Stage IIIB | 30% (note - may not be accurate - only a small number of patients in this group) |
| Stage IIIC | 52% |
| Stage IVA | 15% |
| Stage IVB | 17% |

Therapeutic Challenges

The major challenges in treatment of the above mentioned cancers are to improve early detection rates, to find new non-invasive markers that can be used to follow disease progression and identify relapse, and to find improved and less toxic therapies, especially for more advanced disease where 5 year survival is still poor. There is a great need to identify targets which are more specific to the cancer cells e.g. ones which are expressed on the surface of the tumour cells so that they can be attacked by promising new approaches like immunotherapeutics and targeted toxins.

SUMMARY OF THE INVENTION

The present invention provides methods and compositions for screening, diagnosis, prognosis and therapy of breast cancer, colorectal cancer, esophageal cancer, gastric cancer, prostate cancer and uterine cancer, for breast cancer, colorectal cancer, esophageal cancer, gastric cancer, prostate cancer and uterine cancer patients' stratification, for monitoring the effectiveness of breast cancer, colorectal cancer, esophageal cancer, gastric cancer, prostate cancer and uterine cancer treatment, and for drug development for treatment of breast cancer, colorectal cancer, esophageal cancer, gastric cancer, prostate cancer and uterine cancer.

We have used mass spectrometry to identify peptides generated by gel electrophoresis or tagging with ICAT reagents and tryptic digest of membrane proteins extracted from breast cancer, colorectal cancer and prostate cancer tissue samples. Peptide sequences were compared to existing protein and cDNA databases and the corresponding gene sequences identified.

The protein thus identified (matriptase) is known to undergo a series of endoproteolytic cleavages followed by activation site autocleavage resulting in a matriptase stem which remains on the cell surface and a catalytic domain of the matriptase protein which is released into the blood.

Thus, a first aspect of the invention is an agent capable of specific binding to this post-proteolytic remnant ("stem") that remains on the cell surface, or a fragment thereof, or a hybridising agent capable of hybridizing to nucleic acid encoding the matriptase stem or an agent capable of detecting the activity of the matriptase stem for use in treating, screening for, detecting and/or diagnosing disease, such as cancer, and especially breast cancer, colorectal cancer, esophageal cancer, gastric cancer, prostate cancer or uterine cancer.

Another aspect of the invention is the matriptase stem, or a fragment thereof for use in treating, screening for, detecting and/or diagnosing disease such as cancer, and especially breast cancer, colorectal cancer, esophageal cancer, gastric cancer, prostate cancer or uterine cancer.

Another aspect of the invention is an affinity reagent capable of specific binding to the matriptase stem or a fragment thereof, for example an affinity reagent which contains or is conjugated to a detectable label or contains or is conjugated to a therapeutic moiety such as a cytotoxic moiety. The affinity reagent may, for example, be an antibody.

In some embodiments, the antibody of the present invention is selected from the group consisting of: a whole antibody, an antibody fragment, a humanized antibody, a single chain antibody, an immunoconjugate, a defucosylated antibody, and a bispecific antibody. The antibody fragment may be selected from the group consisting of: a UniBody, a domain antibody, an Affibody, and a Nanobody. In some embodiments, the immunoconjugates of the invention comprise a therapeutic agent. In another aspect of the invention, the therapeutic agent is a cytotoxin or a radioactive isotope.

In some embodiments, the antibody of the present invention is selected from the group consisting of: an Affibody, a DARPin, an Anticalin, an Avimer, a Versabody, and a Duocalin.

Another aspect of the invention is a hybridizing agent capable of hybridizing to a nucleic acid encoding the matriptase stem, for example, a hybridizing agent which contains or is conjugated to a detectable label. One example of a hybridizing agent is an inhibitory RNA (RNAi). Other examples include anti-sense nucleic acid molecules including oligonucleotides and ribozymes.

The invention also provides a kit containing the matriptase stem and/or one or more fragments thereof or containing one or more aforementioned affinity reagents and/or hybridizing agents or containing one or more agents capable of detecting the activity of the matriptase stem together with instructions for their use in an aforementioned method. The kit may further contain reagents capable of detecting and reporting the binding of said affinity reagents and/or hybridizing agents to their binding partners.

Another aspect of the invention is a pharmaceutical composition comprising a therapeutically effective amount of an affinity reagent capable of specific binding to the matriptase stem or a fragment thereof.

Another aspect of the invention is a pharmaceutically acceptable diluent or carrier and a pharmaceutical composition comprising one or more affinity reagents or hybridizing reagents as aforesaid and a pharmaceutically acceptable diluent or carrier.

In some embodiments, the present invention is a method for preparing an anti-matriptase stem antibody, said method comprising the steps of: obtaining a host cell that contains one or more nucleic acid molecules encoding the antibody of the invention; growing the host cell in a host cell culture; providing host cell culture conditions wherein the one or more nucleic acid molecules are expressed; and recovering the antibody from the host cell or from the host cell culture.

Other aspects of the invention are directed to methods of making the antibodies of the invention, comprising the steps of: immunizing a transgenic animal comprising human immunoglobulin genes with a the matriptase stem peptide; recovering B-cells from said transgenic animal; making hybridomas from said B-cells; selecting hybridomas that express antibodies that bind the matriptase stem; and recovering said antibodies that bind the matriptase stem from said selected hybridomas.

In other embodiments, the method of making anti-matriptase stem antibodies, comprises the steps of:

immunizing a transgenic animal comprising human immunoglobulin genes with a peptide of the matriptase stem;

recovering mRNA from the B cells of said transgenic animal;

converting said mRNA to cDNA;

expressing said cDNA in phages such that anti-matriptase stem antibodies encoded by said cDNA are presented on the surface of said phages;

selecting phages that present anti-matriptase stem antibodies;

recovering nucleic acid molecules from said selected phages that encode said anti-matriptase stem antibodies;

expressing said recovered nucleic acid molecules in a host cell; and recovering antibodies from said host cell that bind to matriptase stem proteins.

Another aspect of the invention provides use of a matriptase stem polypeptide, one or more immunogenic fragments or derivatives thereof for the treatment or prophylaxis of breast cancer, colorectal cancer, esophageal cancer, gastric cancer, prostate cancer or uterine cancer.

Another aspect of the invention provides methods of treating breast cancer, colorectal cancer, esophageal cancer, gastric cancer, prostate cancer or uterine cancer, comprising administering to a patient a therapeutically effective amount of an antibody or other affinity reagent capable of immunospecific binding to the matriptase stem.

Another aspect of the invention provides a method of determining the availability of the matriptase stem as a therapeutic target in a subject, the method comprising:

(a) performing assays configured to detect the soluble catalytic domain of the protein of the invention in one or more samples obtained from said subject; and
(b) correlating the results of said assay(s) to the presence or absence of the matriptase stem.

Suitably such a method involves determining that when the level of said detected catalytic domain of the protein of the invention is higher in the subject than a control level, said determination indicates the availability of the matriptase stem as a therapeutic target.

In another aspect the invention provides methods of treating breast cancer, colorectal cancer, esophageal cancer, gastric cancer, prostate cancer and uterine cancer, comprising administering to a patient a therapeutically effective amount of a compound that modulates (e.g. upregulates or downregulates) or complements the expression or the biological activity (or both) of the matriptase stem in patients having breast cancer, colorectal cancer, esophageal cancer, gastric cancer, prostate cancer or uterine cancer, in order to (a) prevent the onset or development of breast cancer, colorectal cancer, esophageal cancer, gastric cancer, prostate cancer or uterine cancer; (b) prevent the progression of breast cancer, colorectal cancer, esophageal cancer, gastric cancer, prostate cancer or uterine cancer; or (c) ameliorate the symptoms of breast cancer, colorectal cancer, esophageal cancer, gastric cancer, prostate cancer or uterine cancer.

According to another aspect of the invention we provide a method of detecting, diagnosing and/or screening for or monitoring the progression of breast cancer, colorectal cancer, esophageal cancer, gastric cancer, prostate cancer or uterine cancer or of monitoring the effect of an anti-breast cancer, anti-colorectal cancer, anti-esophageal cancer, anti-gastric cancer, anti-prostate cancer or anti-uterine cancer drug or therapy in a subject which comprises detecting the presence or level of the matriptase stem, or one or more fragments thereof, or the presence or level of nucleic acid encoding the matriptase stem or the presence or level of the activity of the matriptase stem or which comprises detecting a change in the level thereof in said subject.

According to another aspect of the invention we provide a method of detecting, diagnosing and/or screening for breast cancer, colorectal cancer, esophageal cancer, gastric cancer, prostate cancer or uterine cancer in a candidate subject which comprises detecting the presence of the matriptase stem, or one or more fragments thereof, or the presence of nucleic acid encoding the matriptase stem or the presence of the activity of the matriptase stem in said candidate subject, in which either (a) the presence of an elevated level of the matriptase stem or said one or more fragments thereof or an elevated level of nucleic acid encoding the matriptase stem or the presence of an elevated level of the activity of the matriptase stem in the candidate subject as compared with the level in a healthy subject or (b) the presence of a detectable level of the matriptase stem or said one or more fragments thereof or a detectable level of nucleic acid encoding the matriptase stem or the presence of a detectable level of the activity of the matriptase stem in the candidate subject as compared with a corresponding undetectable level in a healthy subject indicates the presence of breast cancer, colorectal cancer, esophageal cancer, gastric cancer, prostate cancer or uterine cancer in said subject.

According to another aspect of the invention we provide a method of monitoring the progression of breast cancer, colorectal cancer, esophageal cancer, gastric cancer, prostate cancer or uterine cancer in a subject or of monitoring the effect of an anti-breast cancer, anti-colorectal cancer, anti-esophageal cancer, anti-gastric cancer, anti-prostate cancer or anti-uterine cancer drug or therapy which comprises detecting the presence of the matriptase stem, or one or more fragments thereof, or the presence of nucleic acid encoding the matriptase stem or the presence of the activity of the matriptase stem in said candidate subject at a first time point and at a later time point, the presence of an elevated or lowered level of the matriptase stem or said one or more fragments thereof or an elevated or lowered level of nucleic acid encoding the matriptase stem or the presence of an elevated or lowered level of the activity of the matriptase stem in the subject at the later time point as compared with the level in the subject at said first time point, indicating the progression or regression of breast cancer, colorectal cancer, esophageal cancer, gastric cancer, prostate cancer or uterine cancer or indicating the effect or non-effect of an anti-breast cancer, anti-colorectal cancer, anti-esophageal cancer, anti-gastric cancer, anti-prostate cancer or anti-uterine cancer drug or therapy in said subject.

The presence of the matriptase stem, or one or more fragments thereof, or the presence of nucleic acid encoding the matriptase stem or the presence of the activity of the matriptase stem may, for example, be detected by analysis of a biological sample obtained from said subject.

The method of invention may typically include the step of obtaining a biological sample for analysis from said subject.

The biological sample used can be from any source such as a tissue sample, e.g. breast, colorectal, esophageal, gastric, prostate or uterine tissue. For instance, when looking for evidence of metastatic breast cancer, colorectal cancer, esophageal cancer, gastric cancer, prostate cancer or uterine cancer, one would look at major sites of breast cancer, colorectal cancer, esophageal cancer, gastric cancer, prostate cancer or uterine cancer metastasis, e.g. the liver, lungs and bones for breast cancer; the liver, peritoneal cavity, pelvis, retroperitoneum and lungs for colorectal cancer; the trachea, liver, bones and brain for esophageal cancer; the liver, lungs, brain and bones for gastric cancer; the bladder, rectum and bones for prostate cancer and the bladder, rectum, lungs, liver, bones and brain for uterine cancer.

Alternatively the presence of the matriptase stem, or one or more fragments thereof, or the presence of nucleic acid encoding the matriptase stem or the presence of the activity of the matriptase stem may be detected by analysis in situ.

In certain embodiments, methods of diagnosis described herein may be at least partly, or wholly, performed in vitro.

Suitably the presence of the matriptase stem, or one or more fragments thereof, or the presence of nucleic acid encoding the matriptase stem or the presence of the activity of the matriptase stem is detected quantitatively.

For example, quantitatively detecting may comprise:
(a) contacting a biological sample with an affinity reagent that is specific for the matriptase stem, said affinity reagent optionally being conjugated to a detectable label; and
(b) detecting whether binding has occurred between the affinity reagent and at least one species in the sample, said detection being performed either directly or indirectly.

Alternatively the presence of the matriptase stem, or one or more fragments thereof, or the presence of nucleic acid encoding the matriptase stem or the presence of the activity of the matriptase stem may be detected quantitatively by means involving use of an imaging technology.

In another embodiment, the method of the invention involves use of immunohistochemistry on breast, colorectal, esophageal, gastric, prostate or uterine tissue sections in order to determine the presence of the matriptase stem, or one or more fragments thereof, or the presence of nucleic acid encoding the matriptase stem or the presence of the activity of the matriptase stem, and thereby to localise breast cancer, colorectal cancer, esophageal cancer, gastric cancer, prostate cancer or uterine cancer cells.

In one embodiment the presence of the matriptase stem or one or more epitope-containing fragments thereof is detected, for example using an affinity reagent capable of specific binding to the matriptase stem or one or more fragments thereof, such as an antibody.

In another embodiment the activity of the matriptase stem is detected.

According to another aspect of the invention there is provided a method of detecting, diagnosing and/or screening for or monitoring the progression of breast cancer, colorectal cancer, esophageal cancer, gastric cancer, prostate cancer or uterine cancer or of monitoring the effect of an anti-breast cancer, anti-colorectal cancer, anti-esophageal cancer, anti-gastric cancer, anti-prostate cancer or anti-uterine cancer drug or therapy in a subject which comprises detecting the presence or level of antibodies capable of immunospecific binding to the matriptase stem, or one or more epitope-containing fragments thereof or which comprises detecting a change in the level thereof in said subject.

According to another aspect of the invention there is also provided a method of detecting, diagnosing and/or screening for breast cancer, colorectal cancer, esophageal cancer, gastric cancer, prostate cancer or uterine cancer in a subject which comprises detecting the presence of antibodies capable of immunospecific binding to the matriptase stem, or one or more epitope-containing fragments thereof in said subject, in which (a) the presence of an elevated level of antibodies capable of immunospecific binding to the matriptase stem or said one or more epitope-containing fragments thereof in said subject as compared with the level in a healthy subject or (b) the presence of a detectable level of antibodies capable of immunospecific binding to the matriptase stem or said one or more epitope-containing fragments thereof in said subject as compared with a corresponding undetectable level in a healthy subject indicates the presence of breast cancer, colorectal cancer, esophageal cancer, gastric cancer, prostate cancer or uterine cancer in said subject.

One particular method of detecting, diagnosing and/or screening for breast cancer, colorectal cancer, esophageal cancer, gastric cancer, prostate cancer or uterine cancer comprises:
 (a) bringing into contact with a biological sample to be tested the matriptase stem, or one or more epitope-containing fragments thereof; and
 (b) detecting the presence of antibodies in the subject capable of immunospecific binding to the matriptase stem, or one or more epitope-containing fragments thereof.

According to another aspect of the invention there is provided a method of monitoring the progression of breast cancer, colorectal cancer, esophageal cancer, gastric cancer, prostate cancer or uterine cancer or of monitoring the effect of an anti-breast cancer, anti-colorectal cancer, anti-esophageal cancer, anti-gastric cancer, anti-prostate cancer or anti-uterine cancer drug or therapy in a subject which comprises detecting the presence of antibodies capable of immunospecific binding to the matriptase stem, or one or more epitope-containing fragments thereof in said subject at a first time point and at a later time point, the presence of an elevated or lowered level of antibodies capable of immunospecific binding to the matriptase stem, or one or more epitope-containing fragments thereof in said subject at the later time point as compared with the level in said subject at said first time point, indicating the progression or regression of breast cancer, colorectal cancer, esophageal cancer, gastric cancer, prostate cancer or uterine cancer or the effect or non-effect of an anti-breast cancer, anti-colorectal cancer, anti-esophageal cancer, anti-gastric cancer, anti-prostate cancer or anti-uterine cancer drug or therapy in said subject.

The presence of antibodies capable of immunospecific binding to the matriptase stem, or one or more epitope-containing fragments thereof is typically detected by analysis of a biological sample obtained from said subject (exemplary biological samples are mentioned above, e.g. the sample is a sample of breast, colorectal, esophageal, gastric, prostate or uterine tissue, or else a sample of blood or saliva).

The method typically includes the step of obtaining said biological sample for analysis from said subject.

The antibodies that may be detected include IgA, IgM and IgG antibodies.

In any of the above methods, the level that may be detected in the candidate subject who has breast cancer, colorectal cancer, esophageal cancer, gastric cancer, prostate cancer or uterine cancer is 2 or more fold higher than the level in the healthy subject.

In one embodiment, cancer is detected, prevented or treated. In another embodiment, cancer is treated using an affinity reagent that recognizes the matriptase stem. In another embodiment, the affinity reagent is an antibody or a binding portion thereof, a humanized antibody, a single chain antibody, an immunoconjugate, a defucosylated antibody, and a bispecific antibody, a UniBody, a domain antibody, an Affibody, a Nanobody, a DARPin, an Anticalin, an Avimer, a Versabody, or a Duocalin. In another embodiment, the cancer is a breast cancer, a colorectal cancer, an esophageal cancer, a gastric cancer, a prostate cancer, or a uterine cancer.

Other aspects of the present invention are set out below and in the claims herein.

BRIEF DESCRIPTION OF THE FIGURES

FIG. 1 shows the amino acid sequence of the protein of the invention. The tryptic peptides detected experimentally by mass spectrometry are highlighted—mass matched peptides are shown in bold, peptides sequenced by tandem mass spectrometry are underlined.

FIGS. 2a-2d show the four possible sequences of the matriptase stem and also show the cleavage sites. In each figure, the sequence of the stem is shown in bold and the cleavage site (if any) is shown in underline.

FIG. 3 shows the sequence of the soluble catalytic domain of the protein of the invention. The sequence of the catalytic domain is shown in bold and the cleavage site is shown in underline.

FIG. 4 shows the sequence of the fusion protein of the matriptase stem—hFcG1. The stem of the human protein of the invention is shown in bold, the human FcG1 region is shown in italics and the Factor Xa cleavage recognition site is underlined.

DETAILED DESCRIPTION OF THE INVENTION

Figure 5:
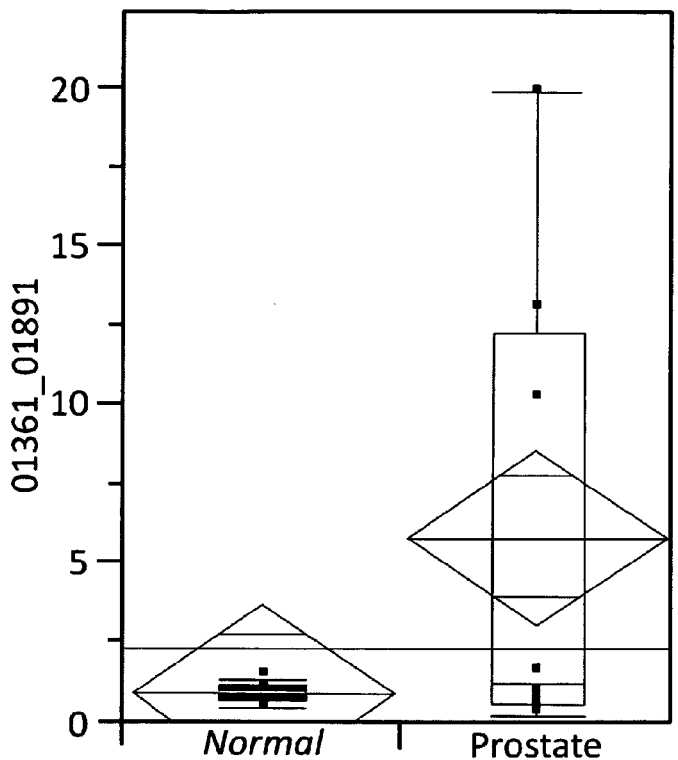
FIG. 5 shows Box plot data for the catalytic domain of the protein of the invention in prostate cancer.

The invention described in detail below encompasses the administration of therapeutic compositions to a mammalian subject to treat or prevent breast cancer, colorectal cancer, esophageal cancer, gastric cancer, prostate cancer or uterine cancer. The invention also provides methods and compositions for clinical screening, diagnosis, prognosis of breast cancer, colorectal cancer, esophageal cancer, gastric cancer, prostate cancer or uterine cancer in a mammalian subject, for identifying patients most likely to respond to a particular therapeutic treatment, for monitoring the results of breast cancer, colorectal cancer, esophageal cancer, gastric cancer, prostate cancer or uterine cancer therapy, for drug screening and drug development.

In one aspect the invention provides an agent capable of specific binding to the matriptase stem, or a fragment thereof, or a hybridising agent capable of hybridizing to nucleic acid encoding the matriptase stem or an agent capable of detecting the activity of the matriptase stem for use in treating, screening for, detecting and/or diagnosing disease, such as cancer, and especially breast cancer, colorectal cancer, esophageal cancer, gastric cancer, prostate cancer or uterine cancer.

Another aspect of the invention is an affinity reagent capable of specific binding to the matriptase stem or a fragment thereof, for example an affinity reagent which contains or is conjugated to a detectable label or contains or is conjugated to a therapeutic moiety such as a cytotoxic moiety. The affinity reagent may, for example, be an antibody.

Another aspect of the invention is a pharmaceutical composition comprising a therapeutically effective amount of an affinity reagent capable of specific binding to the matriptase stem or a fragment thereof.

In another aspect the invention provides use of a polypeptide of the matriptase stem, or one or more fragments or derivatives thereof, for the treatment or prophylaxis of breast cancer, colorectal cancer, esophageal cancer, gastric cancer, prostate cancer or uterine cancer.

The invention also provides use of a polypeptide of the matriptase stem, one or more fragments or derivatives thereof in the manufacture of a medicament for the treatment or prophylaxis of breast cancer, colorectal cancer, esophageal cancer, gastric cancer, prostate cancer or uterine cancer.

In one aspect there is provided a method of treatment comprising administering a therapeutically effective amount of a polypeptide of the matriptase stem, one or more fragments or derivatives thereof, or one or more fragments or derivatives thereof, for the treatment or prophylaxis of breast cancer, colorectal cancer, esophageal cancer, gastric cancer, prostate cancer or uterine cancer.

The invention further provides a method for the treatment or prophylaxis of breast cancer, colorectal cancer, esophageal cancer, gastric cancer, prostate cancer or uterine cancer in a subject, or of vaccinating a subject against breast cancer, colorectal cancer, esophageal cancer, gastric cancer, prostate cancer or uterine cancer, which comprises the step of administering to the subject an effective amount of a polypeptide of the matriptase stem and/or one or more antigenic or immunogenic fragments thereof, for example as a vaccine.

The mammalian subject may be a non-human mammal, but is preferably human, more preferably a human adult, i.e. a human subject at least 21 (more preferably at least 35, at least 50, at least 60, at least 70, or at least 80) years old.

In one aspect there is provided a composition capable of eliciting an immune response in a subject, which composition comprises a polypeptide of the matriptase stem and/or one or more antigenic or immunogenic fragments thereof, and one or more suitable adjuvants (suitable adjuvants are discussed below).

The composition capable of eliciting an immune response may for example be provided as a vaccine comprising a polypeptide of the matriptase stem or derivatives thereof, and/or one or more antigenic or immunogenic fragments thereof.

In one aspect of the invention, the matriptase stem is provided as an antigen that is a fusion protein with a heterologous peptide moiety.

In one embodiment, the matriptase stem, or a matriptase stem/fusion protein, is presented on the surface of a cell and used as an antigen. In another embodiment, the fusion protein contains a heterologous transmembrane domain. In a preferred embodiment, the transmembrane domain is an immunoglobulin transmembrane domain. In another preferred embodiment, the transmembrane domain is an IgG transmembrane domain.

For clarity of disclosure, and not by way of limitation, the invention will be described with respect to the analysis of breast, colorectal, esophageal, gastric, prostate and uterine tissue. However, as one skilled in the art will appreciate, the assays and techniques described below can be applied to other types of patient samples, including a tissue sample from a patient at risk of having breast cancer, colorectal cancer, esophageal cancer, gastric cancer, prostate cancer and uterine cancer (e.g. a biopsy such as a breast, colon, esophagus, stomach, prostate or uterus biopsy) or homogenate thereof. The methods and compositions of the present invention are specially suited for screening, diagnosis and prognosis of a living subject, but may also be used for postmortem diagnosis in a subject, for example, to identify family members at risk of developing the same disease.

Matriptase Stem

In one aspect of the invention, one-dimensional electrophoresis, isotope-coded affinity tags (ICAT) or another appropriate method are used to analyse breast cancer, colorectal cancer, esophageal cancer, gastric cancer, prostate cancer or uterine cancer tissue samples from a subject, preferably a living subject, in order to measure the expression of the matriptase stem for screening or diagnosis of breast cancer, colorectal cancer, esophageal cancer, gastric cancer, prostate cancer or uterine cancer, to determine the prognosis of a breast cancer, colorectal cancer, esophageal cancer, gastric cancer, prostate cancer or uterine cancer patient, to monitor the effectiveness of breast cancer, colorectal cancer, esophageal cancer, gastric cancer, prostate cancer or uterine cancer therapy, or for drug development.

As used herein, the term "Protein of the invention", or "matriptase", refers to the protein illustrated in FIG. 1 detected experimentally by 1D electrophoresis of breast and colorectal tissue samples and ICAT analysis of prostate tissue samples. Protein derivatives of these sequences may also be useful for the same purposes as described herein.

This protein has been identified in membrane protein extracts of breast, colorectal and prostate tissue samples from breast cancer, colorectal cancer and prostate cancer patients, through the methods and apparatus of the Preferred Technologies described in Examples 1 and 2 (1D gel electrophoresis or ICAT, together with tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at www.expasy.com), and the following entry: Q9Y5Y6, Suppressor of tumorigenicity protein 14, was identified.

Suppressor of tumorigenicity protein 14 degrades extracellular matrix. According to SWISS-PROT, it is proposed to play a role in breast cancer invasion and metastasis. It exhibits trypsin-like activity as defined by cleavage of synthetic substrates with Arg or Lys as the P1 site. It has an essential physiological role in profilaggrin processing, corneocyte maturation and lipid matrix formation associated with terminal differentiation of the oral epithelium and the epidermis and is also critical for hair follicle growth. It is a type II transmembrane serine protease expressed in most human epithelia and it is a strictly epithelial protease. It is expressed in carcinomas of epithelial origin and not in tumours of mesenchymal origin.

The protein has also been described in US2006/0171884 (where it is referred to as "matriptase"). Antibodies raised against the catalytic domain of matriptase are also described, and are indicated for the treatment of cancer. The protein has also been described in WO2007/141280 which is herein incorporated by reference in its entirety. Methods and compositions for screening, diagnosis and prognosis of colorectal cancer are described.

The extracellular stem region of matriptase has been reported to consist of a single SEA domain comprising amino acid residues 86-201 (See FIG. 2(a), matriptase Stem Sequence A, SEQ ID No: 10). Activation of matriptase requires sequential endoproteolytic cleavages and activation site autocleavage. Cleavage occurs after amino acid Gly149, resulting in a stem region comprising amino acid residues 86-149 (See FIG. 2(b), matriptase Stem Sequence B, SEQ ID No: 11). Further proteolytic cleavage can occur after amino acid K189, which results in a stem region comprising amino acid sequences 86-189 (See FIG. 2(c), matriptase Stem Sequence C, SEQ ID No: 12) or amino acid K204, which results in a stem region comprising amino acid sequences 86-204 (See FIG. 2(d), matriptase Stem Sequence D, SEQ ID No: 13). matriptase is then converted into its active conformation by proteolytic cleavage after Arg614. The catalytic C-terminal serine protease domain consists of amino acid residues 615-855 (See FIG. 3, SEQ ID No: 14). See, for example, matriptase: Potent Proteolysis on the Cell Surface; List, Bugge and Szabo; Mol Med 12(1-3)1-7, January-March 2006 and Regulation of the activity of matriptase on epithelial cell surfaces by a blood derived factor; Benaud, Dickson and Lin; Eur J Biochem 268, 1439-1447, 2001 which are herein incorporated in their entirety.

Activation of matriptase leads to auto-catalytic release of catalytic reagents in blood. The catalytic domain of matriptase (as defined by SEQ ID No: 14) can be assayed by any method known to those skilled in the art, including but not limited to, the technology described herein in Examples 5 and 6, kinase assays, enzyme assays, binding assays and other functional assays, immunoassays, and western blotting.

Thus, detection of the matriptase stem (for example using the assay described in Example 4) and also detecting the soluble catalytic domain of matriptase (for example using the assays described in Examples 5 and 6) in a sample obtained from a subject would demonstrate that cleavage of matriptase had occurred and would indicate availability of the stem region of matriptase as a therapeutic target in that subject. There is a concordance of data between the results of the immunohistochemistry assay to detect the matriptase stem in Example 4 and the results of the assays to detect the soluble catalytic domain of matriptase in Examples 5 and 6, indicating that this approach is viable.

The matriptase stem is useful as are fragments particularly epitope containing fragments e.g. antigenic or immunogenic fragments thereof and derivatives thereof. Epitope containing fragments including antigenic or immunogenic fragments will typically be of length 12 amino acids or more e.g. 20 amino acids or more e.g. 50 or 100 amino acids or more. Fragments may be 95% or more of the length of the full stem of the protein e.g. 90% or more e.g. 75% or 50% or 25% or 10% or more of the length of the full stem of the protein.

Alternatively, the protein/polypeptide employed or referred to herein may be limited to those specifically recited/described in the present specification or a moiety 80, 85, 90, 91, 92, 93, 94, 95, 96, 97, 98 or 99% identical or similar thereto.

Epitope containing fragments including antigenic or immunogenic fragments will be capable of eliciting a relevant immune response in a patient. DNA encoding the matriptase stem is also useful as are fragments thereof e.g. DNA encoding fragments of the matriptase stem such as immunogenic fragments thereof. Fragments of nucleic acid (e.g. DNA) encoding the matriptase stem may be 95% or more of the length of the full coding region e.g. 90% or more e.g. 75% or 50% or 25% or 10% or more of the length of the full coding region. Fragments of nucleic acid (e.g. DNA) may be 36 nucleotides or more e.g. 60 nucleotides or more e.g. 150 or 300 nucleotides or more in length.

Derivatives of the matriptase stem include variants on the sequence in which one or more (e.g. 1-20 such as 15 amino acids, or up to 20% such as up to 10% or 5% or 1% by number of amino acids based on the total length of the stem of the protein) deletions, insertions or substitutions have been made. Substitutions may typically be conservative substitutions. Derivatives will typically have essentially the same biological function as the protein from which they are derived. Derivatives will typically be comparably antigenic or immunogenic to the protein from which they are derived. Derivatives will typically have either the ligand-binding activity, or the active receptor-complex forming ability, or preferably both, of the protein from which they are derived.

Derivatives of proteins also include chemically treated protein such as carboxymethylated, carboxyamidated, acetylated proteins, for example treated during purification.

Tables 1a and 1b below illustrate the different occurrences of matriptase as detected by 1D gel electrophoresis and mass spectrometry of membrane protein extracts of breast and colorectal tissue samples from breast cancer and colorectal cancer patients respectively. The first left hand column provides the molecular weight and the right hand column provides a list of the sequences observed by mass spectrometry and the corresponding SEQ ID Nos.

Table 2 below illustrates the different occurrences of matriptase as detected by ICAT and mass spectrometry of membrane protein extracts of prostate tissue samples from prostate cancer patients. The left hand column provides the sample number and the right hand column provides a list of the sequences observed by mass spectrometry and the corresponding SEQ ID Nos.

TABLE 1a

Breast cancer 1D GE

| MW (Da) | Tryptics identified [SEQ ID No] |
|---|---|
| 59316 | SQFVVTSNSNK [8] |
| 62727 | FTTPGFPDSPYPAHAR [2], GDADSVLSLTFR [3], HPGFEATFFQLPR [4], SAPGVQERR [6] |

TABLE 1b

Colorectal cancer 1D GE

| MW (Da) | Tryptics identified [SEQ ID No] |
|---|---|
| 74658 | FTTPGFPDSPYPAHAR [2], GDADSVLSLTFR [3], SFVVTSVVAFPTDSK [7] |
| 76173 | FTTPGFPDSPYPAHAR [2], GDADSVLSLTFR [3], HPGFEATFFQLPR [4], IFQAGVVSWGDGCAQR [5] |
| 77754 | FTTPGFPDSPYPAHAR [2] |

TABLE 2

Prostate cancer ICAT

| Sample | Tryptics identified [SEQ ID No] |
|---|---|
| Sample 1 | TQDNSCSFGLHAR [9] |
| Sample 2 | TQDNSCSFGLHAR [9] |
| Sample 3 | TQDNSCSFGLHAR [9] |

For the matriptase stem, the detected level obtained upon analysing tissue from subjects having breast cancer, colorectal cancer, esophageal cancer, gastric cancer, prostate cancer or uterine cancer relative to the detected level obtained upon analysing tissue from subjects free from breast cancer, colorectal cancer, esophageal cancer, gastric cancer, prostate cancer and uterine cancer will depend upon the particular analytical protocol and detection technique that is used. Accordingly, the present invention contemplates that each laboratory will establish a reference range in subjects free from breast cancer, colorectal cancer, esophageal cancer, gastric cancer, prostate cancer and uterine cancer according to the analytical protocol and detection technique in use, as is conventional in the diagnostic art. Preferably, at least one control positive tissue sample from a subject known to have breast cancer, colorectal cancer, esophageal cancer, gastric cancer, prostate cancer or uterine cancer or at least one control negative tissue sample from a subject known to be free from breast cancer, colorectal cancer, esophageal cancer, gastric cancer, prostate cancer and uterine cancer (and more preferably both positive and negative control samples) are included in each batch of test samples analysed.

The matriptase stem can be used for detection, prognosis, diagnosis, or monitoring of breast cancer, colorectal cancer, esophageal cancer, gastric cancer, prostate cancer and uterine cancer or for drug development. In one embodiment of the invention, tissue from a subject (e.g. a subject suspected of having breast cancer, colorectal cancer, esophageal cancer, gastric cancer, prostate cancer or uterine cancer) is analysed by 1D electrophoresis or ICAT for detection of only those peptides specific to the matriptase stem, consisting of those peptides contained in any one of the sequences defined by SEQ ID Nos: 10-13. Preferably, one of the peptides detected is the peptide defined by SEQ ID No: 7. An increased abundance of the matriptase stem in the tissue from the subject relative to tissue from a subject or subjects free from breast cancer, colorectal cancer, esophageal cancer, gastric cancer, prostate cancer and uterine cancer (e.g. a control sample) or a previously determined reference range indicates the presence of breast cancer, colorectal cancer, esophageal cancer, gastric cancer, prostate cancer or uterine cancer.

The sequences shown in Tables 1-2 may be employed in any relevant aspect of the invention.

In relation to variants, fragments, immunogenic fragments or antigenic fragments of matriptase:
for colorectal cancer applications: preferably these comprise the sequence defined by SEQ ID No: 7.

As used herein, the matriptase stem is "isolated" when it is present in a preparation that is substantially free of contaminating proteins, i.e., a preparation in which less than 10% (preferably less than 5%, more preferably less than 1%) of the total protein present is contaminating protein(s). A contaminating protein is a protein having a significantly different amino acid sequence from that of isolated stem of matriptase, as determined by mass spectral analysis. As used herein, a "significantly different" sequence is one that permits the contaminating protein to be resolved from the matriptase stem by mass spectral analysis, performed according to the Reference Protocols in Examples 1 and 2.

Thus in one aspect the invention provides a pharmaceutical composition for the treatment of breast cancer, colorectal cancer, esophageal cancer, gastric cancer, prostate cancer or uterine cancer comprising a therapeutically effective amount of a polypeptide of the matriptase stem (particularly those defined above) or an immunogenic fragment thereof and an adjuvant.

The matriptase stem can be assayed by any method known to those skilled in the art, including but not limited to, the Preferred Technologies described herein, kinase assays, enzyme assays, binding assays and other functional assays, immunoassays, and western blotting. In one embodiment, the matriptase stem is separated on a 1-D gel by virtue of its MW and visualized by staining the gel. In one embodiment, matriptase is stained with a fluorescent dye and imaged with a fluorescence scanner. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety. In another embodiment, the matriptase stem is analysed using isotope-coded affinity tags (ICAT).

Alternatively, the matriptase stem can be detected in an immunoassay. In one embodiment, an immunoassay is performed by contacting a sample from a subject to be tested with an anti-matriptase stem antibody (or other affinity reagent) under conditions such that binding (e.g. immunospecific binding) can occur if the matriptase stem is present, and detecting or measuring the amount of any binding (e.g. immunospecific binding) by the binding agent. Stem of matriptase binding agents can be produced by the methods and techniques taught herein.

The matriptase stem may be detected by virtue of the detection of a fragment thereof e.g. an epitope containing (e.g. an immunogenic or antigenic) fragment thereof. Fragments may have a length of at least 10, more typically at least 20 amino acids e.g. at least 50 or 100 amino acids.

In one embodiment, binding of an affinity reagent (e.g. an antibody) in tissue sections can be used to detect aberrant stem of matriptase localization or an aberrant level of the matriptase stem. In a specific embodiment, an antibody (or other affinity reagent) to the matriptase stem can be used to assay a patient tissue (e.g. breast, colorectal, esophageal, gastric, prostate or uterine tissue) for the level of the matriptase stem where an aberrant level of the matriptase stem is indicative of breast cancer, colorectal cancer, esophageal cancer, gastric cancer, prostate cancer or uterine cancer. As used herein, an "aberrant level" means a level that is increased compared with the level in a subject free from breast cancer, colorectal cancer, esophageal cancer, gastric cancer, prostate cancer and uterine cancer or a reference level.

Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

If desired, a gene encoding the matriptase stem, a related gene, or related nucleic acid sequences or subsequences, including complementary sequences, can also be used in hybridization assays. A nucleotide encoding the matriptase stem, or subsequences thereof comprising at least 8 nucleotides, preferably at least 12 nucleotides, and most preferably at least 15 nucleotides can be used as a hybridization probe. Hybridization assays can be used for detection, prognosis, diagnosis, or monitoring of conditions, disorders, or disease states, associated with aberrant expression of the gene encoding the matriptase stem, or for differential diagnosis of subjects with signs or symptoms suggestive of breast cancer, colorectal cancer, esophageal cancer, gastric cancer, prostate cancer or uterine cancer. In particular, such a hybridization assay can be carried out by a method comprising contacting a subject's sample containing nucleic acid with a nucleic acid probe capable of hybridizing to a DNA or RNA that encodes the matriptase stem, under conditions such that hybridization can occur, and detecting or measuring any resulting hybridization.

Hence nucleic acid encoding the matriptase stem (e.g. DNA or more suitably RNA) may be detected, for example, using a hybridizing agent capable of hybridizing to nucleic acid encoding the stem of matriptase.

One such exemplary method comprises:
(a) contacting one or more oligonucleotide probes comprising 10 or more consecutive nucleotides complementary to a nucleotide sequence encoding the stem of matriptase, with an RNA obtained from a biological sample from the subject or with cDNA copied from the RNA, wherein said contacting occurs under conditions that permit hybridization of the probe to the nucleotide sequence if present;
(b) detecting hybridization, if any, between the probe and the nucleotide sequence; and
(c) comparing the hybridization, if any, detected in step (b) with the hybridization detected in a control sample, or with a previously determined reference range.

The invention also provides diagnostic kits, comprising an anti-matriptase stem antibody (or other affinity reagent). In addition, such a kit may optionally comprise one or more of the following: (1) instructions for using the anti-matriptase stem affinity reagent for diagnosis, prognosis, therapeutic monitoring or any combination of these applications; (2) a labeled binding partner to the affinity reagent; (3) a solid phase (such as a reagent strip) upon which the anti-matriptase stem affinity reagent is immobilized; and (4) a label or insert indicating regulatory approval for diagnostic, prognostic or therapeutic use or any combination thereof. If no labeled binding partner to the affinity reagent is provided, the anti-matriptase affinity reagent itself can be labeled with a detectable marker, e.g. a chemiluminescent, enzymatic, fluorescent, or radioactive moiety.

The invention also provides a kit comprising a nucleic acid probe capable of hybridizing to nucleic acid, suitably RNA encoding the matriptase stem. In a specific embodiment, a kit comprises in one or more containers a pair of primers (e.g. each in the size range of 6-30 nucleotides, more preferably 10-30 nucleotides and still more preferably 10-20 nucleotides) that under appropriate reaction conditions can prime amplification of at least a portion of a nucleic acid encoding the matriptase stem, such as by polymerase chain reaction (see e.g. Innis et al., 1990, PCR Protocols, Academic Press, Inc., San Diego, Calif.), ligase chain reaction (see EP 320, 308) use of Qβ replicase, cyclic probe reaction, or other methods known in the art.

A kit can optionally further comprise a predetermined amount of the matriptase stem or a nucleic acid encoding the matriptase stem, e.g. for use as a standard or control.

Use in Clinical Studies

The diagnostic methods and compositions of the present invention can assist in monitoring a clinical study, e.g. to evaluate drugs for therapy of breast cancer, colorectal cancer, esophageal cancer, gastric cancer, prostate cancer or uterine cancer. In one embodiment, candidate molecules are tested for their ability to restore the matriptase stem levels in a subject having breast cancer, colorectal cancer, esophageal cancer, gastric cancer, prostate cancer or uterine cancer to levels found in subjects free from breast cancer, colorectal cancer, esophageal cancer, gastric cancer, prostate cancer and uterine cancer or, in a treated subject, to preserve the matriptase stem levels at or near non-breast cancer, non-colorectal cancer, non-esophageal cancer, non-gastric cancer, non-prostate cancer or non-uterine cancer values.

In another embodiment, the methods and compositions of the present invention are used to screen candidates for a clinical study to identify individuals having breast cancer, colorectal cancer, esophageal cancer, gastric cancer, prostate cancer or uterine cancer; such individuals can then be excluded from the study or can be placed in a separate cohort for treatment or analysis.

Production of the Matriptase Stem and Corresponding Nucleic Acid

In one aspect the invention provides a method of treating or preventing breast cancer, colorectal cancer, esophageal cancer, gastric cancer, prostate cancer or uterine cancer, comprising administering to a subject in need of such treatment or prevention a therapeutically effective amount of nucleic acid encoding the matriptase stem or one or more fragments or derivatives thereof, for example in the form of a vaccine.

In another aspect there is provided a method of treating or preventing breast cancer, colorectal cancer, esophageal cancer, gastric cancer, prostate cancer or uterine cancer comprising administering to a subject in need of such treatment or prevention a therapeutically effective amount of nucleic acid that inhibits the function or expression of the stem of matriptase.

The methods (and/or other DNA aspects disclosed herein) of the invention may, for example include wherein the nucleic acid is a matriptase stem anti-sense nucleic acid or ribozyme.

Thus the invention includes the use of nucleic acid encoding the matriptase stem or one or more fragments or derivatives thereof, in the manufacture of a medicament for treating or preventing breast cancer, colorectal cancer, esophageal cancer, gastric cancer, prostate cancer or uterine cancer.

There is also provided the use of nucleic acid that inhibits the function or expression of the matriptase stem in the manufacture of a medicament for treating or preventing breast cancer, colorectal cancer, esophageal cancer, gastric cancer, prostate cancer or uterine cancer.

A DNA employed in the present invention can be obtained by isolation as a cDNA fragment from cDNA libraries using as starter materials commercial mRNAs and determining and identifying the nucleotide sequences thereof. That is, specifically, clones are randomly isolated from cDNA libraries, which are prepared according to Ohara et al's method (DNA Research Vol. 4, 53-59 (1997)). Next, through hybridization, duplicated clones (which appear repeatedly) are removed and then in vitro transcription and translation are carried out. Nucleotide sequences of both termini of clones, for which products of 50 kDa or more are confirmed, are determined Furthermore, databases of known genes are searched for homology using the thus obtained terminal nucleotide sequences as queries.

In addition to the above screening method, the 5' and 3' terminal sequences of cDNA are related to a human genome sequence. Then an unknown long-chain gene is confirmed in a region between the sequences, and the full-length of the cDNA is analyzed. In this way, an unknown gene that is unable to be obtained by a conventional cloning method that depends on known genes can be systematically cloned.

Moreover, all of the regions of a human-derived gene containing a DNA of the present invention can also be prepared using a PCR method such as RACE while paying sufficient attention to prevent artificial errors from taking place in short fragments or obtained sequences. As described above, clones having DNA of the present invention can be obtained.

In another means for cloning DNA of the present invention, a synthetic DNA primer having an appropriate nucleotide sequence of a portion of a polypeptide of the present invention is produced, followed by amplification by the PCR method using an appropriate library. Alternatively, selection can be carried out by hybridization of the DNA of the present invention with a DNA that has been incorporated into an appropriate vector and labeled with a DNA fragment or a synthetic DNA encoding some or all of the regions of the polypeptide of the present invention. Hybridization can be carried out by, for example, the method described in Current Protocols in Molecular Biology (edited by Frederick M. Ausubel et al., 1987). DNA of the present invention may be any DNA, as long as they contain nucleotide sequences encoding the polypeptides of the present invention as described above. Such a DNA may be a cDNA identified and isolated from cDNA libraries or the like that are derived from breast, colorectal, esophageal, gastric, prostate or uterine tissue. Such a DNA may also be a synthetic DNA or the like. Vectors for use in library construction may be any of bacteriophages, plasmids, cosmids, phargemids, or the like. Furthermore, by the use of a total RNA fraction or a mRNA fraction prepared from the above cells and/or tissues, amplification can be carried out by a direct reverse transcription coupled polymerase chain reaction (hereinafter abbreviated as "RT-PCR method").

DNA encoding the above polypeptide consisting of an amino acid sequence that is substantially identical to the amino acid sequence of the matriptase stem or DNA encoding the above polypeptide consisting of an amino acid sequence derived from the amino acid sequence of the matriptase stem by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art. In addition, at this time, a possible method for causing a polypeptide to have substantially equivalent biological activity is substitution of homologous amino acids (e.g. polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in the polypeptide of the present invention are preferably conserved.

Furthermore, examples of DNA of the present invention include DNA comprising a nucleotide sequence that encodes the amino acid sequence of the matriptase stem and DNA hybridizing under stringent conditions to the DNA and encoding a polypeptide (protein) having biological activity (function) equivalent to the function of the polypeptide consisting of the amino acid sequence of the matriptase stem. Under such conditions, an example of such DNA capable of hybridizing to DNA comprising the nucleotide sequence that encodes the amino acid sequence of the matriptase stem is DNA comprising a nucleotide sequence that has a degree of overall mean homology with the entire nucleotide sequence of the DNA, such as approximately 80% or more, preferably approximately 90% or more, and more preferably approximately 95% or more. Hybridization can be carried out according to a method known in the art such as a method described in Current Protocols in Molecular Biology (edited by Frederick M. Ausubel et al., 1987) or a method according thereto. Here, "stringent conditions" are, for example, conditions of approximately "1*SSC, 0.1% SDS, and 37° C., more stringent conditions of approximately "0.5*SSC, 0.1% SDS, and 42° C., or even more stringent conditions of approximately "0.2*SSC, 0.1% SDS, and 65° C. With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

A cloned DNA of the present invention can be directly used or used, if desired, after digestion with a restriction enzyme or addition of a linker, depending on purposes. The DNA may have ATG as a translation initiation codon at the 5' terminal side and have TAA, TGA, or TAG as a translation termination codon at the 3' terminal side. These translation initiation and translation termination codons can also be added using an appropriate synthetic DNA adapter.

In the methods/uses of the invention the matriptase stem may, for example, be provided in isolated form, such as where the polypeptide of the matriptase stem has been purified at least to some extent. The polypeptide of the matriptase stem may be provided in substantially pure form, that is to say free, to a substantial extent, from other proteins. The polypeptide of the matriptase stem can also be produced using recombinant methods, synthetically produced or produced by a combination of these methods. The matriptase stem can be easily prepared by any method known by persons skilled in the art, which involves producing an expression vector containing a DNA of the present invention or a gene containing a DNA of the present invention, culturing a transformant transformed using the expression vector, generating and accumulating a polypeptide of the present invention or a recombinant protein containing the polypeptide, and then collecting the resultant.

Recombinant polypeptide of the matriptase stem may be prepared by processes well known in the art from genetically engineered host cells comprising expression systems. Accordingly, the present invention also relates to expression systems which comprise a polypeptide of the matriptase stem or nucleic acid, to host cells which are genetically engineered with such expression systems and to the production of the polypeptide of the matriptase stem by recombinant techniques. For recombinant polypeptide of the matriptase stem production, host cells can be genetically engineered to incorporate expression systems or portions thereof for nucleic acids. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, 2nd Ed., Cold Spring Harbour laboratory Press, Cold Spring Harbour, N.Y., 1989).

As host cells, for example, bacteria of the genus *Escherichia, Streptococci, Staphylococci, Streptomyces*, bacteria of the genus *Bacillus*, yeast, *Aspergillus* cells, insect cells, insects, and animal cells are used. Specific examples of bacteria of the genus *Escherichia*, which are used herein, include *Escherichia coli* K12 and DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), and HB101 (Journal of Molecular Biology, Vol. 41, 459 (1969)). As bacteria of the genus *Bacillus*, for example, *Bacillus subtilis* MI114 (Gene, Vol. 24, 255 (1983)) and 207-21 (Journal of Biochemistry, Vol. 95, 87 (1984)) are used. As yeast, for example, *Saccaromyces cerevisiae* AH22, AH22R-, NA87-11A, DKD-5D, and 20B-12, *Schizosaccaromyces pombe* NCYC1913 and NCYC2036, and *Pichia pastoris* are used. As insect cells, for example, *Drosophila* S2 and *Spodoptera* Sf9 cells are used. As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, human FL cells, COS, HeLa, C127, 3T3, HEK 293, BHK and Bowes melanoma cells are used.

Cell-free translation systems can also be employed to produce recombinant polypeptides (e.g. rabbit reticulocyte lysate, wheat germ lysate, SP6/T7 in vitro T&T and RTS100 E. Coli HY transcription and translation kits from Roche Diagnostics Ltd., Lewes, UK and the TNT Quick coupled Transcription/Translation System from Promega UK, Southampton, UK).

The expression vector can be produced according to a method known in the art. For example, the vector can be produced by (1) excising a DNA fragment containing a DNA of the present invention or a gene containing a DNA of the present invention and (2) ligating the DNA fragment downstream of the promoter in an appropriate expression vector. A wide variety of expression systems can be used, such as and without limitation, chromosomal, episomal and virus-derived systems, e.g. plasmids derived from *Escherichia coli* (e.g. pBR322, pBR325, pUC18, and pUC118), plasmids derived from *Bacillus subtilis* (e.g. pUB110, pTP5, and pC194), from bacteriophage, from transposons, from yeast episomes (e.g. pSH19 and pSH15), from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage (such as [lambda] phage) genetic elements, such as cosmids and phagemids. The expression systems may contain control regions that regulate as well as engender expression. Promoters to be used in the present invention may be any promoters as long as they are appropriate for hosts to be used for gene expression. For example, when a host is *Escherichia coli*, a trp promoter, a lac promoter, a recA promoter, a pL promoter, an lpp promoter, and the like are preferred. When a host is *Bacillus subtilis*, an SPO1 promoter, an SPO2 promoter, a penP promoter, and the like are preferred. When a host is yeast, a PHO5 promoter, a PGK promoter, a GAP promoter, an ADH promoter, and the like are preferred. When an animal cell is used as a host, examples of promoters for use in this case include an SRa promoter, an SV40 promoter, an LTR promoter, a CMV promoter, and an HSV-TK promoter. Generally, any system or vector that is able to maintain, propagate or express a nucleic acid to produce a polypeptide in a host may be used.

The appropriate nucleic acid sequence may be inserted into an expression system by any variety of well known and routine techniques, such as those set forth in Sambrook et al., supra. Appropriate secretion signals may be incorporated into the polypeptide of the matriptase stem to allow secretion of the translated protein into the lumen of the endoplasmic reticulum, the periplasmic space or the extracellular environment. These signals may be endogenous to the polypeptide of the matriptase stem or they may be heterologous signals. Transformation of the host cells can be carried out according to methods known in the art. For example, the following documents can be referred to: Proc. Natl. Acad. Sci. U.S.A., Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and Virology, Vol. 52, 456 (1973). The thus obtained transformant transformed with an expression vector containing a DNA of the present invention or a gene containing a DNA of the present invention can be cultured according to a method known in the art. For example, when hosts are bacteria of the genus *Escherichia*, the bacteria are generally cultured at approximately 15° C. to 43° C. for approximately 3 to 24 hours. If necessary, aeration or agitation can also be added. When hosts are bacteria of the genus *Bacillus*, the bacteria are generally cultured at approximately 30° C. to 40° C. for approximately 6 to 24 hours. If necessary, aeration or agitation can also be added. When transformants whose hosts are yeast are cultured, culture is generally carried out at approximately 20° C. to 35° C. for approximately 24 to 72 hours using media with pH adjusted to be approximately 5 to 8. If necessary, aeration or agitation can also be added. When transformants whose hosts are animal cells are cultured, the cells are generally cultured at approximately 30° C. to 40° C. for approximately 15 to 60 hours using media with the pH adjusted to be approximately 6 to 8. If necessary, aeration or agitation can also be added.

If a polypeptide of the matriptase stem is to be expressed for use in cell-based screening assays, it is preferred that the polypeptide be produced at the cell surface. In this event, the cells may be harvested prior to use in the screening assay. If the polypeptide of the matriptase stem is secreted into the medium, the medium can be recovered in order to isolate said polypeptide. If produced intracellularly, the cells must first be lysed before the polypeptide of the matriptase stem is recovered.

The polypeptide of the matriptase stem can be recovered and purified from recombinant cell cultures or from other biological sources by well known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to a polypeptide of the matriptase stem can be used to deplete a sample comprising a polypeptide of the matriptase stem of said polypeptide or to purify said polypeptide.

To separate and purify a polypeptide or a protein of the present invention from the culture products, for example, after culture, microbial bodies or cells are collected by a known method, they are suspended in an appropriate buffer, the microbial bodies or the cells are disrupted by, for example, ultrasonic waves, lysozymes, and/or freeze-thawing, the resultant is then subjected to centrifugation or filtration, and then a crude extract of the protein can be obtained. The buffer may also contain a protein denaturation agent such as urea or guanidine hydrochloride or a surfactant such as Triton X-100™. When the protein is secreted in a culture solution, microbial bodies or cells and a supernatant are separated by a known method after the completion of culture and then the supernatant is collected. The protein contained in the thus obtained culture supernatant or the extract can be purified by an appropriate combination of known separation and purification methods. The thus obtained polypeptide (protein) of the present invention can be converted into a salt by a known method or a method according thereto. Conversely, when the polypeptide (protein) of the present invention is obtained in the form of a salt, it can be converted into a free protein or peptide or another salt by a known method or a method according thereto. Moreover, an appropriate protein modification enzyme such as trypsin or chymotrypsin is caused to act on a protein produced by a recombinant before or after purification, so that modification can be arbitrarily added or a polypeptide can be partially removed. The presence of a polypeptide (protein) of the present invention or a salt thereof can be measured by various binding assays, enzyme immunoassays using specific antibodies, and the like.

Techniques well known in the art may be used for refolding to regenerate native or active conformations of the polypeptide of the matriptase stem when the polypeptide has been denatured during isolation and or purification. In the context of the present invention, polypeptide of the matriptase stem can be obtained from a biological sample from any source, such as and without limitation, a tissue sample, e.g. a breast, colorectal, esophageal, gastric, prostate or uterine tissue sample.

The polypeptide of the matriptase stem may be in the form of a "mature protein" or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag.

Matriptase may, for example, be fused with a heterologous fusion partner such as the surface protein, known as protein D from *Haemophilus Influenza* B, a non-structural protein from influenzae virus such as NS1, the S antigen from Hepatitis B or a protein known as LYTA such as the C terminal thereof.

An additional sequence that may provide stability during recombinant production may also be used. Such sequences may be optionally removed as required by incorporating a cleavable sequence as an additional sequence or part thereof. Thus, a polypeptide of the matriptase stem may be fused to other moieties including other polypeptides or proteins (for example, glutathione S-transferase and protein A). Such a fusion protein can be cleaved using an appropriate protease, and then separated into each protein. Such additional sequences and affinity tags are well known in the art. In addition to the above, features known in the art, such as an enhancer, a splicing signal, a polyA addition signal, a selection marker, and an SV40 replication origin can be added to an expression vector, if desired.

Production of Affinity Reagents to the Matriptase Stem

According to those in the art, there are three main types of immunoaffinity reagent—monoclonal antibodies, phage display antibodies and smaller antibody-derived molecules such as Affibodies, Domain Antibodies (dAbs), Nanobodies, Unibodies, DARPins, Anticalins, Duocalins, Avimers or Versabodies. In general in applications according to the present invention where the use of antibodies is stated, other affinity reagents (e.g. Affibodies, Domain Antibodies, Nanobodies, Unibodies, DARPins, Anticalins, Duocalins, Avimers or Versabodies) may be employed. Such substances may be said to be capable of immunospecific binding to matriptase. Where appropriate the term "affinity agent" shall be construed to embrace immunoaffinity reagents and other substances capable of specific binding to matriptase including but not limited to ligands, lectins, streptavidins, antibody mimetics and synthetic binding agents.

Production of Antibodies to the Matriptase Stem

According to the invention the matriptase stem, an analog of the matriptase stem, a related protein to the matriptase stem or a fragment or derivative of any of the foregoing may be used as an immunogen to generate antibodies which immunospecifically bind such an immunogen. Such immunogens can be isolated by any convenient means, including the methods described above. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites" (e.g. fragments, subsequences, complementarity determining regions (CDRs)) that retain capacity to bind antigen, including (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody." Antibodies of the invention include, but are not limited to polyclonal, monoclonal, bispecific, humanized or chimeric antibodies, single chain antibodies, Fab fragments and F(ab')$_2$ fragments, fragments produced by a Fab expression library, anti-idiotypic (anti-Id) antibodies, and epitope-binding fragments of any of the above. The immunoglobulin molecules of the invention can be of any class (e.g. IgG, IgE, IgM, IgD and IgA) or subclass of immunoglobulin molecule.

The term "specifically binds" (or "immunospecifically binds") is not intended to indicate that an antibody binds exclusively to its intended target. Rather, an antibody "specifically binds" if its affinity for its intended target is about 5-fold greater when compared to its affinity for a non-target molecule. Suitably there is no significant cross-reaction or cross-binding with undesired substances, especially naturally occurring proteins or tissues of a healthy person or animal. The affinity of the antibody will, for example, be at least about 5 fold, such as 10 fold, such as 25-fold, especially 50-fold, and particularly 100-fold or more, greater for a target molecule than its affinity for a non-target molecule. In some embodiments, specific binding between an antibody or other binding agent and an antigen means a binding affinity of at least $10^6$ $M^{-1}$. Antibodies may, for example, bind with affinities of at least about $10^7$ $M^{-1}$, such as between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{11}$ $M^{-1}$.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: $r/c = K(n-r)$:

where
r = moles of bound ligand/mole of receptor at equilibrium;
c = free ligand concentration at equilibrium;
K = equilibrium association constant; and
n = number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g. U.S. Pat. No. 6,316,409). The affinity of a targeting agent for its target molecule is, for example, at least about $1 \times 10^{-6}$ moles/liter, such as at least about $1 \times 10^{-7}$ moles/liter, such as at least about $1 \times 10^{-8}$ moles/liter, especially at least about $1 \times 10^{-9}$ moles/liter, and particularly at least about $1 \times 10^{-10}$ moles/liter. Antibody affinity measurement by Scatchard analysis is well known in the art. See, e.g. van Erp et al., *J. Immunoassay* 12: 425-43, 1991; Nelson and Griswold, *Comput. Methods Programs Biomed.* 27: 65-8, 1988.

Methods known to those skilled in the art are used to produce antibodies that recognize the matriptase stem, an analog of the matriptase stem, a related polypeptide of the matriptase stem, or a fragment or derivative of any of the foregoing. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment of the invention, antibodies to a specific domain of the matriptase stem are produced. In a specific embodiment, hydrophilic fragments of the matriptase stem are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of the matriptase stem, one may assay generated hybridomas for a product which binds to a fragment of the matriptase stem containing such domain. For selection of an antibody that specifically binds a first homolog of the matriptase stem but which does not specifically bind to (or binds less avidly to) a second homolog of the matriptase stem, one can select on the basis of positive binding to the first homolog of the matriptase stem and a lack of binding to (or reduced binding to) the second homolog of the matriptase stem. Similarly, for selection of an antibody that specifically binds the matriptase stem but which does not specifically bind to (or binds less avidly to) a different isoform of the same protein (such as a different glycoform having the same core peptide as the matriptase stem), one can select on the basis of positive binding to the matriptase stem and a lack of binding to (or reduced binding to) the different isoform (e.g. a different glycoform). Thus, the present invention provides an antibody (such as a monoclonal antibody) that binds with greater affinity (for example at least 2-fold, such as at least 5-fold, particularly at least 10-fold greater affinity) to the matriptase stem than to a different isoform or isoforms (e.g. glycoforms) of the matriptase stem. Similarly, for selection of an antibody that specifically binds the matriptase stem but which does not specifically bind to (or binds less avidly to) the full-length matriptase (as defined by SEQ ID No: 1), one can select on the basis of positive binding to the matriptase stem and a lack of binding to (or reduced binding to) the full-length matriptase. Thus, the present invention provides an antibody (such as a monoclonal antibody) that binds with greater affinity (for example at least 2-fold, such as at least 5-fold, particularly at least 10-fold greater affinity) to the matriptase stem than to the full-length matriptase.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to the matriptase stem, a fragment of the matriptase stem, a related polypeptide to the matriptase stem, or a fragment of a related polypeptide to the matriptase stem. For example, one way is to purify polypeptides of interest or to synthesize the polypeptides of interest using, e.g. solid phase peptide synthesis methods well known in the art. See, e.g. *Guide to Protein Purification*, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. If the matriptase stem is purified by gel electrophoresis, the matriptase stem can be used for immunization with or without prior extraction from the polyacrylamide gel. Various adjuvants (i e immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (*bacille Calmette-Guerin*) or *corynebacterium parvum*. Additional adjuvants are also well known in the art.

For preparation of monoclonal antibodies (mAbs) directed toward the matriptase stem, a fragment of the matriptase stem, a related polypeptide to the matriptase stem, or a fragment of a related polypeptide to the matriptase stem, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g. human-mouse chimeras). A chimeric antibody is a molecule in which different portions are derived from different animal species, such as those having a human immunoglobulin constant region and a variable region derived from a murine mAb. (See e.g. Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g. Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060.

Completely human antibodies are particularly desirable for therapeutic treatment of human subjects. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g. all or a portion of the matriptase stem. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g. U.S. Pat. Nos. 5,625,126; 5,633,425; 5,569,825; 5,661,016; and 5,545,806. In addition, companies such as Medarex (Princeton, N.J.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g. a mouse antibody, is used to guide the selection of a completely human antibody recognizing the same epitope. (Jespers et al. (1994) Bio/technology 12:899-903).

The antibodies of the present invention can also be generated by the use of phage display technology to produce and screen libraries of polypeptides for binding to a selected target. See, e.g. Cwirla et al., Proc. Natl. Acad. Sci. USA 87, 6378-82, 1990; Devlin et al., Science 249, 404-6, 1990, Scott and Smith, Science 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g. U.S. Pat. No. 6,057,098, which is hereby incorporated in its entirety, including all tables, figures, and claims. In particular, such phage can be utilized to display antigen binding domains expressed from a repertoire or combinatorial antibody library (e.g. human or murine). Phage expressing an antigen binding domain that binds the antigen of interest can be selected or identified with antigen, e.g. using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g. as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

The invention further provides for the use of bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, *EMBO J.* 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology, 1986, 121: 210.

The invention provides functionally active fragments, derivatives or analogs of the anti-matriptase stem immunoglobulin molecules. Functionally active means that the fragment, derivative or analog is able to elicit anti-anti-idiotype antibodies (i.e. tertiary antibodies) that recognize the same antigen that is recognized by the antibody from which the fragment, derivative or analog is derived. Specifically, in a particular embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CH1 domain of the heavy chain and are generated by pepsin digestion of the antibody molecule. Fab fragments are generated by reducing the disulfide bridges of the F(ab')$_2$ fragments. The invention also provides heavy chain and light chain dimers of the antibodies of the invention, or any minimal fragment thereof such as Fvs or single chain antibodies (SCAs) (e.g. as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are modified, i.e. by the covalent attachment of any type of molecule as long as such covalent attachment does not impair immunospecific binding. For example, but not by way of limitation, the derivatives and analogs of the immunoglobulins include those that have been further modified, e.g. by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing antibodies can be used in methods known in the art relating to the localization and activity of the matriptase stem, e.g. for imaging, measuring levels thereof in appropriate physiological samples, in diagnostic methods, etc.

A specific process for preparing a monoclonal antibody which is capable of immunospecific binding to the matriptase stem comprises the step of immunising a non-human animal (eg mouse or rabbit) with a protein which is the matriptase stem (eg as defined by any one of SEQ ID Nos 10-13) or an immunogenic fragment thereof or a fusion protein containing the matriptase stem or an immunogenic fragment thereof or immunising a non-human animal with cells which express such a protein in either case optionally together with an immunostimulant (eg alum, CpG, Ribi adjuvant etc). An exemplary fusion protein contains the matriptase stem or an immunogenic fragment thereof together with an N-terminal osteonectin signal sequence, and the C-terminal Factor Xa cleavage site and human FcG1. For example, the non-human animal may be immunised with a fusion protein, such as defined by SEQ ID No 15, or cells which express said protein. Further steps of the process may typically comprise isolating antibody producing cells from said animal, and immortalising them by fusing them with immortal cells (e.g. the Sp2/0 myeloma cell line (ATCC CRL 1581)) to produce an antibody-producing hybridoma. Antibodies may then be isolated from said hybridoma. If desired the specificity of antibodies may be assessed by determining their ability to bind immunospecifically to the matriptase stem (see eg Example 3) either before or after hybridoma formation. As described above, transgenic animals (eg transgenic mice) may be employed to produce fully human antibodies. Such transgenic animals are adapted to express human immunoglobulin heavy and light chain genes and not endogenous immunoglobulin heavy and light chain genes. Alternatively non-human animal antibodies may be humanised. A humanised monoclonal antibody which is capable of immunospecific binding to the matriptase stem will suitably be characterised by having one or more CDRs (eg 2, 3, 4, 5 or 6 or more for example 1, 2 or 3 or more for each of the light and heavy chains) of such a non-human animal monoclonal antibody. Humanised antibodies may have the CDRs of such a monoclonal antibody and human or humanised framework regions of the variable region. Where a constant region is present this (these) will typically be human. Whole (bivalent) antibodies may be employed or derivatives thereof (eg Fab fragments, ScFv derivatives) may be prepared as described above.

Production of Affibodies to the Matriptase Stem

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

Production of Domain Antibodies to the Matriptase Stem

Domain Antibodies (dAbs) are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582, 915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Production of Nanobodies to the Matriptase Stem

Nanobodies are antibody-derived therapeutic proteins that contain the unique structural and functional properties of naturally-occurring heavy-chain antibodies. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. Nanobodies have a high homology with the VH domains of human antibodies and can be further humanised without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognising uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), moulds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughout selection of B-cells.

Production of Unibodies to the Matriptase Stem

UniBodies are another antibody fragment technology; however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent WO2007/059782, which is herein incorporated by reference in its entirety.

Production of DARPins to the Matriptase Stem

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in US Patent Application Publication No. 2004/0132028, and International Patent Application Publication No. WO 02/20565, both of which are hereby incorporated by reference in their entirety.

Production of Anticalins to the Matriptase Stem

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein; they can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Application Publication No. WO 99/16873, both of which are hereby incorporated by reference in their entirety.

Production of Avimers to the Matriptase Stem

Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in US Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Production of Versabodies to the Matriptase Stem

Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in $E.\ coli$ at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in US Patent Application Publication No. 2007/0191272 which is hereby incorporated by reference in its entirety.

Expression of Affinity Reagents

Expression of Antibodies

The antibodies of the invention can be produced by any method known in the art for the synthesis of antibodies, in particular, by chemical synthesis or by recombinant expression, and are preferably produced by recombinant expression techniques.

Recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesized oligonucleotides (e.g. as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g. an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, more preferably, by generating monoclonal antibodies. Alternatively, a clone encoding at least the Fab portion of the antibody may be obtained by screening Fab expression libraries (e.g. as described in Huse et al., 1989, $Science$ 246:1275-1281) for clones of Fab fragments that bind the specific antigen or by screening antibody libraries (See, e.g. Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g. PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydryl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCR based methods, etc.

In addition, techniques developed for the production of "chimeric antibodies" (Morrison et al., 1984, Proc. Natl. Acad. Sci. 81:851-855; Neuberger et al., 1984, $Nature$ 312:604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g. humanized antibodies.

Once a nucleic acid encoding an antibody molecule of the invention has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, $2^{nd}$ Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus are an effective expression system for antibodies (Foecking et al., 1986, Gene 45:101; Cockett et al., 1990, Bio/Technology 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g. *E. coli, B. subtilis*) transformed with recombinant bacteriophage DNA, plasmid DNA or cosmid DNA expression vectors containing antibody coding sequences; yeast (e.g. *Saccharomyces, Pichia*) transformed with recombinant yeast expression vectors containing antibody coding sequences; insect cell systems infected with recombinant virus expression vectors (e.g. baculovirus) containing the antibody coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing antibody coding sequences; or mammalian cell systems (e.g. COS, CHO, BHK, 293, 3T3 cells) harboring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g. an adenovirus expression system) may be utilized.

As discussed above, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g. neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g. ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analysed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g. in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

For therapeutic applications, antibodies (particularly monoclonal antibodies) may suitably be human or humanized animal (e.g. mouse) antibodies. Animal antibodies may be raised in animals using the human protein (e.g. the matriptase stem) as immunogen. Humanisation typically involves grafting CDRs identified thereby into human framework regions. Normally some subsequent retromutation to optimize the conformation of chains is required. Such processes are known to persons skilled in the art.

Expression of Affibodies

The construction of affibodies has been described elsewhere (Ronnmark J, Gronlund H, Uhle' n, M., Nygren P. A°, Human immunoglobulin A (IgA)-specific ligands from combinatorial engineering of protein A, 2002, Eur. J. Biochem. 269, 2647-2655.), including the construction of affibody phage display libraries (Nord, K., Nilsson, J., Nilsson, B., Uhle' n, M. & Nygren, P. A°, A combinatorial library of an a-helical bacterial receptor domain, 1995, Protein Eng. 8, 601-608. Nord, K., Gunneriusson, E., Ringdahl, J., Sta°hl, S., Uhle' n, M. & Nygren, P. A°, Binding proteins selected from combinatorial libraries of an a-helical bacterial receptor domain, 1997, Nat. Biotechnol. 15, 772-777.)

The biosensor analyses to investigate the optimal affibody variants using biosensor binding studies has also been described elsewhere (Ronnmark J, Gronlund H, Uhle' n, M., Nygren P. A°, Human immunoglobulin A (IgA)-specific ligands from combinatorial engineering of protein A, 2002, Eur. J. Biochem. 269, 2647-2655.).

Affinity Reagent Modifications

In a preferred embodiment, anti-matriptase stem affinity reagents such as antibodies or fragments thereof are conjugated to a diagnostic moiety (such as a detectable label) or a therapeutic moiety. The antibodies can be used for diagnosis or to determine the efficacy of a given treatment regimen. Detection can be facilitated by coupling the antibody to a detectable substance (label). Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc. $^{68}$Ga may also be employed.

Anti-matriptase stem antibodies or fragments thereof as well as other affinity reagents can be conjugated to a therapeutic agent or drug moiety to modify a given biological response. An exemplary therapeutic agent to which the affinity reagent may be conjugated is a cytotoxic moiety. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g. angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g. Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

The invention also provides for fully human, or humanised antibodies that induce antibody-directed cell-mediated cytotoxicity (ADCC). A fully human antibody is one in which the protein sequences are encoded by naturally occurring human immunoglobulin sequences, either from isolated antibody-producing human B-lymphocytes, or from transgenic murine B-lymphocytes of mice in which the murine immunoglobulin coding chromosomal regions have been replaced by orthologous human sequences. Transgenic antibodies of the latter type include, but are not restricted to, HuMab (Medarex, Inc., CA) and Xenomouse (Abgenix Inc., CA). A humanised antibody is one in which the constant region of a non-human antibody molecule of appropriate antigen specificity, is replaced by the constant region of a human antibody, preferably of the IgG subtype, with appropriate effector functions (Morrison et al., 1984, Proc. Natl. Acad. Sci. 81:851-855; Neuberger et al., 1984, Nature 312:604-608; Takeda et al., 1985, Nature 314:452-454). Appropriate effector functions include ADCC, which is a natural process by which fully-human antibodies or humanized antibodies, when bound to targets on the surface of cancer cells, switch on the cell killing properties of lymphocytes that are part of the normal immune system. These active lymphocytes, called Natural Killer (NK) cells, use a cytotoxic process to destroy living cells to which the antibodies are bound. ADCC activity may be detected and quantified by measuring release of Europium (Eu3+) from Eu3+ labelled, living cells in the presence of an antigen-specific antibody and peripheral blood mononuclear cells extracted from an immunocompetent, living human subject. The ADCC process is described in detail in Janeway Jr. C. A. et al., Immunobiology, 5th ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532: p 2153-68 and Weng, W.-K. et al., Journal of Clinical Oncology, 2003, 21: p 3940-3947. Suitable methods for the detection and quantification of ADCC can be found in Blomberg et al., Journal of Immunological Methods. 1986, 86: p 225-9; Blomberg et al., Journal of Immunological Methods. 1986, 21; 92: p 117-23 and Patel & Boyd, Journal of Immunological Methods. 1995, 184: p 29-38.

ADCC typically involves activation of NK cells and is dependent on the recognition of antibody-coated cells by Fc receptors on the surface of the NK cell. The Fc receptors recognize the Fc (crystalline) portion of antibodies such as IgG, bound specifically to the surface of a target cell. The Fc receptor that triggers activation of the NK cell is called CD16 or FcγRIIIa. Once the FcγRIIIa receptor is bound to the IgG Fc, the NK cell releases cytokines such as IFN-γ, and cytotoxic granules containing perform and granzymes that enter the target cell and promote cell death by triggering apoptosis.

The induction of antibody-dependent cellular cytotoxicity (ADCC) by an antibody can be enhanced by modifications that alter interactions between the antibody constant region (Fc) and various receptors that are present on the surface of cells of the immune system. Such modifications include the reduction or absence of alpha1,6-linked fucose moieties in the complex oligosaccharide chains that are normally added to the Fc of antibodies during natural or recombinant synthesis in mammalian cells. In a preferred embodiment, non-fucosylated anti-matriptase stem affinity reagents such as antibodies or fragments thereof are produced for the purpose of enhancing their ability to induce the ADCC response.

Techniques for reducing or ablating alpha1,6-linked fucose moieties in the oligosaccharide chains of the Fc are well established. In one example, the recombinant antibody is synthesized in a cell line that is impaired in its ability to add fucose in an alpha 1,6 linkage to the innermost N-acetylglucosamine of the N-linked biantennary complex-type Fc oligosaccharides. Such cell lines include, but are not limited to, the rat hybridoma YB2/0, which expresses a reduced level of the alpha 1,6-fucosyltransferase gene, FUT8. Preferably, the antibody is synthesized in a cell line that is incapable of adding alpha 1,6-linked fucosyl moieties to complex oligosaccharide chains, due to the deletion of both copies of the FUT8 gene. Such cell lines include, but are not limited to, FUT8-/- CHO/DG44 cell lines. Techniques for synthesizing partially fucosylated, or non-fucosylated antibodies and affinity reagents are described in Shinkawa et al., J. Biol. Chem. 278:3466-34735 (2003); Yamane-Ohnuki et al., Biotechnology and Bioengineering 87: 614-22 (2004) and in WO00/61739 A1, WO02/31140 A1 and WO03/085107 A1. In a second example, the fucosylation of a recombinant antibody is reduced or abolished by synthesis in a cell line that has been genetically engineered to overexpress a glycoprotein-modifying glycosyl transferase at a level that maximizes the production of complex N-linked oligosaccharides carrying bisecting N-acetylglucosamine. For example, the antibody is synthesized in a Chinese Hamster Ovary cell line expressing the enzyme N-acetyl glucosamine transferase III (GnT III). Cell lines stably transfected with suitable glycoprotein-modifying glycosyl transferases, and methods of synthesizing antibodies using these cells are described in WO9954342.

A non-fucosylated antibody or affinity reagent can be used as a therapeutic that is administered alone or in combination with cytotoxic factor(s) and/or cytokine(s).

In a further modification, the amino acid sequences of the antibody Fc are altered in a way that enhances ADCC activation, without affecting ligand affinity. Examples of such modifications are described in Lazar et al., Proceedings of the National Academy of Sciences 2006, 103: p 4005-4010; WO03074679 and WO2007039818. In these examples, substitution of amino acids in the antibody Fc, such as aspartate for serine at position 239, and isoleucine for glutamate at position 332, altered the binding affinity of an antibody for Fc receptors, leading to an increase in ADCC activation.

An antibody reagent with enhanced ADCC activation due to amino acid substitutions can be used as a therapeutic that is administered alone or in combination with cytotoxic factor(s) and/or cytokine(s).

Diagnosis of Breast Cancer, Colorectal Cancer, Esophageal Cancer, Gastric Cancer, Prostate Cancer and Uterine Cancer In accordance with the present invention, test samples of breast, colorectal, esophageal, gastric, prostate or uterine tissue obtained from a subject suspected of having or known to have breast cancer, colorectal cancer, esophageal cancer, gastric cancer, prostate cancer or uterine cancer can be used for diagnosis or monitoring. In one embodiment, a change in the abundance of the matriptase stem in a test sample relative to a control sample (from a subject or subjects free from breast cancer, colorectal cancer, esophageal cancer, gastric cancer, prostate cancer and uterine cancer) or a previously determined reference range indicates the presence of breast cancer, colorectal cancer, esophageal cancer, gastric cancer, prostate cancer or uterine cancer. In another embodiment, the relative abundance of the matriptase stem in a test sample compared to a control sample or a previously determined reference range indicates a subtype of breast cancer, colorectal cancer, esophageal cancer, gastric cancer, prostate cancer or uterine cancer (e.g. inflammatory breast cancer; familial or sporadic colorectal cancer; squamous cell esophageal cancer; gastrointestinal stromal tumours or squamous cell cervical carcinoma). In yet another embodiment, the relative abundance of the matriptase stem in a test sample relative to a control sample or a previously determined reference range indicates the degree or severity of breast cancer, colorectal cancer, esophageal cancer, gastric cancer, prostate cancer or uterine cancer (e.g. the likelihood for metastasis). In any of the aforesaid methods, detection of the matriptase stem may optionally be combined with detection of one or more of additional biomarkers for breast cancer, colorectal cancer, esophageal cancer, gastric cancer, prostate cancer or uterine cancer. Any suitable method in the art can be employed to measure the level of the matriptase stem, including but not limited to the Preferred Technologies described herein, kinase assays, immunoassays to detect and/or visualize the matriptase stem (e.g. Western blot, immunoprecipitation followed by sodium dodecyl sulfate polyacrylamide gel electrophoresis, immunocytochemistry, etc.). In a further embodiment, a change in the abundance of mRNA encoding the matriptase stem in a test sample relative to a control sample or a previously determined reference range indicates the presence of breast cancer, colorectal cancer, esophageal cancer, gastric cancer, prostate cancer or uterine cancer. Any suitable hybridization assay can be used to detect the matriptase stem expression by detecting and/or visualizing mRNA encoding the matriptase stem (e.g. Northern assays, dot blots, in situ hybridization, etc.).

In another embodiment of the invention, labeled antibodies (or other affinity reagents), derivatives and analogs thereof, which specifically bind to the matriptase stem can be used for diagnostic purposes to detect, diagnose, or monitor breast cancer, colorectal cancer, esophageal cancer, gastric cancer, prostate cancer or uterine cancer. For example, breast cancer, colorectal cancer, esophageal cancer, gastric cancer, prostate cancer or uterine cancer is detected in an animal, such as in a mammal and particularly in a human.

Screening Assays

The invention provides methods for identifying agents (e.g. candidate compounds or test compounds) that bind to the matriptase stem or have a stimulatory or inhibitory effect on the expression or activity of the matriptase stem. The invention also provides methods of identifying agents, candidate compounds or test compounds that bind to a polypeptide related to the matriptase stem or a fusion protein of the matriptase stem or have a stimulatory or inhibitory effect on the expression or activity of a polypeptide related to the matriptase stem or a fusion protein of the matriptase stem. Examples of agents, candidate compounds or test compounds include, but are not limited to, nucleic acids (e.g. DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233, each of which is incorporated herein in its entirety by reference.

Libraries of compounds may be presented, e.g. presented in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310), each of which is incorporated herein in its entirety by reference.

In one embodiment, agents that interact with (i.e. bind to) the matriptase stem, a fragment of the matriptase stem (e.g. a functionally active fragment), a polypeptide related to the matriptase stem, a fragment of a polypeptide related to the matriptase stem, or a fusion protein of the matriptase stem are identified in a cell-based assay system. In accordance with this embodiment, cells expressing the matriptase stem, a fragment of the matriptase stem, a polypeptide related to the matriptase stem, a fragment of a polypeptide related to the matriptase stem, or a fusion protein of the matriptase stem are contacted with a candidate compound or a control compound and the ability of the candidate compound to interact with the matriptase stem is determined. If desired, this assay may be used to screen a plurality (e.g. a library) of candidate compounds. The cell, for example, can be of prokaryotic origin (e.g. E. coli) or eukaryotic origin (e.g. yeast or mammalian). Further, the cells can express the matriptase stem, a fragment of the matriptase stem, a polypeptide related to the matriptase stem, a fragment of a polypeptide related to the matriptase stem, or a fusion protein of the matriptase stem endogenously or be genetically engineered to express the matriptase stem, a fragment of the matriptase stem, a polypeptide related to the matriptase stem, a fragment of a polypeptide related to the matriptase stem, or a fusion protein of the matriptase stem. In certain instances, the matriptase stem, a fragment of the matriptase stem, a polypeptide related to the matriptase stem, a fragment of a polypeptide related to the matriptase stem, or a fusion protein of the matriptase stem or the candidate compound is labeled, for example with a radioactive label (such as $^{32}P$, $^{35}S$, and $^{125}I$) or a fluorescent label (such as fluorescein isothiocyanate, rhodamine, phycoerythrin, phycocyanin, allophycocyanin, o-phthaldehyde or fluorescamine) to enable detection of an interaction between the matriptase stem and a candidate compound. The ability of the candidate compound to interact directly or indirectly with the matriptase stem, a fragment of the matriptase stem, a polypeptide related to the matriptase stem, a fragment of a polypeptide related to the matriptase stem, or a fusion protein of the matriptase stem can be determined by methods known to those of skill in the art. For example, the interaction between a candidate compound and the matriptase stem, a fragment of the matriptase stem, a polypeptide related to the matriptase stem, a fragment of a polypeptide related to the matriptase stem, or a fusion protein of the matriptase stem can be determined by flow cytometry, a scintillation assay, immunoprecipitation or western blot analysis.

In another embodiment, agents that interact with (i.e. bind to) the matriptase stem, a fragment of the matriptase stem, a polypeptide related to the matriptase stem, a fragment of a polypeptide related to the matriptase stem, or a fusion protein of the matriptase stem are identified in a cell-free assay system. In accordance with this embodiment, a native or recombinant polypeptide of the matriptase stem or fragment thereof, or a native or recombinant polypeptide related to the matriptase stem or fragment thereof, or a fusion protein of the matriptase stem or fragment thereof, is contacted with a candidate compound or a control compound and the ability of the candidate compound to interact with the matriptase stem or polypeptide related to the matriptase stem, or fusion protein of the matriptase stem is determined. If desired, this assay may be used to screen a plurality (e.g. a library) of candidate compounds. Preferably, the matriptase stem, a fragment of the matriptase stem, a polypeptide related to the matriptase stem, a fragment of a polypeptide related to the matriptase stem, or a fusion protein of the matriptase stem is first immobilized, by, for example, contacting the matriptase stem, a fragment of the matriptase stem, a polypeptide related to the matriptase stem, a fragment of a polypeptide related to the matriptase stem, or a fusion protein of the matriptase stem with an immobilized antibody (or other affinity reagent) which specifically recognizes and binds it, or by contacting a purified preparation of the matriptase stem, a fragment of the matriptase stem, a polypeptide related to the matriptase stem, a fragment of a polypeptide related to the matriptase stem, or a fusion protein of the matriptase stem with a surface designed to bind proteins. The matriptase stem, a fragment of the matriptase stem, a polypeptide related to the matriptase stem, a fragment of a polypeptide related to the matriptase stem, or a fusion protein of the matriptase stem may be partially or completely purified (e.g. partially or completely free of other polypeptides) or part of a cell lysate. Further, the matriptase stem, a fragment of the matriptase stem, a polypeptide related to the matriptase stem or a fragment of a polypeptide related to the matriptase stem may be a fusion protein comprising the matriptase stem or a biologically active portion thereof, or a polypeptide related to the matriptase stem and a domain such as glutathionine-S-transferase. Alternatively, the matriptase stem, a fragment of the matriptase stem, a polypeptide related to the matriptase stem, a fragment of a polypeptide related to the matriptase stem, or a fusion protein of the matriptase stem can be biotinylated using techniques well known to those of skill in the art (e.g. biotinylation kit, Pierce Chemicals; Rockford, Ill.). The ability of the candidate compound to interact with the matriptase stem, a fragment of the matriptase stem, a polypeptide related to the matriptase stem, a fragment of a polypeptide related to the matriptase stem, or a fusion protein of the matriptase stem can be determined by methods known to those of skill in the art.

In another embodiment, a cell-based assay system is used to identify agents that bind to or modulate the activity of a protein, such as an enzyme, or a biologically active portion thereof, which is responsible for the production or degradation of the matriptase stem or is responsible for the post-translational modification of the matriptase stem. In a primary screen, a plurality (e.g. a library) of compounds are contacted with cells that naturally or recombinantly express: (i) the matriptase stem, an isoform of the matriptase stem, a homolog of the matriptase stem, a polypeptide related to the matriptase stem, a fusion protein of the matriptase stem, or a biologically active fragment of any of the foregoing; and (ii) a protein that is responsible for processing of the matriptase stem, an isoform of the matriptase stem, a homolog of the matriptase stem, a polypeptide related to the matriptase stem, a fusion protein of the matriptase stem, or fragment in order to identify compounds that modulate the production, degradation, or post-translational modification of the matriptase stem, an isoform of the matriptase stem, a homolog of the matriptase stem, a polypeptide related to the matriptase stem, a fusion protein of the matriptase stem or fragment. If desired, compounds identified in the primary screen can then be assayed in a secondary screen against cells naturally or recombinantly expressing the matriptase stem. The ability of the candidate compound to modulate the production, degradation or post-translational modification of the matriptase stem, isoform of the matriptase stem, homolog of the matriptase stem, polypeptide related to the matriptase stem or fusion protein of the matriptase stem can be determined by methods known to those of skill in the art, including without limitation, flow cytometry, a scintillation assay, immunoprecipitation and western blot analysis.

In another embodiment, agents that competitively interact with (i.e. bind to) the matriptase stem, a fragment of the matriptase stem, a polypeptide related to the matriptase stem, a fragment of a polypeptide related to the matriptase stem, or a fusion protein of the matriptase stem are identified in a competitive binding assay. In accordance with this embodiment, cells expressing the matriptase stem, a fragment of the matriptase stem, a polypeptide related to the matriptase stem, a fragment of a polypeptide related to the matriptase stem, or a fusion protein of the matriptase stem are contacted with a candidate compound and a compound known to interact with the matriptase stem, a fragment of the matriptase stem, a polypeptide related to the matriptase stem, a fragment of a polypeptide related to the matriptase stem, or a fusion protein of the matriptase stem; the ability of the candidate compound to preferentially interact with the matriptase stem, a fragment of the matriptase stem, a polypeptide related to the matriptase stem, a fragment of a polypeptide related to the matriptase stem, or a fusion protein of the matriptase stem is then determined. Alternatively, agents that preferentially interact with (i.e. bind to) the matriptase stem, a fragment of the matriptase stem, a polypeptide related to the matriptase stem, a fragment of a polypeptide related to the matriptase stem, or a fusion protein of the matriptase stem are identified in a cell-free assay system by contacting the matriptase stem, a fragment of the matriptase stem, a polypeptide related to the matriptase stem, a fragment of a polypeptide related to the matriptase stem, or a fusion protein of the matriptase stem with a candidate compound and a compound known to interact with the matriptase stem, the polypeptide related to the matriptase stem or the fusion protein of the matriptase stem. As stated above, the ability of the candidate compound to interact with the matriptase stem, a fragment of the matriptase stem, a polypeptide related to the matriptase stem, a fragment of a polypeptide related to the matriptase stem, or a fusion protein of the matriptase stem can be determined by methods known to those of skill in the art. These assays, whether cell-based or cell-free, can be used to screen a plurality (e.g. a library) of candidate compounds.

In another embodiment, agents that modulate (i.e. upregulate or downregulate) the expression or activity of the matriptase stem, or a polypeptide related to the matriptase stem are identified by contacting cells (e.g. cells of prokaryotic origin or eukaryotic origin) expressing the matriptase stem, or polypeptide related to the matriptase stem with a candidate compound or a control compound (e.g. phosphate buffered saline (PBS)) and determining the expression of the matriptase stem, polypeptide related to the matriptase stem, or fusion protein of the matriptase stem, mRNA encoding the matriptase stem, or mRNA encoding the polypeptide related to the matriptase stem. The level of expression of the matriptase stem, polypeptide related to the matriptase stem, mRNA encoding the matriptase stem, or mRNA encoding the polypeptide related to the matriptase stem in the presence of the candidate compound is compared to the level of expression of the matriptase stem, polypeptide related to the matriptase stem, mRNA encoding the matriptase stem, or mRNA encoding the polypeptide related to the matriptase stem in the absence of the candidate compound (e.g. in the presence of a control compound). The candidate compound can then be identified as a modulator of the expression of the matriptase stem, or the polypeptide related to the matriptase stem based on this comparison. For example, when expression of the matriptase stem or mRNA is significantly greater in the presence of the candidate compound than in its absence, the candidate compound is identified as a stimulator of expression of the matriptase stem or mRNA. Alternatively, when expression of the matriptase stem or mRNA is significantly less in the presence of the candidate compound than in its absence, the candidate compound is identified as an inhibitor of the expression of the matriptase stem or mRNA. The level of expression of the matriptase stem or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of the matriptase stem or a polypeptide related to the matriptase stem are identified by contacting a preparation containing the matriptase stem or a polypeptide related to the matriptase stem or cells (e.g. prokaryotic or eukaryotic cells) expressing the matriptase stem or a polypeptide related to the matriptase stem with a test compound or a control compound and determining the ability of the test compound to modulate (e.g. stimulate or inhibit) the activity of the matriptase stem or a polypeptide related to the matriptase stem. The activity of the matriptase stem or a polypeptide related to the matriptase stem can be assessed by detecting induction of a cellular signal transduction pathway of the matriptase stem or polypeptide related to the matriptase stem (e.g. intracellular $Ca^{2+}$, diacylglycerol, IP3, etc.), detecting catalytic or enzymatic activity of the target on a suitable substrate, detecting the induction of a reporter gene (e.g. a regulatory element that is responsive to the matriptase stem or a polypeptide related to the matriptase stem and is operably linked to a nucleic acid encoding a detectable marker, e.g. luciferase), or detecting a cellular response, for example, cellular differentiation, or cell proliferation. Based on the present description, techniques known to those of skill in the art can be used for measuring these activities (see e.g. U.S. Pat. No. 5,401,639, which is incorporated herein by reference). The candidate compound can then be identified as a modulator of the activity of the matriptase stem or a polypeptide related to the matriptase stem by comparing the effects of the candidate compound to the control compound. Suitable control compounds include phosphate buffered saline (PBS) and normal saline (NS).

In another embodiment, agents that modulate (i.e. upregulate or downregulate) the expression, activity or both the expression and activity of the matriptase stem or a polypeptide related to the matriptase stem are identified in an animal model. Examples of suitable animals include, but are not limited to, mice, rats, rabbits, monkeys, guinea pigs, dogs and cats. Preferably, the animal used represent a model of breast cancer, colorectal cancer, esophageal cancer, gastric cancer, prostate cancer or uterine cancer (e.g. xenografts of breast cancer cell lines such as MCF-7 (Ozzello L, Sordat M., Eur J Cancer. 1980; 16:553-559) and MCF10AT (Miller et al., J Natl Cancer Inst. 1993; 85:1725-1732) in nude or SCID mice; xenografts of human colorectal cancer cell lines such as MDA-MB-345 in oestrogen-deprived SCID mice, Eccles et al. 1994 Cell Biophysics 24/25, 279; xenografts of gastric cell lines such as AZ-521 in nude mice; xenografts of prostate cancer cell lines such as CWR-22 in nude mice, Pretlow et al, J Natl Cancer Inst. 1993 Mar. 3; 85(5):394-8 or xenografts of cervical cancer cell lines such as CaSki in nude mice). These can be utilized to test compounds that modulate levels of the matriptase stem, since the pathology exhibited in these models is similar to that of breast cancer, colorectal cancer, esophageal cancer, gastric cancer, prostate cancer and uterine cancer. In accordance with this embodiment, the test compound or a control compound is administered (e.g. orally, rectally or parenterally such as intraperitoneally or intravenously) to a suitable animal and the effect on the expression, activity or both expression and activity of the matriptase stem or a polypeptide related to the matriptase stem is determined. Changes in the expression of the matriptase stem or a polypeptide related to the matriptase stem can be assessed by the methods outlined above.

In yet another embodiment, the matriptase stem or a polypeptide related to the matriptase stem is used as a "bait protein" in a two-hybrid assay or three hybrid assay to identify other proteins that bind to or interact with the matriptase stem or a polypeptide related to the matriptase stem (see e.g. U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300). As those skilled in the art will appreciate, such binding proteins are also likely to be involved in the propagation of signals by the matriptase stem as, for example, upstream or downstream elements of a signaling pathway involving the matriptase stem.

This invention further provides novel agents identified by the above-described screening assays and uses thereof for treatments as described herein. In addition, the invention also provides the use of an agent which interacts with, or modulates the activity of, the matriptase stem in the manufacture of a medicament for the treatment of breast cancer, colorectal cancer, esophageal cancer, gastric cancer, prostate cancer or uterine cancer.

Therapeutic Use of the Matriptase Stem

The invention provides for treatment or prevention of various diseases and disorders by administration of a therapeutic compound. Such compounds include but are not limited to: the matriptase stem, analogs of the matriptase stem, polypeptides related to the matriptase stem and derivatives (including fragments) thereof; antibodies (or other affinity reagents) to the foregoing; nucleic acids encoding the matriptase stem, analogs of the matriptase stem, polypeptides related to the matriptase stem and fragments thereof; antisense nucleic acids to a gene encoding the matriptase stem or a polypeptide related to the matriptase stem; and modulator (e.g. agonists and antagonists) of a gene encoding the matriptase stem or a polypeptide related to the matriptase stem. An important feature of the present invention is the identification of genes encoding the matriptase stem involved in breast cancer, colorectal cancer, esophageal cancer, gastric cancer, prostate cancer or uterine cancer. Breast cancer, colorectal cancer, esophageal cancer, gastric cancer, prostate cancer or uterine cancer can be treated (e.g. to ameliorate symptoms or to retard onset or progression) or prevented by administration of a therapeutic compound that reduces function or expression of the matriptase stem in the tissue of subjects having breast cancer, colorectal cancer, esophageal cancer, gastric cancer, prostate cancer or uterine cancer.

In one embodiment, one or more antibodies (or other affinity reagents) each specifically binding to the matriptase stem are administered alone or in combination with one or more additional therapeutic compounds or treatments.

A biological product such as an antibody (or other affinity reagent) is, for example, allogeneic to the subject to which it is administered. In one embodiment, a human stem of matriptase or a human polypeptide related to the matriptase stem, a nucleotide sequence encoding a human stem of matriptase or a human polypeptide related to the matriptase stem, or an antibody (or other affinity reagent) to a human stem of matriptase or a human polypeptide related to the matriptase stem, is administered to a human subject for therapy (e.g. to ameliorate symptoms or to retard onset or progression) or prophylaxis.

Without being limited by theory, it is conceived that the therapeutic activity of antibodies (or other affinity reagents) which specifically bind to the matriptase stem may be achieved through the phenomenon of Antibody—Dependent Cell-mediated Cytotoxicity (ADCC) (see e.g. Janeway Jr. C. A. et al., Immunobiology, 5th ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532: p 2153-68 and Weng, W.-K. et al., Journal of Clinical Oncology, 2003, 21: p 3940-3947).

Treatment and Prevention of Breast Cancer, Colorectal Cancer, Esophageal Cancer, Gastric Cancer, Prostate Cancer and Uterine Cancer Breast cancer, colorectal cancer, esophageal cancer, gastric cancer, prostate cancer or uterine cancer is treated or prevented by administration to a subject suspected of having or known to have breast cancer, colorectal cancer, esophageal cancer, gastric cancer, prostate cancer or uterine cancer or to be at risk of developing breast cancer, colorectal cancer, esophageal cancer, gastric cancer, prostate cancer or uterine cancer of a compound that modulates (i.e. increases or decreases) the level or activity (i.e. function) of the matriptase stem that is differentially present in the tissue of subjects having breast cancer, colorectal cancer, esophageal cancer, gastric cancer, prostate cancer or uterine cancer compared with tissue of subjects free from breast cancer, colorectal cancer, esophageal cancer, gastric cancer, prostate cancer and uterine cancer. In one embodiment, breast cancer, colorectal cancer, esophageal cancer, gastric cancer, prostate cancer or uterine cancer is treated or prevented by administering to a subject suspected of having or known to have breast cancer, colorectal cancer, esophageal cancer, gastric cancer, prostate cancer or uterine cancer or to be at risk of developing breast cancer, colorectal cancer, esophageal cancer, gastric cancer, prostate cancer or uterine cancer a compound that upregulates (i.e. increases) the level or activity (i.e. function) of the matriptase stem that are decreased in the tissue of subjects having breast cancer, colorectal cancer, esophageal cancer, gastric cancer, prostate cancer or uterine cancer. Examples of such a compound include, but are not limited to, antisense oligonucleotides or ribozymes of the matriptase stem, antibodies (or other affinity reagents) directed against the matriptase stem, and compounds that inhibit the enzymatic activity of the matriptase stem. Other useful compounds, e.g. antagonists of the matriptase stem and small molecule antagonists of the matriptase stem, can be identified using in vitro assays.

Breast cancer, colorectal cancer, esophageal cancer, gastric cancer, prostate cancer or uterine cancer is also treated or prevented by administration to a subject suspected of having or known to have breast cancer, colorectal cancer, esophageal cancer, gastric cancer, prostate cancer or uterine cancer or to be at risk of developing breast cancer, colorectal cancer, esophageal cancer, gastric cancer, prostate cancer or uterine cancer of a compound that downregulates the level or activity (i.e. function) of the matriptase stem that are increased in the tissue of subjects having breast cancer, colorectal cancer, esophageal cancer, gastric cancer, prostate cancer or uterine cancer. Examples of such a compound include but are not limited to: the stem of matriptase, fragments of the matriptase stem and polypeptides related to the stem of matriptase; nucleic acids encoding the stem of matriptase, a fragment of the matriptase stem and a polypeptide related to the matriptase stem (e.g. for use in gene therapy); and, for those polypeptides of the matriptase stem or related to the matriptase stem with enzymatic activity, compounds or molecules known to modulate that enzymatic activity. Other compounds that can be used, e.g. agonists of the stem of matriptase, can be identified using in in vitro assays.

In another embodiment, therapy or prophylaxis is tailored to the needs of an individual subject. Thus, in specific embodiments, compounds that promote the level or function of the matriptase stem are therapeutically or prophylactically administered to a subject suspected of having or known to have breast cancer, colorectal cancer, esophageal cancer, gastric cancer, prostate cancer or uterine cancer, in whom the levels or functions of said stem of matriptase are absent or are decreased relative to a control or normal reference range. In further embodiments, compounds that promote the level or function of the matriptase stem are therapeutically or prophylactically administered to a subject suspected of having or known to have breast cancer, colorectal cancer, esophageal cancer, gastric cancer, prostate cancer or uterine cancer in whom the levels or functions of said stem of matriptase are increased relative to a control or to a reference range. In further embodiments, compounds that decrease the level or function of the matriptase stem are therapeutically or prophylactically administered to a subject suspected of having or known to have breast cancer, colorectal cancer, esophageal cancer, gastric cancer, prostate cancer or uterine cancer in whom the levels or functions of the matriptase stem are increased relative to a control or to a reference range. In further embodiments, compounds that decrease the level or function of the matriptase stem are therapeutically or prophylactically administered to a subject suspected of having or known to have breast cancer, colorectal cancer, esophageal cancer, gastric cancer, prostate cancer or uterine cancer in whom the levels or functions of the matriptase stem are decreased relative to a control or to a reference range. The change in the function or level of the matriptase stem due to the administration of such compounds can be readily detected, e.g. by obtaining a sample and assaying in vitro the levels or activities of the matriptase stem, or the levels of mRNAs encoding the matriptase stem, or any combination of the foregoing. Such assays can be performed before and after the administration of the compound as described herein.

The compounds of the invention include but are not limited to any compound, e.g. a small organic molecule, protein, peptide, antibody (or other affinity reagent), nucleic acid, etc. that restores the matriptase stem profile towards normal. The compounds of the invention may be given in combination with any other chemotherapy drugs.

Vaccine Therapy

Another aspect of the invention is an immunogenic composition, suitably a vaccine composition, comprising the matriptase stem or an epitope containing fragment thereof, or nucleic acid encoding the matriptase stem or a fragment thereof optionally together with an immunostimulant.

There is also provided a method of raising an immune response which comprises administering to a subject such compositions and a method for treating or preventing breast cancer, colorectal cancer, esophageal cancer, gastric cancer, prostate cancer or uterine cancer which comprises administering to a subject in need thereof a therapeutically effective amount of such compositions and such compositions for use in preventing or treating breast cancer, colorectal cancer, esophageal cancer, gastric cancer, prostate cancer or uterine cancer.

Thus, the matriptase stem may be useful as antigenic material, and may be used in the production of vaccines for treatment or prophylaxis of breast cancer, colorectal cancer, esophageal cancer, gastric cancer, prostate cancer or uterine cancer. Such material can be "antigenic" and/or "immunogenic". Generally, "antigenic" is taken to mean that the protein is capable of being used to raise antibodies (or other affinity reagents) or indeed is capable of inducing an antibody response in a subject or experimental animal "Immunogenic" is taken to mean that the protein is capable of eliciting a protective immune response in a subject or experimental animal. Thus, in the latter case, the protein may be capable of not only generating an antibody response but, in addition, non-antibody based immune responses. "Immunogenic" also embraces whether the protein may elicit an immune-like response in an in-vitro setting e.g. a T-cell proliferation assay. The generation of an appropriate immune response may require the presence of one or more adjuvants and/or appropriate presentation of an antigen.

The skilled person will appreciate that homologues or derivatives of the matriptase stem will also find use as antigenic/immunogenic material. Thus, for instance proteins which include one or more additions, deletions, substitutions or the like are encompassed by the present invention. In addition, it may be possible to replace one amino acid with another of similar "type". For instance, replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein as described herein is less important than that the homologue or derivative should retain its antigenicity and/or immunogenicity. However, suitably, homologues or derivatives having at least 60% similarity (as discussed above) with the proteins or polypeptides described herein are provided, for example, homologues or derivatives having at least 70% similarity, such as at least 80% similarity. Particularly, homologues or derivatives having at least 90% or even 95% similarity are provided. Suitably, homologues or derivatives have at least 60% sequence identity with the proteins or polypeptides described herein, for example, homologues or derivatives have at least 70% identity, such as at least 80% identity. Particularly, homologues or derivatives have at least 90% or even 95% identity.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

It is well known that it is possible to screen an antigenic protein or polypeptide to identify epitopic regions, i.e. those regions which are responsible for the protein or polypeptide's antigenicity or immunogenicity. Methods well known to the skilled person can be used to test fragments and/or homologues and/or derivatives for antigenicity. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties of the protein from which it is derived.

What is important for homologues, derivatives and fragments is that they possess at least a degree of the antigenicity/immunogenicity of the protein or polypeptide from which they are derived. Thus, in an additional aspect of the invention, there is provided antigenic/or immunogenic fragments of the matriptase stem, or of homologues or derivatives thereof.

The matriptase stem, or antigenic fragments thereof, can be provided alone, as a purified or isolated preparation. In a further aspect, therefore, the invention provides an antigen composition comprising the matriptase stem and/or one or more antigenic fragments thereof. Such a composition can be used for the detection and/or diagnosis of breast cancer, colorectal cancer, esophageal cancer, gastric cancer, prostate cancer or uterine cancer.

Vaccine compositions according to the invention may be either a prophylactic or therapeutic vaccine composition.

The vaccine compositions of the invention can include one or more adjuvants (immunostimulants). Examples well-known in the art include inorganic gels, such as aluminium hydroxide, and water-in-oil emulsions, such as incomplete Freund's adjuvant. The adjuvant may also be an immunotherapy such as an anti-CTLA-4 antibody or an anti-PD-1 antibody. Other useful adjuvants will be well known to the skilled person.

Suitable adjuvants for use in vaccine compositions for the treatment of cancer include: 3De-O-acylated monophosphoryl lipid A (known as 3D-MPL or simply MPL see WO92/116556), a saponin, for example QS21 or QS7, and TLR4 agonists such as a CpG containing molecule, for example as disclosed in WO95/26204.

The adjuvants employed may be a combination of components, for example MPL and QS21 or MPL, QS21 and a CpG containing moiety.

Adjuvants may be formulated as oil-in-water emulsions or liposomal formulations.

Such preparations may include other vehicles.

In another embodiment, a preparation of oligonucleotides comprising 10 or more consecutive nucleotides complementary to a nucleotide sequence encoding the matriptase stem or peptide fragments of the matriptase stem is used as vaccines for the treatment of breast cancer, colorectal cancer, esophageal cancer, gastric cancer, prostate cancer or uterine cancer. Such preparations may include adjuvants or other vehicles.

Inhibition of the Matriptase Stem to Treat Breast Cancer, Colorectal Cancer, Esophageal Cancer, Gastric Cancer, Prostate Cancer and Uterine Cancer In one embodiment of the invention, breast cancer, colorectal cancer, esophageal cancer, gastric cancer, prostate cancer or uterine cancer is treated or prevented by administration of a compound that antagonizes (inhibits) the level and/or function of the matriptase stem which are elevated in the tissue of subjects having breast cancer, colorectal cancer, esophageal cancer, gastric cancer, prostate cancer or uterine cancer as compared with tissue of subjects free from breast cancer, colorectal cancer, esophageal cancer, gastric cancer, prostate cancer and uterine cancer.

Compounds useful for this purpose include but are not limited to anti-matriptase stem antibodies (or other affinity reagents, and fragments and derivatives containing the binding region thereof), antisense or ribozyme nucleic acids of the matriptase stem, and nucleic acids encoding dysfunctional the matriptase stem that are used to "knockout" endogenous stem of matriptase function by homologous recombination (see e.g. Capecchi, 1989, *Science* 244:1288-1292). Other compounds that inhibit the function of the matriptase stem can be identified by use of known in vitro assays, e.g. assays for the ability of a test compound to inhibit binding of the matriptase stem to another protein or a binding partner, or to inhibit a known function of the matriptase stem.

Such inhibition may, for example, be assayed in vitro or in cell culture, but genetic assays may also be employed. The Preferred Technologies described herein can also be used to detect levels of the matriptase stem before and after the administration of the compound. Suitable in vitro or in vivo assays are utilized to determine the effect of a specific compound and whether its administration is indicated for treatment of the affected tissue, as described in more detail below.

In a specific embodiment, a compound that inhibits the function (activity) of the matriptase stem is administered therapeutically or prophylactically to a subject in whom an increased tissue level or functional activity of the matriptase stem (e.g. greater than the normal level or desired level) is detected as compared with tissue of subjects with breast cancer, colorectal cancer, esophageal cancer, gastric cancer, prostate cancer or uterine cancer who do not receive treatment according to the invention or to bring the level or activity to that found in subjects free from breast cancer, colorectal cancer, esophageal cancer, gastric cancer, prostate cancer and uterine cancer or a predetermined reference range. Methods standard in the art can be employed to measure the increase in level or function of the matriptase stem, as outlined above. Suitable inhibitor compositions of the matriptase stem may, for example, include small molecules, i.e. molecules of 1000 daltons or less. Such small molecules can be identified by the screening methods described herein.

Assays for Therapeutic or Prophylactic Compounds

The present invention also provides assays for use in drug discovery in order to identify or verify the efficacy of compounds for treatment or prevention of breast cancer, colorectal cancer, esophageal cancer, gastric cancer, prostate cancer and uterine cancer.

Thus there is provided a method of screening for compounds that modulate the activity of the stem of matriptase, the method comprising: (a) contacting the matriptase stem or a biologically active portion thereof with a candidate compound; and (b) determining whether activity of the matriptase stem is thereby modulated. Such a process may comprise (a) contacting the matriptase stem or a biologically active portion thereof with a candidate compound in a sample; and (b) comparing the activity of the matriptase stem or a biologically active portion thereof in said sample after contact with said candidate compound with the activity of the matriptase stem or a biologically active portion thereof in said sample before contact with said candidate compound, or with a reference level of activity.

The method of screening may be a method of screening for compounds that inhibit activity of the stem of matriptase.

The matriptase stem or a biologically active portion thereof may, for example be expressed on or by a cell. The matriptase stem or a biologically active portion thereof may, for example, be isolated from cells which express it. The matriptase stem or a biologically active portion thereof may, for example, be immobilised onto a solid phase.

There is also provided a method of screening for compounds that modulate the expression of the matriptase stem or nucleic acid encoding the stem of matriptase, the method comprising: (a) contacting cells expressing the matriptase stem or nucleic acid encoding the matriptase stem with a candidate compound; and (b) determining whether expression of the matriptase stem or nucleic acid encoding the matriptase stem is thereby modulated. Such a process may comprise (a) contacting cells expressing the matriptase stem or nucleic acid encoding the matriptase stem with a candidate compound in a sample; and (b) comparing the expression of the matriptase stem or nucleic acid encoding the matriptase stem by cells in said sample after contact with said candidate compound with the expression of the matriptase stem or nucleic acid encoding the matriptase stem of cells in said sample before contact with said candidate compound, or with a reference level of expression.

The method may be a method of screening for compounds that inhibit expression of the matriptase stem or nucleic acid encoding the stem of matriptase.

Other aspects of the invention include: a compound obtainable by an aforementioned screening method, a compound which modulates the activity or expression of the matriptase stem or nucleic acid encoding the stem of matriptase, for example a compound which inhibits the activity or expression of the matriptase stem or nucleic acid encoding the stem of matriptase.

Such a compound is provided for use in treating or preventing breast cancer, colorectal cancer, esophageal cancer, gastric cancer, prostate cancer or uterine cancer. There is also provided a method for treating or preventing breast cancer, colorectal cancer, esophageal cancer, gastric cancer, prostate cancer or uterine cancer which comprises administering to a subject in need thereof a therapeutically effective amount of such a compound.

Test compounds can be assayed for their ability to restore levels of the matriptase stem in a subject having breast cancer, colorectal cancer, esophageal cancer, gastric cancer, prostate cancer or uterine cancer towards levels found in subjects free from breast cancer, colorectal cancer, esophageal cancer, gastric cancer, prostate cancer and uterine cancer or to produce similar changes in experimental animal models of breast cancer, colorectal cancer, esophageal cancer, gastric cancer, prostate cancer or uterine cancer. Compounds able to restore levels of the matriptase stem in a subject having breast cancer, colorectal cancer, esophageal cancer, gastric cancer, prostate cancer or uterine cancer towards levels found in subjects free from breast cancer, colorectal cancer, esophageal cancer, gastric cancer, prostate cancer and uterine cancer or to produce similar changes in experimental animal models of breast cancer, colorectal cancer, esophageal cancer, gastric cancer, prostate cancer or uterine cancer can be used as lead compounds for further drug discovery, or used therapeutically. Expression of the matriptase stem can be assayed by the Preferred Technologies described herein, immunoassays, gel electrophoresis followed by visualization, detection of activity of the matriptase stem, or any other method taught herein or known to those skilled in the art. Such assays can be used to screen candidate drugs, in clinical monitoring or in drug development, where abundance of the matriptase stem can serve as a surrogate marker for clinical disease.

In various specific embodiments, in vitro assays can be carried out with cells representative of cell types involved in a subject's disorder, to determine if a compound has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Examples of animal models of breast cancer, colorectal cancer, esophageal cancer, gastric cancer, prostate cancer and uterine cancer include, but are not limited to xenografts of breast cancer cell lines such as MCF-7 (Ozzello L, Sordat M., Eur J. Cancer. 1980; 16:553-559) and MCF10AT (Miller et al., J Natl Cancer Inst. 1993; 85:1725-1732) in nude or SCID mice; xenografts of human colorectal cancer cell lines such as MDA-MB-345 in oestrogen-deprived SCID mice, Eccles et al. 1994 Cell Biophysics 24/25, 279; xenografts of gastric cell lines such as AZ-521 in nude mice; xenografts of prostate cancer cell lines such as CWR-22 in nude mice, Pretlow et al, J Natl Cancer Inst. 1993 Mar. 3; 85(5):394-8 or xenografts of cervical cancer cell lines such as CaSki in nude mice. These can be utilized to test compounds that modulate levels of the matriptase stem, since the pathology exhibited in these models is similar to that of breast cancer, colorectal cancer, esophageal cancer, gastric cancer, prostate cancer and uterine cancer. It is also apparent to the skilled artisan that based upon the present disclosure, transgenic animals can be produced with "knock-out" mutations of the gene or genes encoding the matriptase stem. A "knock-out" mutation of a gene is a mutation that causes the mutated gene to not be expressed, or expressed in an aberrant form or at a low level, such that the activity associated with the gene product is nearly or entirely absent. The transgenic animal is, for example, a mammal; such as a mouse.

In one embodiment, test compounds that modulate the expression of the matriptase stem are identified in non-human animals (e.g. mice, rats, monkeys, rabbits, and guinea pigs), preferably non-human animal models for breast cancer, colorectal cancer, esophageal cancer, gastric cancer, prostate cancer and uterine cancer, expressing the matriptase stem. In accordance with this embodiment, a test compound or a control compound is administered to the animals, and the effect of the test compound on expression of the matriptase stem is determined. A test compound that alters the expression of the matriptase stem can be identified by comparing the level of the matriptase stem (or mRNA encoding the same) in an animal or group of animals treated with a test compound with the level of the matriptase stem or mRNA in an animal or group of animals treated with a control compound. Techniques known to those of skill in the art can be used to determine the mRNA and protein levels, for example, in situ hybridization. The animals may or may not be sacrificed to assay the effects of a test compound.

In another embodiment, test compounds that modulate the activity of the matriptase stem or a biologically active portion thereof are identified in non-human animals (e.g. mice, rats, monkeys, rabbits, and guinea pigs), preferably non-human animal models for breast cancer, colorectal cancer, esophageal cancer, gastric cancer, prostate cancer and uterine cancer, expressing the matriptase stem. In accordance with this embodiment, a test compound or a control compound is administered to the animals, and the effect of a test compound on the activity of the matriptase stem is determined. A test compound that alters the activity of the matriptase stem can be identified by assaying animals treated with a control compound and animals treated with the test compound. The activity of the matriptase stem can be assessed by detecting induction of a cellular second messenger of the matriptase stem (e.g. intracellular $Ca^{2+}$, diacylglycerol, IP3, etc.), detecting catalytic or enzymatic activity of the matriptase stem or binding partner thereof, detecting the induction of a reporter gene (e.g. a regulatory element that is responsive to the matriptase stem operably linked to a nucleic acid encoding a detectable marker, such as luciferase or green fluorescent protein), or detecting a cellular response (e.g. cellular differentiation or cell proliferation). Techniques known to those of skill in the art can be utilized to detect changes in the activity of the matriptase stem (see e.g. U.S. Pat. No. 5,401,639, which is incorporated herein by reference).

In yet another embodiment, test compounds that modulate the level or expression of the matriptase stem are identified in human subjects having breast cancer, colorectal cancer, esophageal cancer, gastric cancer, prostate cancer or uterine cancer, particularly those having severe breast cancer, colorectal cancer, esophageal cancer, gastric cancer, prostate cancer or uterine cancer. In accordance with this embodiment, a test compound or a control compound is administered to the human subject, and the effect of a test compound on expression of the matriptase stem is determined by analysing the expression of the matriptase stem or the mRNA encoding the same in a biological sample. A test compound that alters the expression of the matriptase stem can be identified by comparing the level of the matriptase stem or mRNA encoding the same in a subject or group of subjects treated with a control compound to that in a subject or group of subjects treated with a test compound. Alternatively, alterations in the expression of the matriptase stem can be identified by comparing the level of the matriptase stem or mRNA encoding the same in a subject or group of subjects before and after the administration of a test compound. Techniques known to those of skill in the art can be used to obtain the biological sample and analyse the mRNA or protein expression. For example, the Preferred Technologies described herein can be used to assess changes in the level of the matriptase stem.

In another embodiment, test compounds that modulate the activity of the matriptase stem are identified in human subjects having breast cancer, colorectal cancer, esophageal cancer, gastric cancer, prostate cancer or uterine cancer (particularly those with severe breast cancer, colorectal cancer, esophageal cancer, gastric cancer, prostate cancer or uterine cancer). In this embodiment, a test compound or a control compound is administered to the human subject, and the effect of a test compound on the activity of the matriptase stem is determined. A test compound that alters the activity of the matriptase stem can be identified by comparing biological samples from subjects treated with a control compound to samples from subjects treated with the test compound. Alternatively, alterations in the activity of the matriptase stem can be identified by comparing the activity of the matriptase stem in a subject or group of subjects before and after the administration of a test compound. The activity of the matriptase stem can be assessed by detecting in a biological sample induction of a cellular signal transduction pathway of the matriptase stem (e.g. intracellular $Ca^{2+}$, diacylglycerol, IP3, etc.), catalytic or enzymatic activity of the matriptase stem or a binding partner thereof, or a cellular response, for example, cellular differentiation, or cell proliferation. Techniques known to those of skill in the art can be used to detect changes in the induction of a second messenger of the matriptase stem or changes in a cellular response. For example, RT-PCR can be used to detect changes in the induction of a cellular second messenger.

In another embodiment, a test compound that changes the level or expression of the matriptase stem towards levels detected in control subjects (e.g. humans free from breast cancer, colorectal cancer, esophageal cancer, gastric cancer, prostate cancer and uterine cancer) is selected for further testing or therapeutic use. In another embodiment, a test compound that changes the activity of the matriptase stem towards the activity found in control subjects (e.g. humans free from breast cancer, colorectal cancer, esophageal cancer, gastric cancer, prostate cancer and uterine cancer) is selected for further testing or therapeutic use.

In another embodiment, test compounds that reduce the severity of one or more symptoms associated with breast cancer, colorectal cancer, esophageal cancer, gastric cancer, prostate cancer or uterine cancer are identified in human subjects having breast cancer, colorectal cancer, esophageal cancer, gastric cancer, prostate cancer or uterine cancer, preferably subjects with severe breast cancer, colorectal cancer, esophageal cancer, gastric cancer, prostate cancer or uterine cancer. In accordance with this embodiment, a test compound or a control compound is administered to the subjects, and the effect of a test compound on one or more symptoms of breast cancer, colorectal cancer, esophageal cancer, gastric cancer, prostate cancer or uterine cancer is determined. A test compound that reduces one or more symptoms can be identified by comparing the subjects treated with a control compound to the subjects treated with the test compound. Techniques known to physicians familiar with breast cancer, colorectal cancer, esophageal cancer, gastric cancer, prostate cancer or uterine cancer can be used to determine whether a test compound reduces one or more symptoms associated with breast cancer, colorectal cancer, esophageal cancer, gastric cancer, prostate cancer or uterine cancer. For example, a test compound that reduces tumour burden in a subject having breast cancer, colorectal cancer, esophageal cancer, gastric cancer, prostate cancer or uterine cancer will be beneficial for subjects having breast cancer, colorectal cancer, esophageal cancer, gastric cancer, prostate cancer or uterine cancer.

In another embodiment, a test compound that reduces the severity of one or more symptoms associated with breast cancer, colorectal cancer, esophageal cancer, gastric cancer, prostate cancer or uterine cancer in a human having breast cancer, colorectal cancer, esophageal cancer, gastric cancer, prostate cancer or uterine cancer is selected for further testing or therapeutic use.

Therapeutic and Prophylactic Compositions and their Use

The invention provides methods of treatment (and prophylaxis) comprising administering to a subject an effective amount of a compound of the invention. In a particular aspect, the compound is substantially purified (e.g. substantially free from substances that limit its effect or produce undesired side-effects). The subject is, for example, an animal, including but not limited to animals such as cows, pigs, horses, chickens, cats, dogs etc., and is, for example, a mammal, such as a human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g. encapsulation in liposomes, microparticles, microcapsules, recombinant cells capable of expressing the compound, receptor-mediated endocytosis (see e.g. Wu and Wu, 1987, J. Biol. Chem. 262: 4429-4432), construction of a nucleic acid as part of a retroviral or other vector etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g. oral mucosa, rectal and intestinal mucosa etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed e.g. by use of an inhaler or nebulizer, and formulation with an aerosolizing agent.

In one aspect of the invention a nucleic acid employed in the invention may be delivered to the dermis, for example employing particle mediated epidermal delivery.

In a specific embodiment, it may be desirable to administer the pharmaceutical compositions of the invention locally to the area in need of treatment; this may be achieved, for example, and not by way of limitation, by local infusion during surgery, topical application, e.g. by injection, by means of a catheter, or by means of an implant, said implant being of a porous, non-porous, or gelatinous material, including membranes, such as sialastic membranes, or fibers. In one embodiment, administration can be by direct injection into breast, colorectal, esophageal, gastric, prostate or uterine tissue or at the site (or former site) of a malignant tumor or neoplastic or pre-neoplastic tissue.

In another embodiment, the compound can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target i.e. the breast, colon, esophagus, stomach, prostate or uterus, thus requiring only a fraction of the systemic dose (see e.g. Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular e.g. by use of a retroviral vector (see U.S. Pat. No. 4,980,286), or by direct injection, or by use of microparticle bombardment (e.g. a gene gun; Biolistic, Dupont), or coating with lipids or cell-surface receptors or transfecting agents, or by administering it in linkage to a homeobox-like peptide which is known to enter the nucleus (see e.g. Joliot et al., 1991, Proc. Natl. Acad. Sci. USA 88:1864-1868) etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In one embodiment, for example where one or more antibodies are employed, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids etc., and those formed with free carboxyl groups such as those derived from sodium, potassium, ammonium, calcium, ferric hydroxides, isopropylamine, triethylamine, 2-ethylamino ethanol, histidine, procaine etc.

The amount of the compound of the invention which will be effective in the treatment of breast cancer, colorectal cancer, esophageal cancer, gastric cancer, prostate cancer or uterine cancer can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Thus, in one aspect the kit comprises antibodies employed in the invention, for example the antibodies may be lyophilized for reconstitution before administration or use. Where the kit is for use in therapy/treatment such as cancer the antibody or antibodies may be reconstituted with an isotonic aqueous solution, which may optionally be provided with the kit. In one aspect the kit may comprise a polypeptide such as an immunogenic polypeptide employed in the invention, which may for example be lyophilized. The latter kit may further comprise an adjuvant for reconstituting the immunogenic polypeptide.

The invention also extends to a composition as described herein for example a pharmaceutical composition and/or vaccine composition for use in inducing an immune response in a subject.

Determining Abundance of the Matriptase Stem by Imaging Technology

An advantage of determining abundance of the matriptase stem by imaging technology may be that such a method is non-invasive (save that reagents may need to be administered) and there is no need to extract a sample from the subject.

Suitable imaging technologies include positron emission tomography (PET) and single photon emission computed tomography (SPECT). Visualisation of the matriptase stem using such techniques requires incorporation or binding of a suitable label e.g. a radiotracer such as $^{18}F$, $^{11}C$ or $^{123}I$ (see e.g. NeuroRs—The Journal of the American Society for Experimental NeuroTherapeutics (2005) 2(2), 348-360 and idem pages 361-371 for further details of the techniques). Radiotracers or other labels may be incorporated into the matriptase stem by administration to the subject (e.g. by injection) of a suitably labelled specific ligand. Alternatively they may be incorporated into a binding affinity reagent (e.g. an antibody) specific for the matriptase stem which may be administered to the subject (e.g. by injection). For discussion of use of Affibodies for imaging see e.g. Orlova A, Magnusson M, Eriksson T L, Nilsson M, Larsson B, Hoiden-Guthenberg I, Widstrom C, Carlsson J, Tolmachev V, Stahl S, Nilsson F Y, Tumor imaging using a picomolar affinity HER2 binding affibody molecule, Cancer Res. 2006 Apr. 15; 66(8):4339-48. Diagnosis and Treatment of Breast Cancer, Colorectal Cancer, Esophageal Cancer, Gastric Cancer, Prostate Cancer or Uterine Cancer Using Immunohistochemistry Immunohistochemistry is an excellent detection technique and may therefore be very useful in the diagnosis and treatment of breast cancer, colorectal cancer, esophageal cancer, gastric cancer, prostate cancer or uterine cancer. Immunohistochemistry may be used to detect, diagnose, or monitor breast cancer, colorectal cancer, esophageal cancer, gastric cancer, prostate cancer or uterine cancer through the localization of antigens of the matriptase stem in tissue sections by the use of labeled antibodies (or other affinity reagents), derivatives and analogs thereof, which specifically bind to the matriptase stem, as specific reagents through antigen-antibody interactions that are visualized by a marker such as fluorescent dye, enzyme, radioactive element or colloidal gold.

The advancement of monoclonal antibody technology has been of great significance in assuring the place of immunohistochemistry in the modern accurate microscopic diagnosis of human neoplasms. The identification of disseminated neoplastically transformed cells by immunohistochemistry allows for a clearer picture of cancer invasion and metastasis, as well as the evolution of the tumour cell associated immunophenotype towards increased malignancy. Future antineoplastic therapeutical approaches may include a variety of individualized immunotherapies, specific for the particular immunophenotypical pattern associated with each individual patient's neoplastic disease. For further discussion see e.g. Bodey B. The significance of immunohistochemistry in the diagnosis and therapy of neoplasms, Expert Opin Biol Ther. 2002 April; 2(4):371-93.

The present invention may also be understood by reference to the following numbered paragraphs:
1. An isolated antibody or other affinity reagent such as an Affibody, Nanobody or Unibody capable of immunospecific binding to the matriptase stem that remains on the cell surface.
2. An isolated antibody or other affinity reagent such as an Affibody, Nanobody or Unibody as defined in paragraph 1, wherein the matriptase stem is defined by any one of SEQ ID Nos 10-13.
3. An isolated antibody or other affinity reagent such as an Affibody, Nanobody or Unibody capable of immunospecific binding to the matriptase stem according to paragraph 1 or paragraph 2 which is conjugated to a diagnostic moiety.
4. An isolated antibody or other affinity reagent such as an Affibody, Nanobody or Unibody capable of immunospecific binding to the matriptase stem according to paragraph 1 or paragraph 2 which is conjugated to a therapeutic moiety.
5. A kit comprising an antibody or other affinity reagent such as an Affibody, Nanobody or Unibody as defined in paragraphs 1-4.
6. A kit comprising a plurality of distinct antibodies or other affinity reagents such as Affibodies, Nanobodies or Unibodies as defined in paragraphs 1-4.
7. A pharmaceutical composition comprising a therapeutically effective amount of an antibody or other affinity reagent such as an Affibody, Nanobody or Unibody as defined in paragraph 1, 2 or 4, or a fragment or derivative thereof which comprises the binding domain of the affinity reagent, and optionally a pharmaceutically acceptable carrier.
8. A method of treating or preventing breast cancer, colorectal cancer, esophageal cancer, gastric cancer, prostate cancer or uterine cancer comprising administering to a subject an antibody or other affinity reagent such as an Affibody, Nanobody or Unibody as defined in paragraph 1, 2 or 4, or a fragment or derivative thereof which comprises the binding domain of the affinity reagent.
9. The use of an antibody or other affinity reagent such as an Affibody, Nanobody or Unibody as defined in paragraph 1, 2 or 4, a fragment or derivative thereof which comprises the binding domain of the affinity reagent in the manufacture of a medicament for the treatment of breast cancer, colorectal cancer, esophageal cancer, gastric cancer, prostate cancer or uterine cancer.
10. A method of determining the availability of the matriptase stem as a therapeutic target in a subject, the method comprising:
    (a) performing assays configured to detect the soluble catalytic domain of matriptase in one or more samples obtained from said subject; and
    (b) correlating the results of said assay(s) to the presence or absence of the stem of matriptase.
11. A method according to paragraph 10 wherein the soluble catalytic domain of matriptase is defined by SEQ ID No: 14.
12. A method of treating or preventing breast cancer, colorectal cancer, esophageal cancer, gastric cancer, prostate cancer or uterine cancer comprising administering to a subject in need of such treatment or prevention a therapeutically effective amount of nucleic acid encoding the matriptase stem or one or more fragments or derivatives thereof, for example in the form of a vaccine.
13. A method of treating or preventing breast cancer, colorectal cancer, esophageal cancer, gastric cancer, prostate cancer or uterine cancer comprising administering to a subject in need of such treatment or prevention a therapeutically effective amount of nucleic acid that inhibits the function or expression of the stem of matriptase.
14. The method of paragraph 13, wherein the nucleic acid is an anti-sense nucleic acid or ribozyme of the stem of matriptase.
15. The use of nucleic acid encoding the matriptase stem or one or more fragments or derivatives thereof, in the manufacture of a medicament for treating or preventing breast cancer, colorectal cancer, esophageal cancer, gastric cancer, prostate cancer or uterine cancer.
16. The use of nucleic acid that inhibits the function or expression of the stem of matriptase, in the manufacture of a medicament for treating or preventing breast cancer, colorectal cancer, esophageal cancer, gastric cancer, prostate cancer or uterine cancer.
17. The use of paragraph 16, wherein the nucleic acid is an anti-sense nucleic acid or ribozyme of the stem of matriptase.
18. A method of detecting, diagnosing and/or screening for breast cancer, colorectal cancer, esophageal cancer, gastric cancer, prostate cancer or uterine cancer which comprises:
    (a) bringing into contact with a sample to be tested the stem of matriptase, or one or more antigenic or immunogenic fragments thereof; and
    (b) detecting the presence of antibodies (or other affinity reagents such as Affibodies, Nanobodies or Unibodies) in the sample capable of specific binding to the stem of matriptase, or one or more antigenic or immunogenic fragments thereof.
19. The use of the matriptase stem and/or one or more antigenic or immunogenic fragments thereof, in screening for, detecting and/or diagnosing breast cancer, colorectal cancer, esophageal cancer, gastric cancer, prostate cancer or uterine cancer.
20. A kit for use in the screening for, detection and/or diagnosis of breast cancer, colorectal cancer, esophageal cancer, gastric cancer, prostate cancer or uterine cancer, which kit comprises the matriptase stem and/or one or more antigenic or immunogenic fragments thereof.

21. A method for screening for and/or diagnosis of breast cancer, colorectal cancer, esophageal cancer, gastric cancer, prostate cancer or uterine cancer in a human subject, which comprises the step of identifying the presence or absence of the stem of matriptase, or a fragment thereof, in a biological sample obtained from said human subject.

22. A method for monitoring and/or assessing breast cancer, colorectal cancer, esophageal cancer, gastric cancer, prostate cancer or uterine cancer treatment in a human subject, which comprises the step of identifying the presence or absence of the stem of matriptase, or a fragment thereof, in a biological sample obtained from said human subject.

23. A method for identifying the presence or absence of metastatic breast cancer, colorectal cancer, esophageal cancer, gastric cancer, prostate cancer or uterine cancer cells in a biological sample obtained from a human subject, which comprises the step of identifying the presence or absence of the stem of matriptase, or a fragment thereof.

24. A method for monitoring and/or assessing breast cancer, colorectal cancer, esophageal cancer, gastric cancer, prostate cancer or uterine cancer treatment in a human subject, which comprises the step of determining whether the stem of matriptase, or a fragment thereof, is increased/decreased in a biological sample obtained from a patient.

25. A method as defined in any one of paragraphs 21 to 24, wherein the method comprises an immunoassay step utilising one or more antibodies or other affinity reagents such as Affibodies, Nanobodies or Unibodies against the stem of matriptase, or a fragment or derivative, thereof, said affinity reagents optionally being conjugated to a diagnostic moiety.

26. A method as defined in any one of paragraphs 21 to 24, wherein the method comprises the use of nucleic acid probes and/or PCR reactions to amplify nucleic acid coding for the stem of matriptase.

27. A method as defined in any one of paragraphs 21 to 24, wherein a whole body scan of the subject is carried out to determine localisation of breast cancer, colorectal cancer, esophageal cancer, gastric cancer, prostate cancer or uterine cancer cells, particularly metastatic breast cancer, colorectal cancer, esophageal cancer, gastric cancer, prostate cancer or uterine cancer cells.

28. A method as defined in paragraph 27, wherein labelled antibodies or other affinity reagents such as Affibodies, Nanobodies or Unibodies are employed, said affinity reagents optionally being conjugated to a diagnostic moiety.

29. A diagnostic kit comprising one or more reagents for use in the detection and/or determination of the stem of matriptase, or a fragment thereof.

30. A kit as defined in paragraph 29, which comprises one or more containers with one or more antibodies or other affinity reagents such as Affibodies, Nanobodies or Unibodies against the stem of matriptase, or a fragment thereof, said affinity reagents optionally being conjugated to a diagnostic moiety.

31. A kit as defined in paragraph 30, which further comprises a labelled binding partner to the or each affinity reagent and/or a solid phase (such as a reagent strip) upon which the or each affinity reagent is/are immobilised.

32. A kit as defined in paragraph 30 which comprises a nucleic acid probe capable of hybridizing to DNA or RNA encoding the stem of matriptase, or a fragment thereof.

33. A method for screening, diagnosis or prognosis of breast cancer, colorectal cancer, esophageal cancer, gastric cancer, prostate cancer or uterine cancer in a subject or for monitoring the effect of an anti-breast cancer, an anti-colorectal cancer, an anti-esophageal cancer, an anti-gastric cancer, an anti-prostate cancer or an anti-uterine cancer drug or therapy administered to a subject, comprising:
   (a) analysing a sample from the subject by a protein separation technique, for example one dimensional electrophoresis, to generate a one-dimensional array of features; and
   (b) for at least one chosen feature whose relative abundance correlates with the presence or absence of breast cancer, colorectal cancer, esophageal cancer, gastric cancer, prostate cancer or uterine cancer, comparing the abundance of each such chosen feature in the sample with the abundance of that chosen feature in a sample from one or more persons free from breast cancer, colorectal cancer, esophageal cancer, gastric cancer, prostate cancer and uterine cancer, or with a previously determined reference range,
wherein the relative abundance of the chosen feature or features in the sample indicates the presence or absence of breast cancer, colorectal cancer, esophageal cancer, gastric cancer, prostate cancer or uterine cancer in the subject.

34. The method of paragraph 33, wherein step (b) comprises quantitatively detecting the stem of matriptase.

35. A method for screening, diagnosis or prognosis of breast cancer, colorectal cancer, esophageal cancer, gastric cancer, prostate cancer or uterine cancer in a subject or for monitoring the effect of an anti-breast cancer, an anti-colorectal cancer, an anti-esophageal cancer, an anti-gastric cancer, an anti-prostate cancer or an anti-uterine cancer drug or therapy administered to a subject, comprising: in a sample from the subject, quantitatively detecting the stem of matriptase.

36. The method of any one of paragraphs 33 to 35, wherein the sample is a sample of breast, colorectal, esophageal, gastric, prostate or uterine tissue.

37. The method according to paragraph 35 or paragraph 36, wherein the step of quantitatively detecting comprises testing the sample, said step of testing comprising:
   (a) contacting the sample with an isolated antibody or other affinity reagent such as an Affibody, Nanobody or Unibody that is immunospecific for the matriptase stem said affinity reagent optionally being conjugated to a diagnostic moiety; and
   (b) detecting whether binding has occurred between the affinity reagent and at least one species in the sample.

38. The method according to paragraph 37, wherein the step of quantitatively detecting comprises testing the sample, said step of testing comprising:
   (a) contacting the sample with a capture reagent to capture the stem of matriptase; and
   (b) detecting the captured matriptase stem using a directly or indirectly labelled detection reagent.

39. The method according to paragraph 38, wherein the capture reagent is an isolated antibody or other affinity reagent such as an Affibody, Nanobody or Unibody.

40. The method according to paragraph 38 or paragraph 39, wherein the matriptase stem is in the form of a particular isoform and the capture reagent recognises the component part of that isoform which distinguishes the isoform from other members of the gene family, e.g. lectin for carbohydrate, or phosphotyrosine or phosphoserine/threonine Ab, or methylation or acetylation Ab.

41. The method according to any one of paragraphs 37 to 39, wherein the affinity reagent is a monoclonal antibody.

42. A method of screening for compounds that interact with the matriptase stem or biologically active portion thereof, the method comprising:
   (a) contacting the matriptase stem or biologically active portion thereof with a candidate compound; and
   (b) determining the ability of the candidate compound to interact with the matriptase stem or biologically active portion thereof.

43. A method of screening for or identifying compounds that modulate the activity of the matriptase stem or biologically active portion thereof, the method comprising:
   (a) in a first aliquot, contacting a candidate compound with the matriptase stem or biologically active portion thereof; and
   (b) comparing the activity of the matriptase stem or biologically active portion thereof in the first aliquot after addition of the candidate compound with the activity of the matriptase stem or biologically active portion thereof in a control aliquot, or with a previously determined reference range.

44. The method of paragraph 42 or 43, wherein the matriptase stem or biologically active portion thereof is expressed by a cell.

45. The method of paragraph 42, 43 or 44, wherein the matriptase stem or biologically active portion thereof is recombinant 46. The method of paragraph 45, wherein the polypeptide or biologically active portion thereof is immobilised on a solid phase.

47. A method of screening for compounds that modulate the expression or activity of the stem of matriptase, comprising:
   (a) contacting an enzyme which is responsible for the production or degradation of the matriptase stem with a candidate compound;
   (b) detecting modulation of the activity of said enzyme.

48. A method of screening for compounds that modulate the expression or activity of the stem of matriptase, comprising:
   (a) contacting a first group of cells expressing the matriptase stem with a candidate compound;
   (b) contacting a second group of cells expressing the matriptase stem with a control compound; and
   (c) comparing the level of the matriptase stem or mRNA encoding the matriptase stem in the first and second groups of cells, or comparing the level of induction of a cellular second messenger in the first and second groups of cells.

49. A method of screening for or identifying compounds that modulate the expression or activity of the stem of matriptase, the method comprising:
   (a) administering a candidate compound to a first group of mammals;
   (b) administering a control compound to a second group of mammals; and
   (c) comparing the level of expression of the matriptase stem or of mRNA encoding the matriptase stem in the first and second groups, or comparing the level of induction of a cellular second messenger in the first and second groups.

50. The method of paragraph 49, wherein the mammals are animal models for breast cancer, colorectal cancer, esophageal cancer, gastric cancer, prostate cancer or uterine cancer.

51. A method for screening, diagnosis or prognosis of breast cancer, colorectal cancer, esophageal cancer, gastric cancer, prostate cancer or uterine cancer in a subject or for monitoring the effect of an anti-breast cancer, an anti-colorectal cancer, an anti-esophageal cancer, an anti-gastric cancer, an anti-prostate cancer or an anti-uterine cancer drug or therapy administered to a subject, comprising:
   (a) contacting one or more oligonucleotide probes comprising 10 or more consecutive nucleotides complementary to a nucleotide sequence encoding the stem of matriptase, with an RNA obtained from a biological sample from the subject or with cDNA copied from the RNA, wherein said contacting occurs under conditions that permit hybridization of the probe to the nucleotide sequence if present;
   (b) detecting hybridization, if any, between the probe and the nucleotide sequence; and
   (c) comparing the hybridization, if any, detected in step (b) with the hybridization detected in a control sample, or with a previously determined reference range.

52. The use of an agent which interacts with, or modulates the activity of the matriptase stem in the manufacture of a medicament for the treatment of breast cancer, colorectal cancer, esophageal cancer, gastric cancer, prostate cancer or uterine cancer.

53. A method for the treatment or prophylaxis of breast cancer, colorectal cancer, esophageal cancer, gastric cancer, prostate cancer or uterine cancer in a subject, or of vaccinating a subject against breast cancer, colorectal cancer, esophageal cancer, gastric cancer, prostate cancer or uterine cancer, which comprises the step of administering to the subject an effective amount of the matriptase stem and/or one or more antigenic or immunogenic fragments thereof, preferably as a vaccine.

54. The use of the stem of matriptase, one or more fragments or derivatives thereof, or one or more fragments or derivatives thereof, in the manufacture of a medicament for the treatment or prophylaxis of breast cancer, colorectal cancer, esophageal cancer, gastric cancer, prostate cancer or uterine cancer.

55. A vaccine comprising the matriptase stem or derivatives thereof, and/or one or more antigenic or immunogenic fragments thereof.

56. A composition capable of eliciting an immune response in a subject, which composition comprises the matriptase stem and/or one or more antigenic or immunogenic fragments thereof, and one or more suitable adjuvants.

57. The use of a composition as defined in paragraph 56 in inducing an immune response in a subject.

58. A method according to any one of the preceding paragraphs wherein the method of determining the abundance of the stem of matriptase, for example a method of quantitatively detecting the stem of matriptase, involves use of an imaging technology.

59. A method according to paragraph 58 wherein the imaging technology involves use of labelled Affibodies.

60. A method according to paragraph 58 wherein the imaging technology involves use of labelled antibodies.

61. A method for identifying the presence of breast cancer, colorectal cancer, esophageal cancer, gastric cancer, prostate cancer or uterine cancer in a subject which comprises the step of carrying out immunohistochemistry to determine the localisation of breast cancer, colorectal cancer, esophageal cancer, gastric cancer, prostate cancer or uterine cancer cells, particularly metastatic breast cancer, colorectal cancer, esophageal cancer, gastric cancer, prostate cancer or uterine cancer cells, in tissue sections, by the use of labeled antibodies, or other affinity reagents such as Affibodies, Nanobodies or Unibodies, derivatives and analogs thereof, capable of specific binding to the matriptase stem or one or more antigenic or immunogenic fragments thereof, in order to determine presence or amount of the stem of matriptase, wherein the presence or amount of the matriptase stem indicates the presence of breast cancer, colorectal cancer, esophageal cancer, gastric cancer, prostate cancer or uterine cancer in the subject.

62. A process for preparing a monoclonal antibody which is capable of immunospecific binding to the matriptase stem which comprises the step of immunising a non-human animal with a protein which is the matriptase stem or an immunogenic fragment thereof or a fusion protein containing the matriptase stem or an immunogenic fragment thereof or immunising a non-human animal with cells which express such a protein in either case optionally together with an immunostimulant.

63. A process according to paragraph 62 wherein the non-human animal is immunised with a fusion protein or cells which express said protein.

64. A process according to paragraph 62 or 63 which further comprises the step of isolating antibody producing cells from said animal and immortalising them by fusing them with immortal cells to produce an antibody-producing hybridoma.

65. A process according to paragraph 64 which further comprises the step of isolating antibodies from said hybridoma.

66. An isolated monoclonal antibody which is capable of immunospecific binding to the matriptase stem obtainable by the process of any one of paragraphs 62-65.

67. An isolated monoclonal antibody according to paragraph 66 which is a human monoclonal antibody by virtue of the non-human animal being transgenic and adapted to express human immunoglobulin heavy and light chain genes and not endogenous immunoglobulin heavy and light chain genes.

68. An isolated humanised monoclonal antibody which is capable of immunospecific binding to the matriptase stem characterised by having one or more CDRs of a monoclonal antibody obtainable by the process of any one of paragraphs 62-65.

69. A fragment or derivative of a monoclonal antibody according to any one of paragraphs 66-68 which is capable of immunospecific binding to the stem of matriptase.

Preferred features of each aspect of the invention are as for each of the other aspects *mutatis mutandis*. The prior art documents mentioned herein are incorporated to the fullest extent permitted by law.

EXAMPLE 1

Identification of Membrane Proteins Expressed in Breast Cancer and Colorectal Cancer Tissue Samples Using the following Reference Protocol, membrane proteins extracted from breast cancer and colorectal cancer tissue samples were separated by 1D gel and analysed.
1.1 Materials and Methods
1.1.1—Plasma Membrane Fractionation The cells recovered from the epithelium of a breast cancer or colorectal cancer were lysed and submitted to centrifugation at 1000 G. The supernatant was taken, and it was subsequently centrifuged at 3000 G. Once again, the supernatant was taken, and it was then centrifuged at 100,000 G.

The resulting pellet was recovered and centrifugally fractionated on a 15-60% sucrose gradient.

A Western blot was used to identify sub cellular markers, and the Plasma Membrane enriched fractions were pooled.

The pooled solution was either applied directly to 1D gels (see section 1.1.4 below), or further fractionated into heparin binding and nucleotide binding fractions as described below.
1.1.2—Plasma Membrane Heparin-Binding Fraction The pooled solution from 1.1.1 above was applied to a Heparin column, eluted from the column and electrophoretically fractionated on 1D polyacrylamide gels (see section 1.1.4 below).
1.1.3—Plasma Nucleotide-Binding Fraction The pooled solution from 1.1.1 above was applied to a Cibacrom Blue 3GA column, eluted from column and electrophoretically fractionated on 1D polyacrylamide gels (see section 1.1.4 below).
1.1.4—1D gel technology Protein or membrane pellets were solubilised in 1D sample buffer (1-2 µg/µl). The sample buffer and protein mixture was then heated to 95° C. for 3 min.

A 9-16% polyacrylamide gradient gel was cast with a stacking gel and a stacking comb according to the procedure described in Ausubel F. M. et al., eds., 1989, Current Protocols in Molecular Biology, Vol. II, Green Publishing Associates, Inc., and John Wiley & Sons, Inc., New York, section 10.2, incorporated herein by reference in its entirety.

30-50 micrograms of the protein mixtures obtained from detergent extracts and molecular weight standards (66, 45, 31, 21, 14 kDa) were added to the stacking gel wells using a 10 microliter pipette tip and the samples electrophorectically fractionated in the gel at 40 mA for 5 hours.

The plates were then opened, the gel placed in a tray of fixer (10% acetic acid, 40% ethanol, 50% water) and shaken overnight. Following this, the gel was primed by 30 minutes shaking in a primer solution (7.5% acetic acid (75 ml), 0.05% SDS (5 ml of 10%)). The gel was then incubated with a fluorescent dye (7.5% acetic acid, 0.06% OGS in-house dye (600 µl) with shaking for 3 hrs. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety.

A computer-readable output was produced by imaging the fluorescently stained gels with an Apollo 3 scanner (Oxford Glycosciences, Oxford, UK). This scanner is developed from the scanner described in WO 96/36882 and in the Ph.D. thesis of David A. Basiji, entitled "Development of a High-throughput Fluorescence Scanner Employing Internal Reflection Optics and Phase-sensitive Detection (Total Internal Reflection, Electrophoresis)", University of Washington (1997), Volume 58/12-B of Dissertation Abstracts International, page 6686, the contents of each of which are incorporated herein by reference. The latest embodiment of this instrument includes the following improvements: The gel is transported through the scanner on a precision lead-screw drive system. This is preferable to laying the glass plate on the belt-driven system that is defined in the Basiji thesis as it provides a reproducible means of accurately transporting the gel past the imaging optics.

The gel is secured into the scanner against three alignment stops that rigidly hold the glass plate in a known position. By doing this in conjunction with the above precision transport system and the fact that the gel is bound to the glass plate, the absolute position of the gel can be predicted and recorded. This ensures that accurate co-ordinates of each feature on the gel can be communicated to the cutting robot for excision. This cutting robot has an identical mounting arrangement for the glass plate to preserve the positional accuracy.

The carrier that holds the gel in place has integral fluorescent markers (Designated M1, M2, M3) that are used to correct the image geometry and are a quality control feature to confirm that the scanning has been performed correctly.

The optical components of the system have been inverted. The laser, mirror, waveguide and other optical components are now above the glass plate being scanned. The embodiment of the Basiji thesis has these underneath. The glass plate is therefore mounted onto the scanner gel side down, so that the optical path remains through the glass plate. By doing this, any particles of gel that may break away from the glass plate will fall onto the base of the instrument rather than into the optics.

In scanning the gels, they were removed from the stain, rinsed with water and allowed to air dry briefly and imaged on the Apollo 3. After imaging, the gels were sealed in polyethylene bags containing a small volume of staining solution, and then stored at 4° C.

Apparent molecular weights were calculated by interpolation from a set of known molecular weight markers run alongside the samples.

1.1.5—Recovery and analysis of selected proteins

Proteins were robotically excised from the gels by the process described in U.S. Pat. No. 6,064,754, Sections 5.4 and 5.6, 5.7, 5.8 (incorporated herein by reference), as is applicable to 1D-electrophoresis, with modification to the robotic cutter as follows: the cutter begins at the top of the lane, and cuts a gel disc 1.7 mm in diameter from the left edge of the lane. The cutter then moves 2 mm to the right, and 0.7 mm down and cuts a further disc. This is then repeated. The cutter then moves back to a position directly underneath the first gel cut, but offset by 2.2 mm downwards, and the pattern of three diagonal cuts are repeated. This is continued for the whole length of the gel.

NOTE: If the lane is observed to broaden significantly then a correction can be made also sideways i.e. instead of returning to a position directly underneath a previous gel cut, the cut can be offset slightly to the left (on the left of the lane) and/or the right (on the right of the lane). The proteins contained within the gel fragments were processed to generate tryptic peptides; partial amino acid sequences of these peptides were determined by mass spectroscopy as described in WO98/53323 and application Ser. No. 09/094,996, filed Jun. 15, 1998.

Proteins were processed to generate tryptic digest peptides. Tryptic peptides were analysed by mass spectrometry using a PerSeptive Biosystems Voyager—DETM STR Matrix-Assisted Laser Desorption Ionization Time-of-Flight (MALDI-TOF) mass spectrometer, and selected tryptic peptides were analysed by tandem mass spectrometry (MS/MS) using a Micromass Quadrupole Time-of-Flight (Q-TOF) mass spectrometer (Micromass, Altrincham, U.K.) equipped with a Nanoflow™ electrospray Z-spray source. For partial amino acid sequencing and identification of matriptase, uninterpreted tandem mass spectra of tryptic peptides were searched using the SEQUEST search program (Eng et al., 1994, J. Am. Soc. Mass Spectrom. 5:976-989), version v.C.1. Criteria for database identification included: the cleavage specificity of trypsin; the detection of a suite of a, b and y ions in peptides returned from the database, and a mass increment for all Cys residues to account for carbamidomethylation. The database searched was a database constructed of protein entries in the non-redundant database held by the National Centre for Biotechnology Information (NCBI) which is accessible at www.ncbi.nlm.nih.gov. Following identification of proteins through spectral-spectral correlation using the SEQUEST program, masses detected in MALDI-TOF mass spectra were assigned to tryptic digest peptides within the proteins identified. In cases where no amino acid sequences could be identified through searching with uninterpreted MS/MS spectra of tryptic digest peptides using the SEQUEST program, tandem mass spectra of the peptides were interpreted manually, using methods known in the art. (In the case of interpretation of low-energy fragmentation mass spectra of peptide ions see Gaskell et al., 1992, Rapid Commun Mass Spectrom. 6:658-662).

1.1.6—Discrimination of Breast Cancer and Colorectal Cancer Associated Proteins

The process to identify matriptase uses the peptide sequences obtained experimentally by mass spectrometry described above of naturally occurring human proteins to identify and organise coding exons in the published human genome sequence.

Recent dramatic advances in defining the chemical sequence of the human genome have led to the near completion of this immense task (Venter, J. C. et al. (2001). The sequence of the human genome. Science 16: 1304-51; International Human Genome Sequencing Consortium. (2001). Initial sequencing and analysis of the human genome Nature 409: 860-921). There is little doubt that this sequence information will have a substantial impact on our understanding of many biological processes, including molecular evolution, comparative genomics, pathogenic mechanisms and molecular medicine. For the full medical value inherent in the sequence of the human genome to be realised, the genome needs to be 'organised' and annotated. By this, is meant at least the following three things: (i) The assembly of the sequences of the individual portions of the genome into a coherent, continuous sequence for each chromosome. (ii) The unambiguous identification of those regions of each chromosome that contain genes. (iii) Determination of the fine structure of the genes and the properties of its mRNA and protein products. While the definition of a 'gene' is an increasingly complex issue (H Pearson: What is a gene? Nature (2006) 24: 399-401), what is of immediate interest for drug discovery and development is a catalogue of those genes that encode functional, expressed proteins. A subset of these genes will be involved in the molecular basis of most if not all pathologies. Therefore an important and immediate goal for the pharmaceutical industry is to identify all such genes in the human genome and describe their fine structure.

Processing and Integration of Peptide Masses, Peptide Signatures, ESTs and Public Domain Genomic Sequence Data to Form OGAP® Database Discrete genetic units (exons, transcripts and genes) were identified using the following sequential steps:

1. A "virtual transcriptome" is generated, containing the tryptic peptides which map to the human genome by combining the gene identifications available from Ensembl and various gene prediction programs. This also incorporates SNP data (from dbSNP) and all alternate splicing of gene identifications. Known contaminants were also added to the virtual transcriptome.
2. All tandem spectra in the OGeS Mass Spectrometry Database are interpreted in order to produce a peptide that can be mapped to one in the virtual transcriptome. A set of automated spectral interpretation algorithms were used to produce the peptide identifications.
3. The set of all mass-matched peptides in the OGeS Mass Spectrometry Database is generated by searching all peptides from transcripts hit by the tandem peptides using a tolerance based on the mass accuracy of the mass spectrometer, typically 20 ppm.

4. All tandem and mass-matched peptides are combined in the form of "protein clusters". This is done using a recursive process which groups sequences into clusters based on common peptide hits. Biological sequences are considered to belong to the same cluster if they share one or more tandem or mass-matched peptide.
5. After initial filtering to screen out incorrectly identified peptides, the resulting clusters are then mapped on the human genome.
6. The protein clusters are then aggregated into regions that define preliminary gene boundaries using their proximity and the co-observation of peptides within protein clusters. Proximity is defined as the peptide being within 80,000 nucleotides on the same strand of the same chromosome. Various elimination rules, based on cluster observation scoring and multiple mapping to the genome are used to refine the output. The resulting "confirmed genes" are those which best account for the peptides and masses observed by mass spectrometry in each cluster. Nominal co-ordinates for the gene are also an output of this stage.
7. The best set of transcripts for each confirmed gene are created from the protein clusters, peptides, ESTs, candidate exons and molecular weight of the original protein spot.
8. Each identified transcript was linked to the sample providing the observed peptides.
9. Use of an application for viewing and mining the data. The result of steps 1-8 was a database containing genes, each of which consisted of a number of exons and one or more transcripts. An application was written to display and search this integrated genome/proteome data. Any features (OMIM disease locus, InterPro etc.) that had been mapped to the same Golden Path co-ordinate system by Ensembl could be cross-referenced to these genes by coincidence of location and fine structure.

Results

The process was used to generate approximately 1 million peptide sequences to identify protein-coding genes and their exons resulted in the identification of protein sequences for 18083 genes across 67 different tissues and 57 diseases including 506 genes in bladder cancer, 4,713 genes in breast cancer, 1,371 genes in cervical cancer, 949 genes in colorectal cancer, 1,544 genes in glioblastoma, 1,782 genes in hepatocellular carcinoma, 2,424 genes in chronic lymphocytic leukaemia, 978 genes in lung cancer, 1,764 genes in melanoma, 1,033 genes in ovarian cancer, 2,961 genes in pancreatic cancer and 3,307 genes in prostate cancer, illustrated here by matriptase isolated and identified from breast cancer and colorectal cancer samples.

1.2 Results

These experiments identified matriptase, as further described herein. The full-length matriptase was detected in the plasma membrane of breast cancer and colorectal cancer samples and was not detected in the cytosol.

EXAMPLE 2

Identification of Membrane Proteins Expressed in Prostate Cancer Tissue Samples

Using the following Reference Protocol, membrane proteins extracted from prostate cancer tissue samples were analysed using Isotope-Coded Affinity Tags (ICAT).

2.1 Materials and Methods 2.1.1—Preparation of Membrane Fractions

The cells recovered from a prostate cancer were lysed and submitted to centrifugation at 1000 G. The supernatant was taken, and it was subsequently centrifuged at 3000 G. Once again, the supernatant was taken, and it was then centrifuged at 100 000 G.

The resulting pellets were dissolved by boiling in labeling buffer (50 mM Tris-HCl pH 8.3, 5 mM EDTA, 0.5% SDS), and the protein concentration was measured.

A Western blot was used to verify membrane protein markers.

2.1.2—Synthesis of ICAT Reagents

The ICAT reagents used were synthesized with the following isotopically different substrates: 4,7,10-trioxa-1,13-tridecanediamine (A) (Aldrich, Milwaukee, Wis.) and 2,2',3,3',11,11',12,12'-octadeutero-4,7,10-trioxa-1,13-tridecanediamine (B) (Gerber, S. A., Scott, C. R., Turecek, F. & Gelb, M. H. Analysis of rates of multiple enzymes in cell lysates by electrospray ionization mass spectrometry. *J. Am. Chem. Soc.* 121, 1102-1103 (1999)). Synthesis of N-(13-amino-4,7,10-trioxamidecanyl) biotinamide (C) was as follows. To biotin-pentafluorophenylester (Pierce, Rockford, Ill.) in dry dimethylformamide containing excess N,N-diisopropylethylamine (Aldrich) were added five equivalents of (A) with stirring at room temperature for 3 h. Solvent was removed under reduced pressure and (C) was purified to homogeneity by reverse-phase HPLC. The heavy analog was prepared as per (C), but with five equivalents of (B). Synthesis of N-(13-iodoacetamido-4,7,10-trioxamidecanyl) biotinamide (D) was as follows. To (C) (or heavy analog) in dry dimethylformamide containing excess N,N-diisopropylethylamine was added two equivalents iodoacetic anhydride (Aldrich) with stirring at room temperature for 3 h. Solvent was removed under reduced pressure, and (D) was purified to homogeneity by reverse-phase HPLC and characterized by MS.

2.1.3—ICAT Analysis 100 ug of total protein was used. Disulfide bonds in the denatured protein mixtures were reduced (50 mM Tris buffer pH 8.5, 6 M guanidine HCl, 5 mM tributyl phosphine) for 1 h at 37° C. Cysteinyl groups in each mixture were independently biotinylated with a fivefold molar excess of the appropriate ICAT reagent. Excess ICAT reagent was removed from the combined samples by gel filtration (Bio-Rad, Richmond, Calif.) in Tris buffer (50 mM, pH 8.5) with 0.1% SDS, and the protein fraction was digested with trypsin (Promega, Madison, Wis.) overnight at 37° C. The peptide solution was then passed over a prepared monomeric avidin column (Pierce). The column was washed with water, and biotinylated peptides were eluted with 0.3% formic acid (1 ml fractions). The volume of sample eluted (in 0.3% formic acid) was reduced from 1,000 to 50 ul. Peptide recovery across the entire procedure was estimated at approximately 70%.

An LCQ ion trap mass spectrometer (Finnigan MAT, San Jose, Calif.) was used with an in-house fabricated microelectrospray source (see e.g. Figeys, D. et al. Electrophoresis combined with novel mass spectrometry techniques: powerful tools for the analysis of proteins and proteomes. *Electrophoresis* 19, 1811-1818 (1998)) and an HP1100 solvent delivery system (Hewlett Packard, Palo Alto, Calif.). A 60 min binary gradient with 5-80% solvent B (acetonitrile and 0.005% heptafluorobutyric acid (HFBA)). Solvent A consisted of 0.4% acetic acid and 0.005% HFBA. A flow rate of 0.5 ul/min was used with a 100 um×12 cm fused silica capillary column in-house packed with Monitor spherical silica (Column Engineering, Ontario, Calif.). Functional chromatography has been achieved with this setup with peptide loads as high as 500 µmol. in $H_2O$. One microliter of the peptide mixture was pressure loaded onto the column. Eluting peptides were analyzed by uLC-MS and uLC-MS/MS techniques as described elsewhere (see e.g. Gygi, S. P., Rochon, Y., Franza, B. R. & Aebersold, R, Correlation between protein and mRNA abundance in yeast, *Mol. Cell. Biol.* 19, 1720-1730 (1999) and Gygi, S. P., Han, D. K. M., Gingras, A. C., Sonenberg, N. & Aebersold, R, Protein analysis by mass spectrometry and sequence database searching: tools for cancer research in the post-genomic era, *Electrophoresis* 20, 310-319 (1999)). The intensities of eluting peptide pairs were measured in the scanning mass spectrometer. There is a slight difference in the elution times of differentially tagged peptide pairs, with the heavy analog eluting 1-2 s before the light analog. For this reason, the entire peak area of each eluting peptide was reconstructed and used in the ratio calculation. To determine the amino acid sequence, the mass spectrometer operated in a data-dependent MS/MS mode (a full-scan mass spectrum is followed by a tandem mass spectrum), where the precursor ion is selected "on the fly" from the previous scan. An m/z ratio for an ion that had been selected for fragmentation was placed in a list and dynamically excluded for 1 min from further fragmentation. For partial amino acid sequencing and identification of OGTA284, uninterpreted tandem mass spectra of tryptic peptides were searched using the SEQUEST search program (Eng, J., McCormack, A. L. & Yates, J. R. An approach to correlate tandem mass spectral data of peptides with amino acid sequences in a protein database. *J. Am. Soc. Mass Spectrom.* 5, 976-989 (1994)), which searched tandem mass spectra against the OWL nonredundant sequence database (Bleasby, A. J., Akrigg, D. & Attwood, T. K. OWL—a non-redundant composite protein sequence database. *Nucleic Acids Res.* 22, 3574-3577 (1994)).

2.1.4—Discrimination of Prostate Cancer Associated Proteins

The process described in Example 1 section 1.1.6 was employed to discriminate the prostate cancer associated proteins in the experimental samples.

2.2 Results

These experiments identified matriptase, as further described herein. The full-length matriptase was detected in the membrane of prostate cancer samples and was not detected in the cytosol.

EXAMPLE 3

Generation of Antibodies to the Matriptase Stem

Using the following Reference Protocol, a matriptase stem Fc-fusion protein was generated and used for immunisation and generation of antibodies to the matriptase stem.

3.1 Materials and Methods 3.1.1—Generation of Matriptase Stem Fc-Fusion Protein

The full-length matriptase (OGTA004) cDNA was purchased from Open Biosystems, IMAGE ID# 5213189, and was used as a template for amplification. Primers were designed to amplify the stem region spanning amino acids 86-201 and to allow subcloning, in frame, with an N-terminal osteonectin signal sequence, and the C-terminal Factor Xa cleavage site and human FcG1. The insert was subcloned in an Invitrogen pcDNA 3.1 based mammalian expression vector with the hygromycin selectable marker. CHO-S cells were transfected using Invitrogen's DMRIE-C reagent and stable cells were selected under 500 ug/mL of hygromycin B. Expression of the fusion protein was confirmed via Western blot with anti-human Fc antibodies and anti-matriptase stem antibodies. The fusion protein is shown in FIG. 4.

3.1.2—Hybridoma Generation

The Sp2/0 myeloma cell line (ATCC CRL 1581) was used for the fusions. The original ATCC vial was thawed and expanded in culture. A seed stock of frozen vials was prepared from this expansion. Cells were maintained in culture for 1 month, passed twice a week. Supernatant from P388D1 (ATCC, TIB-63 FL) cells was used as conditioned media for the hybridomas. Briefly, cells were grown and expanded to 200 mL. Stationary cultures were grown for ~7 days. The exhausted supernatant was spun down and filtered through a 0.2 µm sterile filter. This cell line was passed for 1 month and then a new vial thawed and cultered.

3.1.3—Immunisation using OGTA004 Stem Fusion Protein

The antibody was generated from a fusion of spleen/lymph nodes of a mouse (Hco7 (J/K)/Balb/c) immunized with OGTA004 stem—hFcG1 protein at 20 ug dose in Ribi adjuvant by footpad/ip/sc at 2-4 day intervals for a total of 5 immunisations.

3.2 Results

Antibody Medarex Clone 1432.896.13B4 was generated from the above protocol.

EXAMPLE 4

Immunohistochemistry Using Antibody to the Matriptase Stem

Using the following Reference Protocol, immunohistochemistry was performed on FFPE tumour and normal tissues using a rabbit polyclonal antibody to the extra-cellular stem region of matriptase (AbCAM, UK, ab28267).

4.1 Materials and Methods 4.1.1—Determination of specificity of antibody

The specificity of the anti-matriptase stem antibody (Abcam # 28267) was determined by ELISA. Plates were coated with either 2 mg/ml stem-fusion protein (Medarex) or matriptase (matriptase) catalytic domain (Biosite). Anti-matriptase antibodies were tested at 10 mg/ml and binding was detected with horseradish peroxidase (HRP)-conjugated Goat anti-Rabbit antibodies.

Results show that the anti-matriptase stem antibody, Ab 28267, is highly specific to the stem-fusion protein and does not bind to the matriptase catalytic domain.

Protocol for Staining FFPE Tissue Slides 4.1.2—Deparaffinization and Rehydration Slides were placed in xylene bath and incubated for 5 minutes. The bath was changed and the process was repeated once. Excess liquid was tapped off and the slides were placed in absolute ethanol for 5 minutes. Excess liquid was tapped off and the slides were placed in 90% ethanol for 5 minutes. Excess liquid was tapped off and the slides were placed in 80% ethanol for 5 minutes. Excess liquid was tapped off and the slides were placed in 70% ethanol for 5 minutes. Excess liquid was tapped off and the slides were placed in distilled or deionized water for a minimum of 30 seconds.

If necessary, rehydrated tissues may be kept in buffer solution at 2-8° C. for up to 18 hours prior to use. Allow tissues to come to room temperature before staining.

4.1.3—Antigen Retrieval

Slides were rinsed in deionized water. The slides were then placed in a gray Tissue Tek slide holder with the empty slots filled with blank slides. The holder was placed in a white Tissue Tek bath containing 250 ml of working strength Antigen Retrieval Solution. The lid was placed loosely on the bath and centered inside a microwave oven on a paper towel to adsorb any liquid run-over. The oven was turned on high power and the solution was closely watched until it came to a rapid boil, and then immediately the oven was turned off (about 2 minutes.) The oven power was set to approximately 10% level and heated for 10-15 minutes. The bath/slides were removed from the oven and allowed to cool in the bath for 20-30 minutes to reach room temperature. They were then rinsed with several changes of deionized water. The slides were placed in PBS.

4.1.4—Staining

Peroxidase blocking: Excess buffer was tapped off. Then, using a Kimwipe, around the specimen was carefully wiped to remove any remaining liquid and to keep reagents within prescribed area. The region was marked with PAP pen. Enough Peroxidase Blocking Reagent was applied from Bottle 1 to cover specimen. It was incubated for 5 minutes. It was then gently rinsed with distilled water or PBS from a wash bottle and placed in fresh PBS bath. Tissue was blocked with 10% serum (from species of secondary antibody) for 20-30 minutes. Blocking buffer was dumped off and the primary stain was applied.

Primary or negative control reagent: Excess buffer was tapped off. Enough primary antibody or negative control was applied to cover specimen. It was incubated for 30 minutes. The antibody solution was removed and saved if necessary. It was rinsed gently with PBS from a wash bottle and placed in fresh PBS bath for 5 minutes. This was repeated once. Note: If the staining procedure must be interrupted, slides may be kept in PBS following incubation of the primary antibody for up to one hour at room temperature without affecting the staining Peroxidase Labeled Polymer: Excess buffer was tapped off. Enough drops from Bottle 3 (Labeled Polymer) were applied to cover specimen. It was incubated for 30 minutes. Slides were rinsed as above.

Substrate-Chromogen: Excess buffer was tapped off and enough of the ready-to-use substrate-chromagen solution was applied to cover specimen. It was incubated for 5-10 minutes and then rinsed gently with distilled water from a wash bottle. The substrate-chromagen waste was collected in a hazardous materials container for proper disposal.

Hematoxylin Counter Stain: The slides were immersed in a bath of aqueous 0.1% hematoxylin and incubated for 2-5 minutes, depending on strength. Rinsed gently with tap water in a bath.

Mounting: Excess water was tapped off and 1-2 drops of mounting medium were applied and the slip covered.

4.2 Results

Immunohistochemistry using a rabbit polyclonal antibody to the extra-cellular stem region of matriptase (AbCAM, UK, ab28267) demonstrated homogeneous staining of tumour cells in esophageal, uterine, gastric and breast cancer samples consistent with the hypothesis that antibodies targeting the stem region of matriptase can be used to target cancer cells of epithelial origin in a therapeutic setting. The specificity for this antibody is demonstrated by IHC on multiple other cancer and normal tissues. No staining was observed in normal esophagus, normal liver, normal breast, and normal ovary tissues. Sporadic staining was seen in epithelial cells in normal stomach and normal colon samples.

EXAMPLE 5

Assay to Detect the Soluble Catalytic Domain of Matriptase Using Sandwich ELISA

Using the following Reference Protocol, sandwich ELISAs were performed using antibodies to the catalytic domain of matriptase.

5.1 Materials and Methods

Antibodies to the catalytic domain of matriptase (as defined by SEQ ID No: 14, see FIG. 3) for the sandwich ELISAs were developed at Biosite. Biotinylated antibody (primary antibody) was diluted into assay buffer (10 mM Tris, 150 mM NaCl, 1% BSA) to 2 ug/ml and added to 384 well neutravidin coated plate (Pierce Chemical Company, Rockford Ill.) and allowed to incubate at room temperature for 1 hour. Wells were then washed with wash buffer (20 mM Borate, 150 mM NaCl, 0.2% Tween 20). Samples and standards were added and allowed to incubate at room temperature for 1 hour. Wells again were washed. An antibody conjugated to fluorescein (secondary antibody) was diluted into assay buffer to 2 ug/ml and was then added to the plate and allowed to incubate at room temperature for 1 hour. Wells again were washed. Anti-fluorescein antibody conjugated to alkaline phosphatase, diluted $\frac{1}{2338}$ into assay buffer, was added and allowed to incubate at room temperature for 1 hour. Final wash was then performed. Finally substrate (Promega Attophos Product#S1011, Promega Corporation, Madison, Wis.) was added and the plate was read immediately. All additions were 10 ul/well. The plate was washed 3 times between each addition and final wash was 9 times prior to the addition of substrate. Standards were prepared by spiking specific antigen into a normal serum patient pool. Reading was performed using a Tecan Spectrafluor plus (Tecan Inc, Mannedorf, Switzerland) in kinetic mode for 6 read cycles with excitation filter of 430 nm and an emission filter 570 nm emission. Slope of RFU/seconds was determined.

Final Box and ROC results were analyzed using Analyse-it General+Clinical Laboratory 1.73 (Analyse-it Software Ltd., Leeds England).

5.2 Results

These experiments detected the soluble catalytic domain of matriptase in breast cancer, colorectal cancer and prostate cancer samples at higher concentrations than found in normal samples. The catalytic domain is released following cleavage of matriptase, so these experiments demonstrate that matriptase is being cleaved in breast cancer, colorectal cancer and prostate cancer, and indicate the availability of the matriptase stem as a therapeutic target for these cancers.

FIG. 5 shows Box plot data for the catalytic domain of matriptase in prostate cancer samples. The vertical axis on this graph is concentration of the catalytic domain of matriptase in ng/ml. These data show higher concentration of the catalytic domain of matriptase in prostate cancer samples compared to normal samples, with a significant p value, thereby indicating the availability of the matriptase stem as a therapeutic target in prostate cancer.

EXAMPLE 6

Multiplex Assay to Detect the Soluble Catalytic Domain of Matriptase Using Luminex Technology Using the following Reference Protocol, multiplex assays using the Luminex technology were performed using antibodies to the catalytic domain of matriptase.

6.1 Materials and Methods

Each primary antibody to the catalytic domain of matriptase (as defined by SEQ ID No: 14, see FIG. 3) was conjugated to a unique Luminex magnetic microsphere (Mug beads, Luminex Corporation, Austin, Tex.). Mag bead cocktail (50 ul) was added to a 96 black well round bottom Costar plate (Corning Incorporated, Corning N.Y.). Using a 96 well magnetic ring stand, the Mag beads were pulled down for 1 minute and washed with wash/assay buffer (PBS with 1% BSA and 0.02% Tween 20). 50 ul of sample or standard was added along with an additional 50 ul of wash/assay buffer and allowed to incubate on a shaker for 1 hour at room temperature. Plate was placed on magnetic ring stand and allowed to sit for 1 minute. Mag beads were then washed again. Biotin labeled antibody was then added at 50 ul per well with an additional 50 ul of wash/assay buffer and allowed to incubate on a shaker for 1 hour at room temperature. The plate again was placed on a magnetic stand and the Mag beads were washed. Streptavidin-RPE (Prozyme, San Leandro, Calif., Phycolin, Code#PJ31S) was diluted to 1 ug/ml in wash/assay buffer and 50 ul was added to each well along with an additional 50 ul of wash/assay buffer and allowed to incubate on a shaker for 1 hour at room temperature. Final wash was performed and the beads were re-suspended with 100 ul of wash/assay buffer and each well was then read in a Luminex 200 reader using Xponent software 3.0. All reagent dilutions were made in wash/assay buffer. Biotin-antibody varied for each assay to optimal concentration. Initial Mag bead amounts added were approximately 50,000 for each assay. Magnetic beads were allowed 1 minute pull down time prior to each wash. Each wash step was 3 times washed with 100 ul of wash/assay buffer. Assay standard curves were made in a normal donor patient serum pool. Luminex reader and Mag beads were used and prepared according to manufacturer guidelines. Standard curves were calculated using a 5 parameter log-logistic fit and each sample concentration was determined from this curve fit.

Final Box and ROC results were analyzed using Analyse-it General+Clinical Laboratory 1.73 (Analyse-it Software Ltd., Leeds England).

6.2 Results

Figure 6A:
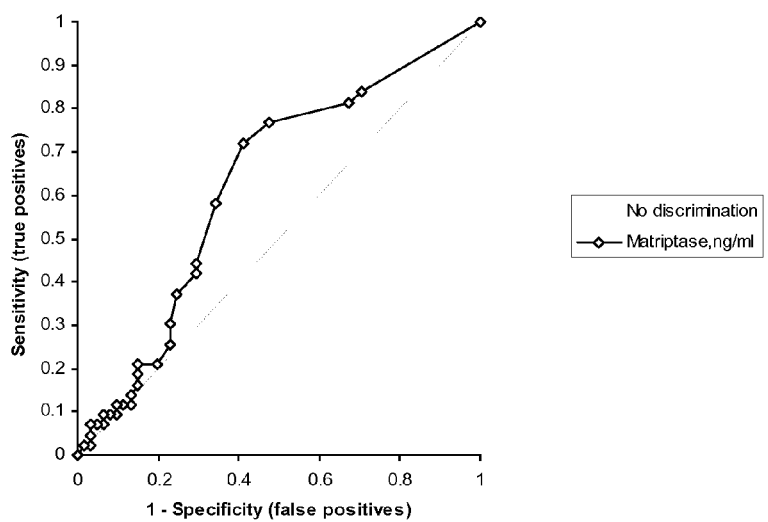
FIGS. 6a-6b show ROC curve data for the catalytic domain of the protein of the invention in breast cancer (FIG. 6(a)) and colorectal cancer (FIG. 6(b)) samples.
Figure 6B:
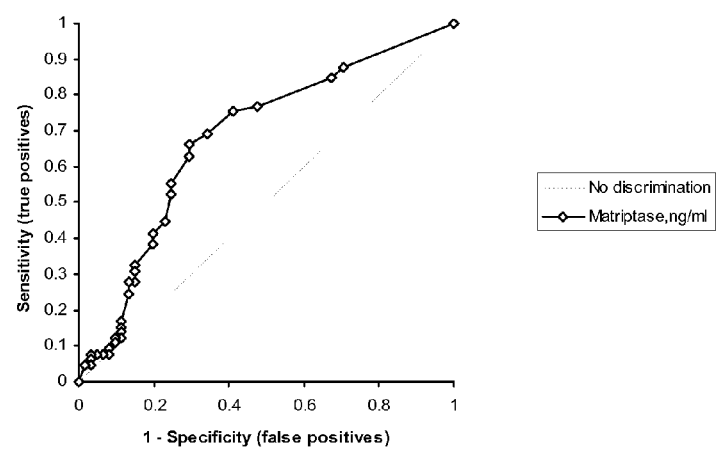

Experiments using 61 normal samples, 43 breast cancer samples, 65 colorectal cancer samples and 14 prostate cancer samples resulted in further evidence that the soluble catalytic domain of matriptase can be detected in breast cancer, colorectal cancer and prostate cancer samples and also that the concentration of the catalytic domain is higher in breast cancer, colorectal cancer and prostate cancer than in normal samples. This demonstrates that matriptase is being cleaved in breast cancer, colorectal cancer and prostate cancer, indicating the availability of the stem as a therapeutic target FIGS. 6a and 6b show ROC curve data for matriptase for breast cancer and colorectal cancer respectively. The ROC curves plot sensitivity (true positives) against 1-specificity (false positives). An area under the ROC curve of greater than 0.5 indicates good discrimination between disease and normal. This is the case in the data shown in FIGS. 6a and 6b, which, along with the low p values, indicate that the concentration of the catalytic domain is significantly higher in breast cancer and colorectal cancer than in normal samples.

EXAMPLE 7

Screening Antigen Specific Antibody Using Enzyme-Linked Immunosorbent Assay (ELISA)

Using the following Reference Protocol, the specificity of the rabbit polyclonal antibody to the extra-cellular stem region of matriptase (AbCAM, UK, ab28267) was determined by Enzyme-Linked Immunosorbent Assay (ELISA).

7.1 Materials and Methods

The plate was coated overnight with matriptase stem peptide (or in-house matriptase stem-hFc or irrelevant HIgG or hFc protein) 1-2 µg/mL in 1×PBS, 50 µL/well. It was stored in the refrigerator. The plate was emptied and blocked in 1×PBST+5% chicken serum for 30 min-1 hour at room temperature (200 µL/well). The plate was emptied and washed manually with a wash bottle (3×) or plate washer (3×) using 1×PBST. If a wash bottle was used, plates were drained on paper towels.

50 µL/well of blocking buffer was added into the plate and then 50 µL/well of hybridoma supernatant was added. It was incubated at room temperature for 1 hour. A positive control was used when available. The plate was emptied and washed manually with a wash bottle (3×) or plate washer (3×) using 1×PBST. If a wash bottle was used, plates were drained on paper towels.

The secondary, HRP anti-human-IgG Fc (1:3000) or HRP anti-human κ (1:2000) was diluted in 1×PBST+5% chicken serum. 100 µL/well was added and it was incubated for 1 hour at room temperature. The plate was emptied and washed manually with a wash bottle (3×) or plate washer (3×) using 1×PBST. If a wash bottle was used, plates were drained on paper towels.

The plate was developed using 10 mL ABTS substrate. It was incubated for 15-30 minutes at room temperature. The plate was read with Molecular Devices software (415-490 nM).

Reagents and Equipment:

Phosphate buffered saline (PBS), DPBS without Ca and Mg (Hyclone SH30013.03 or Sigma P 3813).

PBS-T (wash buffer), PBS containing 0.05% Tween 20 (Sigma P-1379).

PBS-T plus 1% BSA (Sigma A 9647) or 5% chicken serum. This serves as the blocking buffer and sample buffer.

ELISA plates (Nunc, Immuno-plate F96 Maxisorp 442-404 or Falcon, 353912 flex plates or Costar EIA/RIA Plates, 96-well flat bottom, # 9018).

matriptase stem peptide, in-house matriptase stem-hFc, irrelevant HIgG and hFc protein HRP anti-human g-chain specific antibody (Jackson, 109-036-098), HRP anti-human κ (Bethyl, A80-115P).

ABTS substrate (Moss Inc, product: ABTS-1000).

ELISA plate reader with 405 nm filter.

Automated ELISA plate washer.

7.2 Results

Figure 7A:
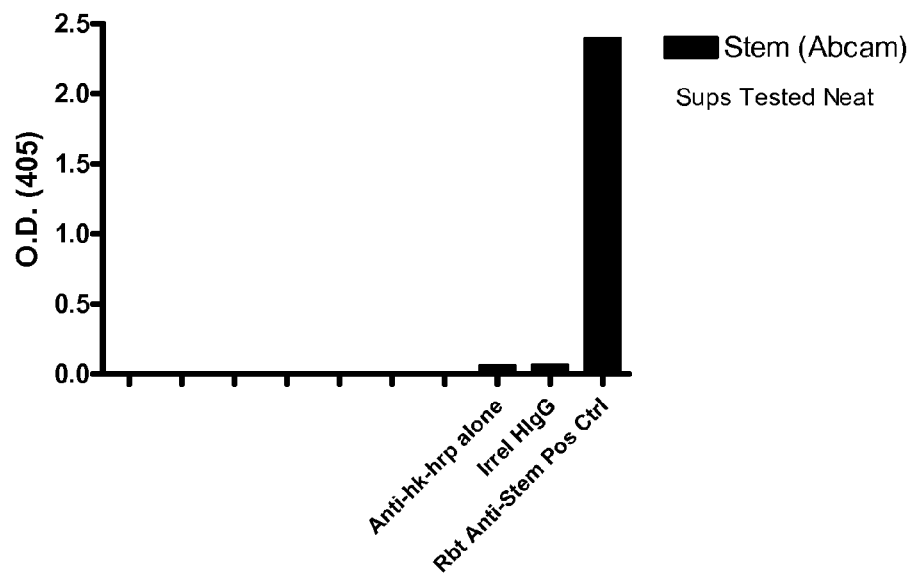
FIGS. 7a-7b show graphs of the Enzyme-Linked Immunosorbent Assay (ELISA) analysis of a rabbit polyclonal antibody to the extra-cellular stem region of matriptase (Ab-CAM, UK, ab28267).
Figure 7B:
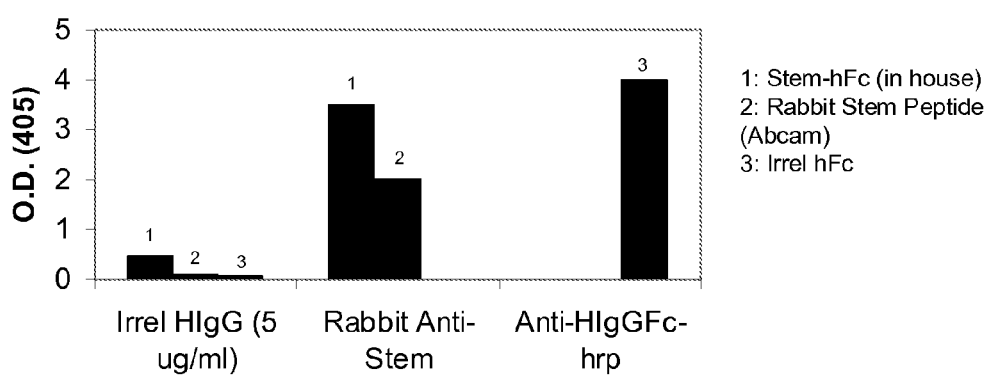

FIGS. 7(a) and 7(b) show graphs of the ELISA analysis with the optical density at 405 nm on the vertical axis and the antibodies and controls on the horizontal axis. FIG. 7(a) shows results for anti-hk-hrp alone, irrelevant HIgG and the rabbit polyclonal antibody to the matriptase stem (AbCAM, UK, ab28267) which demonstrate that the rabbit polyclonal antibody is highly specific to the stem of matriptase. FIG. 7(b) shows results for irrelevant HIgG (5 µg/ml), the rabbit polyclonal antibody to the matriptase stem (AbCAM, UK, ab28267) and anti-HIgGFc-hrp for the in-house stem-hFc protein, the rabbit stem peptide and irrelevant hFc. This graph shows that the rabbit polyclonal antibody is highly specific to the matriptase stem (in-house stem-hFc protein and the rabbit stem peptide).

EXAMPLE 8

Screening of Antibody Using Fluorescence-Activated Cell Sorting (FACS)

Using the following Reference Protocol, the rabbit polyclonal antibody to the extra-cellular stem region of matriptase (AbCAM, UK, ab28267) was screened on HT-29 colon cancer cells using fluorescence-activated cell sorting (FACS).

8.1 Materials and Methods

The cells were prepared by counting the HT-29 cells and calculating the viability for each cell line. Enough cells for a $0.25 \times 10^5$/sample were transferred to a 50 ml tube and washed twice with PBS.

The cells were re-suspended in cold FACS buffer (2% FBS in PBS with 0.02% azide) at $2.5 \times 10^5$ cells/ml. 100 µL/well was added to a U-bottom 96-well plate (Falcon Non-Tissue Culture Treated #35-1177) and centrifuged at 2500 RPM for 1 minute. The buffer was discarded in one quick motion and the plate was gently patted on paper towels to remove excess buffer.

100 µL of supernatant samples and controls were added to the wells and the pellets were resuspended. It was incubated for 30-40 min on ice. It was then washed once with 200 µL/well of the FACS buffer and centrifuged at 2500 RPM at 4° C. for 1 minute. The buffer was discarded.

50 µL/well of secondary FITC-labeled goat anti human IgG Fc specific (Jackson, # 109-095-098) was added at 1:100 dilution. It was incubated for 20-30 min at 4° C. in the dark and then washed twice with 200 µL/well of the FACS buffer and centrifuged at 2500 RPM at 4° C. for 1 minute.

The samples were resuspended in 80 µL/well FACS buffer containing propidium iodide (Roche, Cat. 1 348 639) diluted 1:100. The 96-well plate was directly read on FACS Caliber. The data were analysed using CellQuest software.

FACS Reagents:
FACS buffer: Phosphate buffered saline (PBS) plus 2% FBS (Hyclone, # SH30071.03) and 0.02% of NaN3 (Sigma # S-8032). This served as the blocking buffer as well as the wash buffer.
ELISA plates (Becton Dickinson, Falcon, U-bottom 96 well-plate, # 351177).
FACS tubes (Becton Dickinson, Falcon, # 352052).
FITC labeled Anti-human γ-chain specific antibody (Jackson, #109-095-098).
Propidium Iodide (Roche # 1348639)
FACScalibur (Becton Dickinson)
Eppendorf centrifuge (Eppendorf # 581012)

8.2 Results

Figure 8:
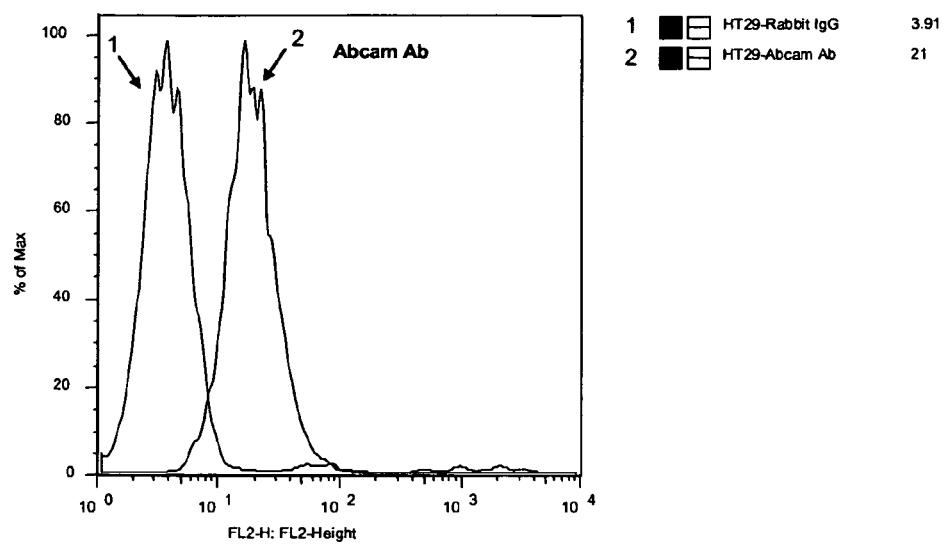
FIG. 8 shows a graph of the fluorescence-activated cell sorting (FACS) analysis of a rabbit polyclonal antibody to the extra-cellular stem region of matriptase (AbCAM, UK, ab28267) on HT-29 colon cancer cells.

FIG. 8 shows a graph of the FACS analysis on HT-29 colon cancer cells with % of max on the vertical axis and fluorescent channel 2 height on the horizontal axis. This graph shows that the rabbit polyclonal antibody to the extra-cellular stem region of matriptase (AbCAM, UK, ab28267) binds well to the HT-29 colon cancer cells.

EXAMPLE 9

Detection of Matriptase Stem Protein Using Western Blot

Using the following Reference Protocol, the rabbit polyclonal antibody to the extra-cellular stem region of matriptase (AbCAM, UK, ab28267) was used to detect matriptase in CHO-S cells expressing recombinant matriptase stem-FcG1 fusion protein using Western Blotting.

9.1 Materials and Methods

Cells growing in monolayer were lysed in situ with 2× Laemmli sample buffer containing 4% SDS, 20% glycerol, 10% 2-mercaptoethanol, 0.004% bromophenol blue, 0.125 M Tris-HCl, pH 6.8, proteinase inhibitors, and immediately snap frozen. After boiling at 95 C. for 5 min samples were cooled down, treated with benzonase (>1000 units per 1 ml of sample) for 30 min, and subjected to a series of sonication in an ultrasonic waterbath (5-10 times, 10-15 min each time) to sheer genomic DNA.

Proteins from 20-30 µl of lysate per lane were separated by mini-gel electrophoresis on Novex and NuPAGE/Novex pre-cast mini-gels (Invitrogen, UK). Gels were blotted onto nitro-cellulose membrane with iBlot Dry Blotting System (Invitrogen, UK). The amount of lysates loaded was estimated by presence of GAPDH (anti-GAPDH antibody: cat. n. CB 1001, Calbiochem; at 1:10000) as a loading marker.

Membrane was incubated with animal-free blocker (Vector) and probed with rabbit polyclonal antibody to the extra-cellular stem region of matriptase (AbCAM, UK, ab28267) in animal-free blocker at 1:500 dilution, at 4 C, for 14-18 h, rotating. The secondary antibody was anti-mouse DyLight 488 conjugate (Pierce).

9.2 Results

Figure 9:
FIG. 9 shows the results of the Western Blot analysis to detect matriptase in CHO-S cells expressing recombinant matriptase stem-Fc protein using a rabbit polyclonal antibody to the extra-cellular stem region of matriptase (AbCAM, UK, ab28267).

FIG. 9 shows the results of two Western Blots on CHO-S cells expressing recombinant matriptase stem-FcG1 fusion protein probed with the rabbit polyclonal antibody to the extra-cellular stem region of matriptase (AbCAM, UK, ab28267). These results show that there is a signal at a size corresponding to the predicted molecular weight of the matriptase stem-FcG1 fusion protein.

All references referred to in this application, including patent and patent applications, are incorporated herein by reference to the fullest extent possible.

Throughout the specification and the claims which follow the term, "matriptase" has been used to replace the phrase "the protein of the invention" and to replace the Applicant's internal reference OGTA004 as recited in U.S. provisional application U.S. 60/963,837, from which this application claims the benefit of priority. All of these terms are to be understood as referring to the matriptase polypeptide, the "stem" of which is the portion that remains on the cell surface following activation site autocleavage.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

Embodiments of the invention are described herein, which comprise certain elements. The invention also extends to separate embodiments consisting of or consisting essentially of the same elements, and vice versa.

The application of which this description and claims form part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A method for treating cancer, which comprises administering to a subject in need thereof a therapeutically effective amount of an affinity reagent selected from the group consisting of a monoclonal antibody and a monoclonal antibody fragment, which specifically binds to the matriptase stem located on the cell surface.

2. A method for treating cancer, which comprises administering to a subject in need thereof a therapeutically effective amount of an affinity reagent selected from the group consisting of a monoclonal antibody and a monoclonal antibody fragment, which specifically binds to the matriptase stem located on the cell surface, wherein the monoclonal antibody or monoclonal antibody fragment does not bind to the matriptase catalytic domain.

3. A method according to claim 1, wherein the cancer is selected from the group consisting of breast cancer, colorectal cancer, esophageal cancer, gastric cancer, prostate cancer and uterine cancer.

4. The method according to claim 1, wherein the matriptase stem has the amino acid sequence defined in any one of SEQ ID NOs: 10, 11, 12 and 13, or a sequence having 80% homology to any one of SEQ ID NOs: 10, 11, 12 and 13.

5. The method according to claim 4, wherein the matriptase stem has the amino acid sequence defined in any one of SEQ ID NOs: 10, 11, 12 and 13, or a sequence having 90% homology to any one of SEQ ID NOs: 10, 11, 12 and 13.

6. The method according to claim 5, wherein the matriptase stem has the amino acid sequence defined in any one of SEQ ID NOs: 10, 11, 12 and 13, or a sequence having 95% homology to any one of SEQ ID NOs: 10, 11, 12 and 13.

7. The method according to claim 6, wherein the matriptase stem has the amino acid sequence defined in any one of SEQ ID NOs: 10, 11, 12 and 13.

8. The method according to claim 1, wherein the affinity reagent contains or is conjugated to a therapeutic moiety.

9. The method according to claim 8, wherein the therapeutic moiety is a cytotoxic moiety or a radioactive moiety.

10. The method according to claim 9, wherein the therapeutic moiety is a cytotoxic moiety.

11. The method according to claim 1, wherein the affinity reagent is a monoclonal antibody.

12. The method according to claim 1, wherein the monoclonal antibody is a full-length antibody of an IgG1, IgG2, IgG3, or IgG4 isotype.

13. The method according to claim 1, wherein the monoclonal antibody is selected from the group consisting of a humanised antibody, a single chain antibody, an immunoconjugate, a defucosylated antibody and a bispecific antibody.

14. The method according to claim 1, wherein the monoclonal antibody fragment is selected from the group consisting of a UniBody, a domain antibody and a Nanobody.

15. The method according to claim 11, wherein the monoclonal antibody has cytotoxicity against matriptase stem antigen expressing cells in the presence of a human complement.

16. The method according to claim 11, wherein the monoclonal antibody has cytotoxicity against matriptase stem antigen expressing cells in the presence of human immune effector cells.

17. A method according to claim 2, wherein the cancer is selected from the group consisting of breast cancer, colorectal cancer, esophageal cancer, gastric cancer, prostate cancer and uterine cancer.

18. The method according to claim 2, wherein the matriptase stem has the amino acid sequence defined in any one of SEQ ID NOs: 10, 11, 12 and 13, or a sequence having 80% homology to any one of SEQ ID NOs: 10, 11, 12 and 13.

19. The method according to claim 18, wherein the matriptase stem has the amino acid sequence defined in any one of SEQ ID NOs: 10, 11, 12 and 13, or a sequence having 90% homology to any one of SEQ ID NOs: 10, 11, 12 and 13.

20. The method according to claim 19, wherein the matriptase stem has the amino acid sequence defined in any one of SEQ ID NOs: 10, 11, 12 and 13, or a sequence having 95% homology to any one of SEQ ID NOs: 10, 11, 12 and 13.

21. The method according to claim 20, wherein the matriptase stem has the amino acid sequence defined in any one of SEQ ID NOs: 10, 11, 12 and 13.

22. The method according to claim 2, wherein the affinity reagent contains or is conjugated to a therapeutic moiety.

23. The method according to claim 22, wherein the therapeutic moiety is a cytotoxic moiety or a radioactive moiety.

24. The method according to claim 23, wherein the therapeutic moiety is a cytotoxic moiety.

25. The method according to claim 2, wherein the affinity reagent is a monoclonal antibody.

26. The method according to claim 2, wherein the monoclonal antibody is a full-length antibody of an IgG1, IgG2, IgG3, or IgG4 isotype.

27. The method according to claim 2, wherein the monoclonal antibody is selected from the group consisting of a humanised antibody, a single chain antibody, an immunoconjugate, a defucosylated antibody and a bispecific antibody.

28. The method according to claim 2, wherein the monoclonal antibody fragment is selected from the group consisting of a UniBody, a domain antibody and a Nanobody.

29. The method according to claim 25, wherein the monoclonal antibody has cytotoxicity against matriptase stem antigen expressing cells in the presence of human complement.

30. The method according to claim 25, wherein the monoclonal antibody has cytotoxicity against matriptase stem antigen expressing cells in the presence of human immune effector cells.

* * * * *

SEQUENCE LISTING

<160> NUMBER OF SEQ ID NOS: 15

<210> SEQ ID NO 1

```
<211> LENGTH: 855
<212> TYPE: PRT
<213> ORGANISM: Homo sapiens

<400> SEQUENCE: 1

Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
                35                  40                  45

Lys His Gly Pro Gly Arg Trp Val Val Leu Ala Ala Val Leu Ile Gly
    50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
            100                 105                 110

Phe Val Ser Leu Ala Ser Lys Val Lys Asp Ala Leu Lys Leu Leu Tyr
        115                 120                 125

Ser Gly Val Pro Phe Leu Gly Pro Tyr His Lys Glu Ser Ala Val Thr
130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
            180                 185                 190

Val Thr Ser Val Val Ala Phe Pro Thr Asp Ser Lys Thr Val Gln Arg
        195                 200                 205

Thr Gln Asp Asn Ser Cys Ser Phe Gly Leu His Ala Arg Gly Val Glu
210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
            260                 265                 270

Ser Asp Leu Val Thr Val Tyr Asn Thr Leu Ser Pro Met Glu Pro His
        275                 280                 285

Ala Leu Val Gln Leu Cys Gly Thr Tyr Pro Pro Ser Tyr Asn Leu Thr
290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
            340                 345                 350

Ser Pro Tyr Tyr Pro Gly His Tyr Pro Pro Asn Ile Asp Cys Thr Trp
        355                 360                 365

Asn Ile Glu Val Pro Asn Asn Gln His Val Lys Val Arg Phe Lys Phe
370                 375                 380

Phe Tyr Leu Leu Glu Pro Gly Val Pro Ala Gly Thr Cys Pro Lys Asp
385                 390                 395                 400
```

```
Tyr Val Glu Ile Asn Gly Glu Lys Tyr Cys Gly Arg Ser Gln Phe
                405                 410                 415

Val Val Thr Ser Asn Ser Asn Lys Ile Thr Val Arg Phe His Ser Asp
            420                 425                 430

Gln Ser Tyr Thr Asp Thr Gly Phe Leu Ala Glu Tyr Leu Ser Tyr Asp
            435                 440                 445

Ser Ser Asp Pro Cys Pro Gly Gln Phe Thr Cys Arg Thr Gly Arg Cys
            450                 455                 460

Ile Arg Lys Glu Leu Arg Cys Asp Gly Trp Ala Asp Cys Thr Asp His
465                 470                 475                 480

Ser Asp Glu Leu Asn Cys Ser Cys Asp Ala Gly His Gln Phe Thr Cys
            485                 490                 495

Lys Asn Lys Phe Cys Lys Pro Leu Phe Trp Val Cys Asp Ser Val Asn
            500                 505                 510

Asp Cys Gly Asp Asn Ser Asp Glu Gln Gly Cys Ser Cys Pro Ala Gln
            515                 520                 525

Thr Phe Arg Cys Ser Asn Gly Lys Cys Leu Ser Lys Ser Gln Gln Cys
            530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
                565                 570                 575

Gly Leu Cys Leu Ser Lys Gly Asn Pro Glu Cys Asp Gly Lys Glu Asp
            580                 585                 590

Cys Ser Asp Gly Ser Asp Glu Lys Asp Cys Asp Cys Gly Leu Arg Ser
            595                 600                 605

Phe Thr Arg Gln Ala Arg Val Val Gly Gly Thr Asp Ala Asp Glu Gly
            610                 615                 620

Glu Trp Pro Trp Gln Val Ser Leu His Ala Leu Gly Gln Gly His Ile
625                 630                 635                 640

Cys Gly Ala Ser Leu Ile Ser Pro Asn Trp Leu Val Ser Ala Ala His
                645                 650                 655

Cys Tyr Ile Asp Asp Arg Gly Phe Arg Tyr Ser Asp Pro Thr Gln Trp
                660                 665                 670

Thr Ala Phe Leu Gly Leu His Asp Gln Ser Gln Arg Ser Ala Pro Gly
            675                 680                 685

Val Gln Glu Arg Arg Leu Lys Arg Ile Ile Ser His Pro Phe Phe Asn
            690                 695                 700

Asp Phe Thr Phe Asp Tyr Asp Ile Ala Leu Leu Glu Leu Glu Lys Pro
705                 710                 715                 720

Ala Glu Tyr Ser Ser Met Val Arg Pro Ile Cys Leu Pro Asp Ala Ser
                725                 730                 735

His Val Phe Pro Ala Gly Lys Ala Ile Trp Val Thr Gly Trp Gly His
            740                 745                 750

Thr Gln Tyr Gly Gly Thr Gly Ala Leu Ile Leu Gln Lys Gly Glu Ile
            755                 760                 765

Arg Val Ile Asn Gln Thr Thr Cys Glu Asn Leu Leu Pro Gln Gln Ile
            770                 775                 780

Thr Pro Arg Met Met Cys Val Gly Phe Leu Ser Gly Gly Val Asp Ser
785                 790                 795                 800

Cys Gln Gly Asp Ser Gly Gly Pro Leu Ser Ser Val Glu Ala Asp Gly
            805                 810                 815

Arg Ile Phe Gln Ala Gly Val Val Ser Trp Gly Asp Gly Cys Ala Gln
```

```
                820                 825                 830
Arg Asn Lys Pro Gly Val Tyr Thr Arg Leu Pro Leu Phe Arg Asp Trp
            835                 840                 845

Ile Lys Glu Asn Thr Gly Val
    850                 855

<210> SEQ ID NO 2
<211> LENGTH: 16
<212> TYPE: PRT
<213> ORGANISM: Homo sapiens

<400> SEQUENCE: 2

Phe Thr Thr Pro Gly Phe Pro Asp Ser Pro Tyr Pro Ala His Ala Arg
1               5                   10                  15

<210> SEQ ID NO 3
<211> LENGTH: 12
<212> TYPE: PRT
<213> ORGANISM: Homo sapiens

<400> SEQUENCE: 3

Gly Asp Ala Asp Ser Val Leu Ser Leu Thr Phe Arg
1               5                   10

<210> SEQ ID NO 4
<211> LENGTH: 13
<212> TYPE: PRT
<213> ORGANISM: Homo sapiens

<400> SEQUENCE: 4

His Pro Gly Phe Glu Ala Thr Phe Phe Gln Leu Pro Arg
1               5                   10

<210> SEQ ID NO 5
<211> LENGTH: 16
<212> TYPE: PRT
<213> ORGANISM: Homo sapiens

<400> SEQUENCE: 5

Ile Phe Gln Ala Gly Val Val Ser Trp Gly Asp Gly Cys Ala Gln Arg
1               5                   10                  15

<210> SEQ ID NO 6
<211> LENGTH: 9
<212> TYPE: PRT
<213> ORGANISM: Homo sapiens

<400> SEQUENCE: 6

Ser Ala Pro Gly Val Gln Glu Arg Arg
1               5

<210> SEQ ID NO 7
<211> LENGTH: 15
<212> TYPE: PRT
<213> ORGANISM: Homo sapiens

<400> SEQUENCE: 7

Ser Phe Val Val Thr Ser Val Val Ala Phe Pro Thr Asp Ser Lys
1               5                   10                  15

<210> SEQ ID NO 8
<211> LENGTH: 11
<212> TYPE: PRT
<213> ORGANISM: Homo sapiens
```

```
<400> SEQUENCE: 8

Ser Gln Phe Val Val Thr Ser Asn Ser Asn Lys
1               5                   10

<210> SEQ ID NO 9
<211> LENGTH: 13
<212> TYPE: PRT
<213> ORGANISM: Homo sapiens

<400> SEQUENCE: 9

Thr Gln Asp Asn Ser Cys Ser Phe Gly Leu His Ala Arg
1               5                   10

<210> SEQ ID NO 10
<211> LENGTH: 116
<212> TYPE: PRT
<213> ORGANISM: Homo sapiens

<400> SEQUENCE: 10

Val Gln Lys Val Phe Asn Gly Tyr Met Arg Ile Thr Asn Glu Asn Phe
1               5                   10                  15

Val Asp Ala Tyr Glu Asn Ser Asn Ser Thr Glu Phe Val Ser Leu Ala
            20                  25                  30

Ser Lys Val Lys Asp Ala Leu Lys Leu Leu Tyr Ser Gly Val Pro Phe
        35                  40                  45

Leu Gly Pro Tyr His Lys Glu Ser Ala Val Thr Ala Phe Ser Glu Gly
    50                  55                  60

Ser Val Ile Ala Tyr Tyr Trp Ser Glu Phe Ser Ile Pro Gln His Leu
65                  70                  75                  80

Val Glu Glu Ala Glu Arg Val Met Ala Glu Glu Arg Val Val Met Leu
                85                  90                  95

Pro Pro Arg Ala Arg Ser Leu Lys Ser Phe Val Val Thr Ser Val Val
            100                 105                 110

Ala Phe Pro Thr
        115

<210> SEQ ID NO 11
<211> LENGTH: 64
<212> TYPE: PRT
<213> ORGANISM: Homo sapiens

<400> SEQUENCE: 11

Val Gln Lys Val Phe Asn Gly Tyr Met Arg Ile Thr Asn Glu Asn Phe
1               5                   10                  15

Val Asp Ala Tyr Glu Asn Ser Asn Ser Thr Glu Phe Val Ser Leu Ala
            20                  25                  30

Ser Lys Val Lys Asp Ala Leu Lys Leu Leu Tyr Ser Gly Val Pro Phe
        35                  40                  45

Leu Gly Pro Tyr His Lys Glu Ser Ala Val Thr Ala Phe Ser Glu Gly
    50                  55                  60

<210> SEQ ID NO 12
<211> LENGTH: 104
<212> TYPE: PRT
<213> ORGANISM: Homo sapiens

<400> SEQUENCE: 12

Val Gln Lys Val Phe Asn Gly Tyr Met Arg Ile Thr Asn Glu Asn Phe
1               5                   10                  15

Val Asp Ala Tyr Glu Asn Ser Asn Ser Thr Glu Phe Val Ser Leu Ala
```

```
                20                  25                  30
Ser Lys Val Lys Asp Ala Leu Lys Leu Leu Tyr Ser Gly Val Pro Phe
            35                  40                  45
Leu Gly Pro Tyr His Lys Glu Ser Ala Val Thr Ala Phe Ser Glu Gly
        50                  55                  60
Ser Val Ile Ala Tyr Tyr Trp Ser Glu Phe Ser Ile Pro Gln His Leu
65                  70                  75                  80
Val Glu Glu Ala Glu Arg Val Met Ala Glu Arg Val Val Met Leu
                85                  90                  95
Pro Pro Arg Ala Arg Ser Leu Lys
            100

<210> SEQ ID NO 13
<211> LENGTH: 119
<212> TYPE: PRT
<213> ORGANISM: Homo sapiens

<400> SEQUENCE: 13

Val Gln Lys Val Phe Asn Gly Tyr Met Arg Ile Thr Asn Glu Asn Phe
1               5                   10                  15
Val Asp Ala Tyr Glu Asn Ser Asn Ser Thr Glu Phe Val Ser Leu Ala
                20                  25                  30
Ser Lys Val Lys Asp Ala Leu Lys Leu Leu Tyr Ser Gly Val Pro Phe
            35                  40                  45
Leu Gly Pro Tyr His Lys Glu Ser Ala Val Thr Ala Phe Ser Glu Gly
        50                  55                  60
Ser Val Ile Ala Tyr Tyr Trp Ser Glu Phe Ser Ile Pro Gln His Leu
65                  70                  75                  80
Val Glu Glu Ala Glu Arg Val Met Ala Glu Arg Val Val Met Leu
                85                  90                  95
Pro Pro Arg Ala Arg Ser Leu Lys Ser Phe Val Val Thr Ser Val Val
            100                 105                 110
Ala Phe Pro Thr Asp Ser Lys
        115

<210> SEQ ID NO 14
<211> LENGTH: 241
<212> TYPE: PRT
<213> ORGANISM: Homo sapiens

<400> SEQUENCE: 14

Val Val Gly Gly Thr Asp Ala Asp Glu Gly Glu Trp Pro Trp Gln Val
1               5                   10                  15
Ser Leu His Ala Leu Gly Gln Gly His Ile Cys Gly Ala Ser Leu Ile
                20                  25                  30
Ser Pro Asn Trp Leu Val Ser Ala Ala His Cys Tyr Ile Asp Asp Arg
            35                  40                  45
Gly Phe Arg Tyr Ser Asp Pro Thr Gln Trp Thr Ala Phe Leu Gly Leu
        50                  55                  60
His Asp Gln Ser Gln Arg Ser Ala Pro Gly Val Gln Glu Arg Arg Leu
65                  70                  75                  80
Lys Arg Ile Ile Ser His Pro Phe Phe Asn Asp Phe Thr Phe Asp Tyr
                85                  90                  95
Asp Ile Ala Leu Leu Glu Leu Glu Lys Pro Ala Glu Tyr Ser Ser Met
            100                 105                 110
Val Arg Pro Ile Cys Leu Pro Asp Ala Ser His Val Phe Pro Ala Gly
        115                 120                 125
```

```
Lys Ala Ile Trp Val Thr Gly Trp Gly His Thr Gln Tyr Gly Gly Thr
    130                 135                 140

Gly Ala Leu Ile Leu Gln Lys Gly Glu Ile Arg Val Ile Asn Gln Thr
145                 150                 155                 160

Thr Cys Glu Asn Leu Leu Pro Gln Gln Ile Thr Pro Arg Met Met Cys
                165                 170                 175

Val Gly Phe Leu Ser Gly Gly Val Asp Ser Cys Gln Gly Asp Ser Gly
            180                 185                 190

Gly Pro Leu Ser Ser Val Glu Ala Asp Gly Arg Ile Phe Gln Ala Gly
        195                 200                 205

Val Val Ser Trp Gly Asp Gly Cys Ala Gln Arg Asn Lys Pro Gly Val
    210                 215                 220

Tyr Thr Arg Leu Pro Leu Phe Arg Asp Trp Ile Lys Glu Asn Thr Gly
225                 230                 235                 240

Val

<210> SEQ ID NO 15
<211> LENGTH: 359
<212> TYPE: PRT
<213> ORGANISM: Artificial sequence
<220> FEATURE:
<223> OTHER INFORMATION: Fusion protein

<400> SEQUENCE: 15

Val Gln Lys Val Phe Asn Gly Tyr Met Arg Ile Thr Asn Glu Asn Phe
1               5                   10                  15

Val Asp Ala Tyr Glu Asn Ser Asn Ser Thr Glu Phe Val Ser Leu Ala
            20                  25                  30

Ser Lys Val Lys Asp Ala Leu Lys Leu Leu Tyr Ser Gly Val Pro Phe
        35                  40                  45

Leu Gly Pro Tyr His Lys Glu Ser Ala Val Thr Ala Phe Ser Glu Gly
    50                  55                  60

Ser Val Ile Ala Tyr Tyr Trp Ser Glu Phe Ser Ile Pro Gln His Leu
65                  70                  75                  80

Val Glu Glu Ala Glu Arg Val Met Ala Glu Glu Arg Val Val Met Leu
                85                  90                  95

Pro Pro Arg Ala Arg Ser Leu Lys Ser Phe Val Val Thr Ser Val Val
            100                 105                 110

Ala Phe Pro Thr Ala Ser Gly Ser Gly Ile Glu Gly Arg Gly Leu Glu
        115                 120                 125

Pro Lys Ser Ser Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
```

-continued

```
                        245                     250                     255
Glu Pro Gln Val Tyr Thr Leu Pro Pro Ser Arg Asp Glu Leu Thr Lys
            260                     265                     270

Asn Gln Val Ser Leu Thr Cys Leu Val Lys Gly Phe Tyr Pro Ser Asp
            275                     280                     285

Ile Ala Val Glu Trp Glu Ser Asn Gly Gln Pro Glu Asn Asn Tyr Lys
            290                     295                     300

Thr Thr Pro Pro Val Leu Asp Ser Asp Gly Ser Phe Phe Leu Tyr Ser
305                             310                     315                     320

Lys Leu Thr Val Asp Lys Ser Arg Trp Gln Gln Gly Asn Val Phe Ser
                    325                     330                     335

Cys Ser Val Met His Glu Ala Leu His Asn His Tyr Thr Gln Lys Ser
            340                     345                     350

Leu Ser Leu Ser Pro Gly Lys
            355
```